US005556981A

United States Patent [19]
Boyd et al.

[11] Patent Number: 5,556,981
[45] Date of Patent: Sep. 17, 1996

[54] ANGIOTENSIN II ANTAGONIST INTERMEDIATES

[75] Inventors: Donald B. Boyd, Greenwood; Sherryl L. Lifer, Indianapolis; Winston S. Marshall, Bargerville; Alan D. Palkowitz; William Pfeifer, both of Indianapolis; Jon K. Reel, Carmel; Richard L. Simon, Greenwood; Mitchell I. Steinberg, Indianapolis; K. Jeff Thrasher, Indianapolis; Venkatraghaven Vasudevan, Indianapolis; Celia A. Whitesitt, Greenwood, all of Ind.

[73] Assignee: Eli Lilly and Company, Indianapolis, Ind.

[21] Appl. No.: 453,532

[22] Filed: May 30, 1995

Related U.S. Application Data

[60] Division of Ser. No. 49,916, Apr. 20, 1993, which is a continuation-in-part of Ser. No. 892,854, Jun. 3, 1992, abandoned.

[51] Int. Cl.$^6$ ...................... C07D 413/10; C07D 209/08
[52] U.S. Cl. .................. 548/238; 548/509; 548/503
[58] Field of Search .................. 548/503, 509, 548/238

[56] References Cited

U.S. PATENT DOCUMENTS

| | | | |
|---|---|---|---|
| 3,772,315 | 11/1973 | Regel et al. | 260/296 R |
| 4,089,962 | 5/1978 | Harrison et al. | 424/269 |
| 4,207,324 | 6/1980 | Matsumura et al. | 424/243 R |
| 4,226,878 | 10/1980 | Iizuka et al. | 424/273 R |
| 4,340,598 | 7/1982 | Furukawa et al. | 424/273 R |
| 4,355,040 | 10/1982 | Furukawa et al. | 424/273 R |
| 4,379,927 | 4/1983 | Vorbrüggen et al. | 544/139 |
| 4,448,781 | 5/1984 | Cross et al. | 424/269 |
| 4,528,195 | 7/1985 | Thorogood | 514/396 |
| 4,582,847 | 4/1986 | Furukawa et al. | 514/400 |
| 4,584,383 | 4/1986 | Pharhi | 546/278 |
| 4,880,804 | 11/1989 | Carini et al. | 514/234 |
| 4,908,363 | 3/1990 | Klotzer et al. | 514/235.8 |
| 4,916,129 | 4/1990 | Carini et al. | 514/235.2 |
| 5,053,329 | 10/1991 | Chen et al. | 435/119 |
| 5,064,825 | 11/1991 | Chakravarty et al. | 514/221 |
| 5,073,566 | 12/1991 | Lifer et al. | 514/381 |
| 5,102,880 | 4/1992 | Chakravarty et al. | 514/212 |
| 5,102,903 | 4/1992 | Smith | 514/406 |
| 5,171,748 | 12/1992 | Roberts et al. | 514/381 |
| 5,173,494 | 12/1992 | Chiu et al. | 514/303 |
| 5,175,164 | 12/1992 | Bagley et al. | 514/259 |
| 5,177,074 | 1/1993 | Allen et al. | 514/234.2 |
| 5,180,724 | 1/1993 | Bowles et al. | 514/248 |
| 5,183,810 | 2/1993 | Greenlee et al. | 514/63 |
| 5,187,159 | 2/1993 | Greenlee et al. | 514/81 |
| 5,210,211 | 5/1993 | Hodges et al. | 548/314.7 |

FOREIGN PATENT DOCUMENTS

| | | |
|---|---|---|
| A-81227/91 | 1/1992 | Australia . |
| 324377 | 7/1989 | European Pat. Off. ...... C07D 233/64 |
| 429257 | 11/1990 | European Pat. Off. ...... C07D 403/06 |
| 468470 | 1/1992 | Germany . |

OTHER PUBLICATIONS

Dunsdon, et al., *Tetrahedron*, 41:14, 2919–2922 (1985).
Danishefsky, et al., *J. Org. Chem.*, 42 (10) 1821–1823 (1977).

*Primary Examiner*—David B. Springer
*Attorney, Agent, or Firm*—Brian P. Barrett; Janelle D. Strode; David E. Boone

[57] ABSTRACT

This invention provides novel heterocyclic derivatives, their pharmaceutical formulations, and their use for antagonizing angiotensin II receptors in mammals.

2 Claims, No Drawings

ANGIOTENSIN II ANTAGONIST INTERMEDIATES

This is a division, of application Ser. No. 08/049,916 filed Apr. 20, 1993, which is a continuation-in-part of application Ser. No. 07/892,854, filed Jun. 3, 1992 now abandoned.

BACKGROUND OF THE INVENTION

The hormone angiotensin II is recognized as one of the most potent vasopressor agents that produces hypertension in mammals. The action of the enzyme renin on the plasma protein substrate angiotensinogen results in the production of an inactive decapeptide, angiotensin I, which upon conversion by the non-selective angiotensin converting enzyme (ACE) provides angiotensin II, the active hormone. See, e.g., Regoli etal., *Pharm. Rev.*, 26, 69 (1974).

Angiotensin II causes vasoconstriction and stimulates aldosterone secretion (from the adrenal gland) that results in a rise of both blood volume and pressure. Inhibitors of angiotensin II are therefore useful in treating hypertension, congestive heart failure, renal insufficiency associated with diabetic or hypertensive nephropathy, and glaucoma. See Garrison et al., in The Pharmacological Basis of Therapeutics, 8th Edition, Eds. A. G. Gilman, E. S. Goodman, T. W. Rall, A. S. Nies, and P. Taylor, Pergamon Press, New York, 1990: p. 761–762; and Dzau V. J., *The New Eng. J. Med*, 324: 1124–1130 (1991).

Angiotensin II also can act on other organs such as the brain (Fitzsimmons, *Rev. Physiol. Biochem. Pharmacol.*, 87, 117, (980)). Antagonist of angiotensin II are therefore useful in enhancing cognitive performance in patients affected by conditions such as age associated mental impairment or Alzheimer's disease and in treating cognitive disorders such as anxiety. See Dennes et al. *Brit. J. Pharmacol.*105: 88p (April 1992); and Barnes, J. M., et al. *FASEB J.* 5: 678 (March 1991).

In addition, angiotensin II acts on a variety of glandular tissues including the kidney, liver, and ovaries. Antagonists of angiotensin II are useful in treating conditions, disorders, or diseases of these tissues associated with excessive or unregulated angiotensin II activity. Antagonists of angiotensin II are also useful in treating kidney damage due to non-steroidal antiinflammatory agents.

Angiotensin II has a role in regulation of the rate of cell growth and differentiation. Inhibitors of angiotensin II are therefore useful in treating disorders marked by excessive cell proliferation such as restenosis. See, e.g., Naftilan et al., *J. Clin. Invest*, 83, 1419 (1989), Kauffman et al., *Life Sciences* 49: 223–228 (1991), and Jackson et. al., *Nature*, 335, 437 (1988).

Some antihypertensive agents act as inhibitors of ACE thus blocking the formation of angiotensin II and its resulting increase of blood pressure. More recently, both peptide and non-peptide receptor antagonists of angiotensin II have been disclosed—see, e.g., EPO Patent Application Publication 253310 and references contained therein, and Chiu et al., *J. Pharmacol. Exp. Ther.*, 250, 867 (1989). Although these compounds and others have had an important role in uncovering the physiological roles for Angiotensin II, their therapeutic usefulness was ultimately limited by either partial agonist activity, metabolic instability or both See Ashworth R. W., *Birkhäuser Verlag*, 26 (1982).

The present invention provides novel, potent, and effective compounds that antagonize angiotensin II at receptor sites in the body and are therefore useful in treating conditions associated with excessive or unregulated angiotensin II activity such as hypertension, congestive heart failure, cognitive disorders, renal insufficiency associated with diabetic or hypertensive nephropathy, glaucoma, kidney damage due to non-steroidal anti-inflammatory agents, and restenosis.

SUMMARY OF THE INVENTION

This invention provides compounds of Formula I

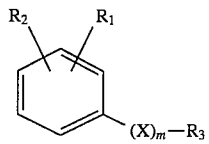
(I)

and pharmaceutically acceptable salts or solvates thereof wherein:

$R_1$ is $CO_2H$, $SO_3H$, $PO_3H_2$, $CONHSO_2R_8$, or 5-tetrazolyl;

$R_2$ is H, —OH, —OCOCH$_3$, halo, $C_1$–$C_4$ alkyl, or $C_1$–$C_4$ alkoxy;

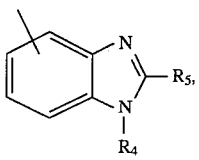
(a)

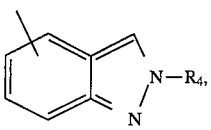
(b)

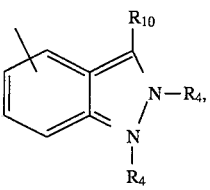
(c)

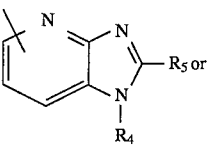
(d)

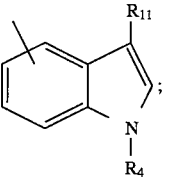
(e)

X is —(CH$_2$)$_m$CONH—, —(CH$_2$)$_m$NHCO—, —CH$_2$—, —O—, —NH—, or —(CH$_2$)$_m$CO—;

$R_4$ is

$C_4$–$C_9$ straight chain alkyl or $C_4$–$C_9$ straight chain trifluoroalkyl providing when $R_4$ is a $C_4$–$C_9$ straight chain alkyl or trifluoroalkyl $R_3$ must be (a) or (d);

$R_5$ is H, $C_1$–$C_5$ alkyl, $C_1$–$C_5$ trifluoroalkyl, $(CF_2)_n CF_3$, benzyl, —$(CH_2)_m N(C_1$–$C_3$ alkyl$)_2$, —$(CH_2)_m NH(C_1$–$C_3$ alkyl), —$CH_2$-1-pyrrolidine, —$(CH_2)_n CO_2H$, or

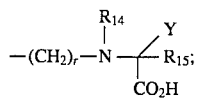

$R_6$ is $(CH_2)_p R_1$, —$CONH(C_1$–$C_4$ alkyl), —$CONH(C_1$–$C_4$ trifluoroalkyl), —$COO(C_1$–$C_4$ alkyl), —$COO(C_1$–$C_4$ trifluoroalkyl), —$CONH$(hydroxy-$C_1$–$C_4$ alkyl),

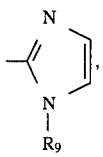 (f)

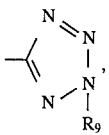 (g)

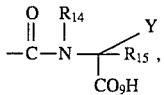 (h)

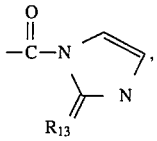 (i)

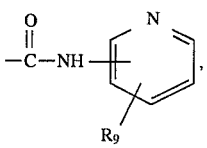 (j)

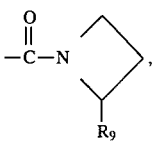 (k)

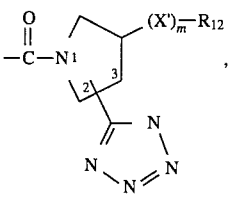 (l)

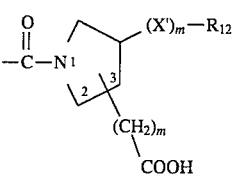 (m)

or

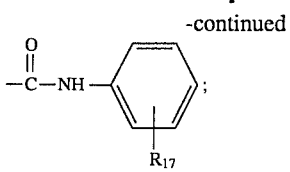 (n)

$R_7$ is $C_4$–$C_9$ straight chain alkyl, $C_4$–$C_9$ straight chain trifluoroalkyl, $C_4$–$C_9$ straight chain alkenyl, or $C_4$–$C_9$ straight chain trifluoroalkenyl;

$R_8$ is phenyl, $C_1$–$C_4$ alkyl substituted phenyl, $C_1$–$C_5$ alkyl, or $C_1$–$C_5$ trifluoroalkyl;

$R_9$ is $(CH_2)_p R_1$, or $C_1$–$C_4$ alkyl;

$R_{10}$ is H or $C_1$–$C_3$ alkyl;

$R_{11}$ is H, $C_1$–$C_4$ alkyl, halo, or —$(CH_2)_r$phenyl;

$R_{12}$ is H, —$(CH_2)_p R_1$, $C_1$–$C_7$ alkyl, $C_1$–$C_7$ trifluoroalkyl, halo, substituted or unsubstituted phenyl, 3-pyridyl, 2-pyrimidyl, furanyl, oxazolyl, isoxazolyl, a substituted or unsubstituted fused bicyclic, a substituted or unsubstituted fused tricyclic, or when m is 0, 4,4ethylenedioxy;

$R_{13}$ is O or S;

$R_{14}$ is H or $CH_3$;

$R_{15}$ is H or —$(CH_2)_q R_{16}$;

$R_{16}$ is OH, $NH_2$, or $CO_2H$;

$R_{17}$ is H, OH, $C_1$–$C_4$ alkoxy, $CO_2H$, $SO_3H$, $PO_3H_2$, $CONHSO_2R_8$, or tetrazolyl;

Y is a R group of a naturally occurring amino acid;

X' is —O—, —$(CH_2)_p$—, or —S—;

m is independently 0 or 1;

n is independently 1, 2 or 3;

p is independently 0, 1, 2, 3 or 4;

q is 1, 2, 3, or 4;

r is independently 0, 1, 2, or 3;

providing when $R_6$ is (l) or (m), and $R_{12}$ is not H, the carboxy of (m) or the tetrazolyl of (l) is in position 2; and when $R_6$ is (l) or (m), m is 0, and $R_{12}$ is H, the carboxy of (m) or the tetrazolyl of (l) is in position 2 or 3.

This invention also provides a method for treating hypertension which comprises administering to a mammal in need of such treatment an antihypertensive amount of a compound of the Formula I.

This invention further provides methods for treating congestive heart failure, renal insufficiency associated with hypertensive or diabetic nephropathy, restenosis, kidney damage due to non-steroidal antiinflammatory agents, anxiety, and glaucoma which comprise administering to a mammal in need of treatment a pharmaceutically effective amount of a compound of the Formula I.

In addition, the present invention provides a method of enhancing cognitive performance which comprises administering to a mammal in need of enhancement a pharmaceutically effective amount of a compound of the Formula I.

Also provided are pharmaceutical formulations comprising of a compound of Formula I together with one or more pharmaceutically acceptable excipients, carriers, or diluents.

An additional aspect of this invention is compounds which are intermediates for preparing compounds of Formula I. These intermediates are represented by Formula II.

$$R_1'\text{—}R_2' \qquad \text{II}$$

wherein:

$R_1'$ is

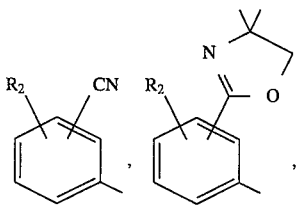

$NO_2$, carboxy, or a protected carboxy group;
$R_2'$ is

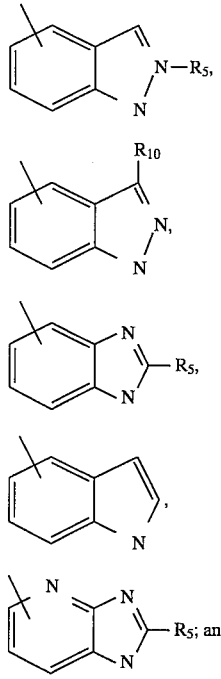

$R_2$, $R_5$, and $R_{10}$ are the same as previously defined.

One further aspect of this invention is a process of preparing the compounds of Formula II wherein $R_2'$ is (s) comprising a. reacting a compound of Formula III

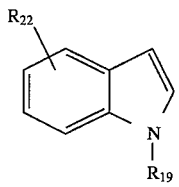

wherein $R_{22}$ is bromo, iodo, —$CH_2$—bromo, or —$CH_2$—iodo; and $R_{19}$ is an indole protecting group; with a reagent selected from an alkyl lithium, $MgBr_2$ or Mg, $ZnCl_2$ or Zn, or diisobutylaluminum chloride to prepare a compound of Formula IV

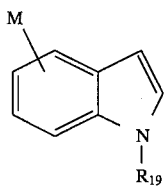

wherein M is $LiR_{22}$, $MgR_{22}$, $ZnR_{22}$, or Al(iso-Butyl)$_2$ respectively;

b. reacting the compound of Formula IV in the presence of a Ni(0) or Pd(0) complex catalyst in an aprotic solvent with a compound of the Formula V

wherein $R_2$ is H, —OH, —$OCOCH_3$, halo, $C_1$-$C_4$ alkyl, or $C_1$-$C_4$ alkoxy; $R_{20}$ is a protected carboxy, cyano, nitro, or methoxy, located in a ortho or para position to $R_{24}$; and $R_{24}$ is bromo or iodo; to produce an indole of Formula VI

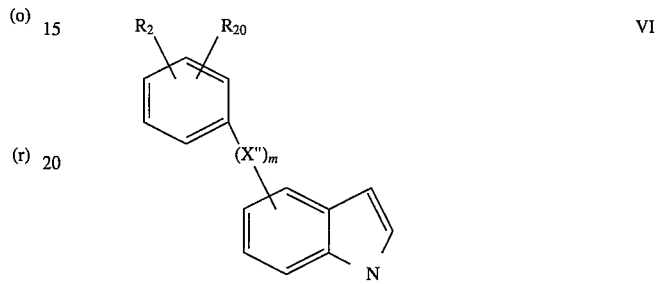

wherein X" is —$CH_2$—; m is 0 or 1; and $R_2$ and $R_{20}$ are the same as previously defined;

c. isolating the compound of Formula VI; and d. deprotecting the Compound of Formula VI.

DETAILED DESCRIPTION AND PREFERRED EMBODIMENT

As noted above, the invention provides compounds of the Formula I which antagonize angiotensin II at the receptor sites in the body. Preferred compounds of this invention are those compounds of Formula I where $R_1$ is 5-tetrazolyl; $R_2$ is hydrogen; $R_3$ is (a) or (d); and R4 contains a L-proline derivative. Particularly preferred compounds are those of Formula Ia.

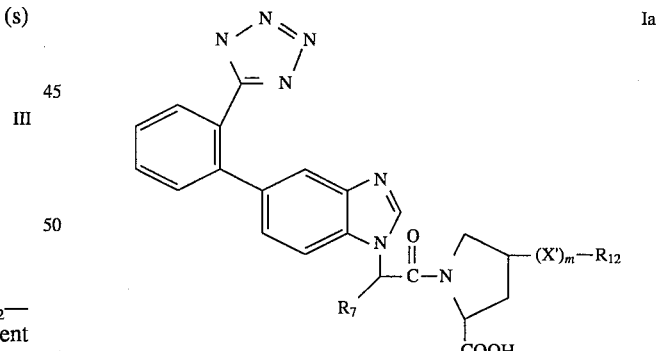

wherein $R_7$ is a $C_4$-$C_9$ straight chain alkyl, X' is —O—; m is 1; and $R_{12}$ is a substituted or unsubstituted phenyl, a substituted or unsubstituted fused bicyclic, or a substituted or unsubstituted fused tricyclic.

Most preferred compounds are compounds in which X' is —O—, and $R_{12}$ is a substituted phenyl of the formula:

$R_{30}$ is $-(CH_2)_pR_1$, $-O(CH_2)_pR_1$, $-SO_2NR_{31}R_{32}$, $-(CH_2)_pCONR_{31}R_{32}$, $-(CH_2)_pNR_{33}SO_2(C_1-C_4$ alkyl or $C_1-C_4$ trifluoroalkyl), or a heteroaryl selected from imidazolyl, triazolyl, tetrazolyl, thioazolyl, isoxazolyl, or oxazolyl, said heteroaryl being optionally substituted with $-(CH_2)_pR_1$; $R_{31}$ and $R_{32}$ are independently H, $C_{1-4}$ alkyl, $-(CH_2)_pCO_2H$, or taken together with nitrogen to which they are bonded constitute a heterocylic ring selected from the groups consisting of pyrrolidino or piperidino, said heterocylic ring being optionally substituted with —COOH; $R_{33}$ is H or $C_1-C_4$ alkyl.

Examples of particularly preferred compounds include the following:

1-[1-Oxo-2-[5-[2-(1H-tetrazol-5-yl)phenyl]-1H-benzimidazol1-yl]octyl]-4-cis-(4-methoxyphenoxy)-L-proline 1-[1-Oxo-2-[5-[2-(1H-tetrazol-5-yl)phenyl ]-1H-benzimidazol-1-yl]octyl]-4-cis-((4-methylene phosphonic acid)-phenoxy)-L-proline 1-[1-Oxo-2-[5-[2-(1H-tetrazol-5-yl)phenyl]-1H-benzimidazolo-1-yl]octyl]-4-cis-(4-carboxyphenoxy)-L-proline 1-[1-Oxo-2-[5-[2-(1H-tetrazol-5-yl)phenyl]-1H-benzimidazol-1-yl]octyl]-4-cis-(4-carboxymethylphenoxy)-L-proline 1-[1-Oxo-2-[5-[2-(1H-tetrazol-5-yl)phenyl]-1H-benzimidazol-1-yl]octyl]-4-cis-(4-thiomethoxyphenoxy)-L-proline 1-[1-Oxo-2-[5-[2-(1-H-tetrazol-5-yl)phenyl]1H-benzimidazol-1-yl]octyl]-4-cis-(4-t-butyloxyphenoxy)-L-proline 1-[1-Oxo-2-[5-[2-91H-tetrazol-5-yl)phenyl]-1H-benzimidazol-1-yl]octyl]-4-cis-(4-methylsulfonyl-phenoxy)-L-proline 1-[1-Oxo-2-[5-[(2-(1H-tetrazol-5-yl)phenyl]-1H-benzimidazol-1-yl]octyl]-4-cis-(5-benzofuranoxy)-L-proline 1-[1-Oxo-2-[5-[2-(1H-tetrazol-5-yl]phenyl]-1H-benzimidazol-1-yl]octyl]-4-cis-(2-napthoxy)-L-proline.

The terms "$C_1-C_3$ alkyl," "$C_1-C_4$ alkyl," "$C_1-C_5$ alkyl," "$C_1-C_7$ alkyl," and "$C_1-C_9$ alkyl" represent a cyclo, straight or branched chain alkyl group having from one to three, four, five, seven, or nine carbon atoms respectively such as methyl, ethyl, n-propyl, isopropyl, n-butyl, isobutyl, sec-butyl, t-butyl, pentyl, isopentyl, 1-methylbutyl, 1-ethylpropyl, neopentyl, tert-pentyl, cyclopentyl, n-hexyl, isohexyl, cyclohexyl, cyclohexylmethyl, 4-methyl hexyl, n-heptyl, t-heptyl, iso-heptyl and the like.

The term "hydroxy-$C_1-C_4$ alkyl" is a $C_1-C_4$ alkyl substituted with a hydroxy. A hydroxy-$C_1-C_4$ alkyl is preferably of the formula $HO(CH_2)_q-$, where q is 1 to 4.

The terms "$C_1-C_4$ trifluoroalkyl," "$C_1-C_5$ trifluoroalkyl," and "$C_1-C_7$ trifluoroalkyl" represent a straight or branched chain alkyl group having from one to four, five, or seven carbon atoms respectively in which the primary carbon is substituted with fluorine.

The term "$C_4-C_9$ straight chain alkyl" represents a straight chain alkyl group having from four to nine carbon atoms. Examples of a "$C_4-C_9$ straight chain alkyl" include n-butyl, n-pentyl, n-hexyl, n-heptyl, n-octyl, and n-nonyl.

The term "$C_4-C_9$ straight chain trifluoroalkyl" represents a $C_4-C_9$ straight chain trifluoroalkyl group in which the primary carbon is substituted with fluorine.

The terms "$C_1-C_4$ alkoxy" and "$C_1-C_7$ alkoxy" represent a $C_1-C_4$ or $C_1-C_7$ alkyl group covalently bonded to the parent moiety by an -O- linkage.

The terms "$C_1-C_4$ trifluoroalkoxy" and "$C_1-C_7$ trifluoroalkoxy" represent a straight or branched chain $C_1-C_4$ trifluoroalkyl group covalently bonded to the parent moiety by an -0- linkage.

The term "halo" includes fluoro, chloro, bromo, and iodo.

The term "$C_4-C_9$ straight chain alkenyl" represents a straight chain alkyl group having from four to nine carbon atoms and one double bond. Examples of a "$C_4-C_9$ straight chain alkenyl" include n-butenyl, n-pentenyl, n-hexenyl, n-heptenyl, n-octenyl, and n-nonenyl.

The term "$C_4-C_9$ straight chain trifluoroalkenyl" represents a $C_4-C_9$ straight chain alkenyl group in which the primary carbon atom is substituted with fluorine. Examples of a "$C_4-C_9$ straight chain trifluoroalkenyl" include 4-trifluoro-n-2-butenyl, 5-trifluoro-n-2-pentenyl, 6-trifluoro-n-3-hexenyl, 7-trifluoro-n-4-heptenyl, 8-trifluoro-n-6-octenyl, and 9-trifluoro-n-5-nonenyl.

The term "$-(CH_2)_pR_1$" represents a straight chain alkyl, branched alkyl, or a straight chain alkenyl bonded to $R_1$ or $R_1$ when p is zero. Examples of "$-(CH_2)_pR_1$" include groups in which the straight chain alkyl, branched alkyl or straight chain alkenyl portion include methylene, ethylene, trimethylene, tetramethylene, methylethylene, ethylethylene, 2-methyltrimethylene, ethenylene, propenylene, and butenylene.

The term "substituted or unsubstituted phenyl" represents phenyl or phenyl substituted with one or more groups selected from $-(CH_2)_pR_1$, $-O(CH_2)_pR_1$, $-(CF_2)_pCO_2H$, $-CONH_2$, $C_1-C_7$ alkyl, $C_1-C_7$ trifluoroalkyl, halo, $-(CH_2)_pOH$, cyano, phenylsulfonyl, phenyl, thiophenyl, thiocarboxy, $C_1-C_7$ trifluoroalkoxy, $C_1-C_7$ alkoxy, $-S(C_1-C_4$ alkyl), $-SO(C_1-C_9$ alkyl), $-SO_2(C_1-C_9$ alkyl), $-SO_2NR_{31}R_{32}$, $-(CH_2)_pCONR_{31}R_{32}$, $-(CH_2)_pNR_{33}SO_2(C_1-C_4$ alkyl or $C_1-C_4$ trifluoroalkyl), or a heteroaryl selected from imidazolyl, triazolyl, tetrazolyl, thioazolyl, isoxazolyl, or oxazolyl, said heteroaryl being optionally substituted with $-(CH_2)_pR_1$; $R_{31}$ and $R_{32}$ are independently H, $C_{1-4}$ alkyl, $-(CH_2)_pCO_2H$, or taken together with nitrogen to which they are bonded constitute a heterocylic ring selected from the groups consisting of pyrrolidino or piperidino, said heterocylic ring being optionally substituted with —COOH; $R_{33}$ is H or $C_1-C_4$ alkyl. Preferably, a substituted or unsubstituted phenyl is a phenyl substituted with one substituent, preferably $-(CH_2)_pR_1$.

The term "fused bicyclic" represents a stable fused bicyclic ring system of the formula:

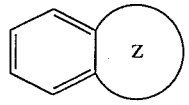

wherein Z represents a substituted or unsubstituted, saturated or unsaturated 5 or 6 membered ring, said ring having from zero to three heteroatoms that are the same or different and that are selected from the group consisting of sulfur, oxygen, and nitrogen; and when Z contains two adjacent carbon atoms, the adjacent carbon atoms may be structured to form a group of the formula $-CH=CH-CH=CH-$; provided that (1) when the heterocyclic ring contains 5 members, the heteroatoms comprise not more than one sulfur or two oxygen atoms but not both; (2) when the heterocyclic ring contains 6 members, sulfur and oxygen are not present; and (3) when the heterocyclic ring contains a sulfur or oxygen atom, the benzofusion is joined to a carbon adjacent to said sulfur or oxygen atom. The fused bicyclic may be attached at any carbon which affords a stable structure. The fused bicyclic may be substituted with one or two groups independently selected from $-(CH_2)_pR_1$, $-O(CH_2)_pR_1$, $-(CF_2)_pCO_2H$, $C_1-C_7$ alkyl, $C_1-C_7$ trifluoroalkyl, halo, $-(CH_2)_pOH$, cyano, phenylsulfenyl, phenyl, thiophenyl, thiocarboxy, $C_1$-$C_7$ trifluoroalkoxy, $C_1$-$C_7$ alkoxy, —S($C_1$-$C_4$ alkyl), —SO($C_1$-$C_9$ alkyl), —SO$_2$($C_1$-$C_9$ alkyl), —SO$_2$NR$_{31}$R$_{32}$; —(CH$_2$)$_p$CONR$_{31}$R$_{32}$, —(CH$_2$)$_p$NR$_{33}$SO$_2$ ($C_1$-$C_4$ alkyl or trifluoroalkyl), or a heteroaryl selected from imidazolyl, triazolyl, tetrazolyl, thioazolyl, isoxazolyl, or oxazolyl, said heteroaryl being optionally substituted with —(CH$_2$)$_p$R$_1$; R$_{31}$ and R$_{32}$ are independently H, $C_{1-4}$ alkyl, —(CH$_2$)$_p$CO$_2$H, or taken together with nitrogen to which they are bonded constitute a heterocyclic ring selected from the groups consisting of pyrrolidino or piperidino, said heterocyclic ring being optionally substituted with —COOH; R33 is H or $C_1$-$C_4$ alkyl.

The term "fused tricyclic" represents a stable fused tricyclic ring system of the formula:

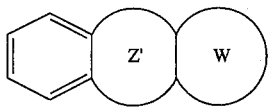

wherein Z' represents a saturated or unsaturated 5 membered ring, said ring having zero or one heteroatom that is selected from the group consisting of sulfur, oxygen, and nitrogen; W represents a substituted or unsubstituted, saturated or unsaturated 6 membered ring, said ring having from zero to three nitrogen atoms. The fused tricyclic may be attached at any carbon which affords a stable structure. The fused tricyclic may be substituted with one or two groups independently selected from —(CH$_2$)$_p$R$_1$, —O(CH$_2$)$_p$R$_1$, —(CF$_2$)$_p$CO$_2$H, $C_1$-$C_7$ alkyl, $C_1$-$C_7$ trifluoroalkyl, halo, —(CH$_2$)$_p$OH, cyano, phenylsulfenyl, phenyl, thiophenyl, thiocarboxy, $C_1$-$C_7$ trifluoroalkoxy, $C_1$-$C_7$ alkoxy, —S($C_1$-$C_4$ alkyl), —SO($C_1$-$C_9$ alkyl), —SO$_2$($C_1$-$C_9$ alkyl), —SO$_2$NR$_{31}$R$_{32}$; —(CH$_2$)$_p$CONR$_{31}$R$_{32}$, —(CH$_2$)$_p$NR$_{33}$SO$_2$($C_1$-$C_4$ alkyl or trifluoroalkyl), or a heteroaryl selected from imidazolyl, triazolyl, tetrazolyl, thioazolyl, isoxazolyl, or oxazolyl, said heteroaryl being optionally substituted with —(CH$_2$)$_p$R$_1$; R$_{31}$ and R$_{32}$ are independently H, $C_{1-4}$ alkyl, —(CH$_2$)$_p$CO$_2$H, or taken together with nitrogen to which they are bonded constitute a heterocyclic ring selected from the groups consisting of pyrrolidino or piperidino, said heterocyclic ring being optionally substituted with —COOH; R$_{33}$ is H or $C_1$-$C_4$ alkyl.

The term "$C_1$-$C_4$ alkyl substituted phenyl" represents a phenyl substituted in any position with a $C_1$-$C_4$ alkyl as previously defined.

The term "R group of a naturally occurring amino acid" represents the variable region of the naturally occurring amino acids and is understood in the art. See, for example, Lehninger A. L. *Biochemistry*, 2nd edition. Worth Publishers, p. 73–75 1975.

The term "carboxy protecting group" as used in the specification refers to one of the ester derivatives of the carboxylic acid group commonly employed to block or protect the carboxylic acid group while reactions are carried out on other functional groups on the compound. The species of carboxy-protecting group employed is not critical so long as the derivatized carboxylic acid is stable to the condition of subsequent reaction(s) and can be removed at the appropriate point without disrupting the remainder of the molecule. See E. Haslam, *Protective Groups in Organic Chemistry*, J. G. W. McOmie, Ed., Plenum Press, New York, N.Y., 1973, Chapter 5, and T. W. Greene, *Protective Groups in Organic Synthesis*, John Wiley and Sons, New York, N.Y., 1981, Chapter 5. A related term is "protected carboxy," which refers to a carboxy-protecting groups.

The term "amino protecting group" as used in the specification refers to substituents of the amino group commonly employed to block or protect the amino functionality while reacting other functional groups on the compound. The species of amino-protecting group employed is not critical so long as the derivatized amino group is stable to the condition of subsequent reaction(s) and can be removed at the appropriate point without disrupting the remainder of the molecule. Preferred amino protecting groups are t-butoxycarbonyl and the benzyloxycarbonyl. See J. W. Barton, *Protective Groups in Organic Chemistry*, J. G. W. McOmie, Ed., Plenum Press, New York, N.Y., 1973, Chapter 2, and T. W. Greene, *Protective Groups in Organic Synthesis*, John Wiley and Sons, New York, N.Y., 1981, Chapter 7. The related term "protected amino" defines an amino group substituted with an amino protecting group as previously discussed.

By virtue of their acidic carboxylic acid, sulfonic acid, phosphonic acid, or tetrazole moieties, the compounds of Formula I include the pharmaceutically acceptable base addition salts thereof. Such salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine ethanolamine and the like. The potassium and sodium salt forms are particularly preferred.

Because of the heterocycle moiety of R$_3$, the compounds of Formula I can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para toluenesulfonic, methanesulfonic, oxalic, para bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, 2-butyne-1,4-dioate, 3-hexyne-2,5-dioate, benzoate, chlorobenzoate, methylbenzoate, dinitrobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycollate, tartrate, methanesulfonate, propanesulfonate, naphthalene-1-sulfonate, naphthalene-2-sulfonate, mandelate and the like salts.

The pharmaceutically acceptable salts of compounds of Formula I can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of Formula I exist. This invention is not limited to any particular stereoisomer but includes all possible individual isomers and mixtures thereof.

The compounds of Formula II, which contain a cyano in the R$_1$' moiety can be converted either to the 5-tetrazolyl final product (R$_1$ is a tetrazolyl), the carboxylic acid final product ($R_1$ is a carboxylic acid) or salts thereof by methods known in the art. The tetrazolyl moieties of $R_1$ in Formula I can be prepared by treating the cyano intermediate with an alkali metal azide such as sodium azide, ammonium chloride or triethylamine hydrochloride, and (optionally) lithium chloride in a non-reactive high boiling solvent such as N,N-dimethylformamide (DMF), preferably at a temperature from about 60°–125° C. Preferably, tri-(n-butyl)tin azide or tetramethylguanadinium azide, neat or in a solvent such as tetrahydrofuran, dimethoxyethane, diethoxyethane, or the like, may be used in place of the alkali metal azide, ammonium chloride, lithium chloride, and DMF.

The carboxylic acids of Formula I can be prepared by the hydrolysis of the cyano intermediate of Formula II ($R_1'$ contains a cyano). The hydrolysis involves the heating of the cyano derivative in aqueous alcohol in the presence of a base such as sodium or potassium hydroxide. The salts of the carboxylic acid and the tetrazole final product are made by reacting the free acid or tetrazole with the appropriate base by standard procedures.

The compounds of Formula I which contain a sulfonamide in the $R_1$ moiety can be prepared by converting the carboxylic acid of $R_1$ to an acid chloride and then reacting the acid chloride with an alkyl sulfonamide by conventional techniques.

The compounds of Formula I which contain a alkoxy moiety ($R_2$ is an alkoxy) may be readily converted to hydroxy compounds of Formula I by techniques known in the art. For example, the alkoxy may be cleaved with boron tribromide to form the hydroxy moiety.

The desired products from the above reactions can be isolated by conventional means, and preferably by chromatography. Column chromatography is a preferred method. High pressure column chromatography over silica gel and high pressure reverse phase chromatography offer the most efficient way of purifying the final products. Alternatively crystallization of the acid, tetrazole, or salts may be employed to purify t]he desired final product.

One process for preparing the benzimidazoles, substituted benzimidazoles, indoles and substituted indoles of Formula I involves the alkylation of intermediates of the Formula II with an alkylating reagent VII as summarized in Scheme 1.

Scheme 1

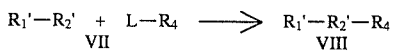

where $R_1'$, $R_2'$, and $R_4$ are the same as previously defined. If $R_4$ is

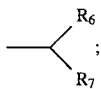

$R_6$ is —(CH$_2$)$_p$R$_1$. However, if $R_1$ contains a carboxy it should be protected as an ester. If $R_1$ is tetrazole, it is preferred that the above reaction be carried out with the nitrile and subsequently convert the nitrile to the tetrazole. When preparing the benzimidazoles of Formula I, the preferred ester is 2-(2-hydroxyethyl)pyridine. $R_7$ is the same as previously defined.

L is a good leaving group such as chloro, bromo, iodo, mesyl, tosyl, and the like. L may also be a hydroxy or other precursor which may be readily converted to a good leaving group by techniques known in the art. For example, the hydroxy may be readily converted to a sulfonic ester such as mesyl by reacting the hydroxy with methanesulfonic anhydride to produce the mesylate leaving group.

This reaction usually involves approximately equimolar amounts of the two reagents, although other ratios, especially those wherein the alkylating reagent is in excess, are operative. The reaction is best carried out in a polar aprotic solvent employing an alkali metal salt or other such alkylation conditions as are appreciated in the art. When the leaving group is bromo or chloro, a catalytic amount of iodide salt, such as potassium iodide may be added to speed the reaction. Preferred reaction conditions include the following: lithium bromide and dimethylformamide, potassium fluoride on alumina in dimethylformamide, sodium bicarbonate in dimethylformamide, sodium hydride in dimethylformamide, potassium carbonate, potassium iodide, and either methylethyl ketone or acetone. The temperature of the reaction is preferably from about ambient temperature to about the reflux temperature of the reaction mixture. When elevated temperatures are employed, the reaction is generally complete in 1–4 hours.

when $R_6$ is protected as an ester, the ester may be readily converted into the acid by methods known in the art. For example, the ester moiety may be hydrolyzed with an aqueous base such as 2N NaOH in methanol. The pH lowered to 3.0 with 5N HCL. The acid product may then be extracted by conventional means.

When $R_6$ is protected as a nitrile, the nitrile may be converted to either a tetrazole derivative or a carboxylic acid by methods known in the art and previously discussed.

One process of preparing the compounds of Formula I that contain an imidazolyl alkyl acid or an imidazolyl alkyl in the $R_4$ moiety ($R_6$ is (f)) involves the alkylation of intermediates of Formula II with an alkylating reagent IX containing the imidazole derivative as summarized in Scheme 2.

Scheme 2

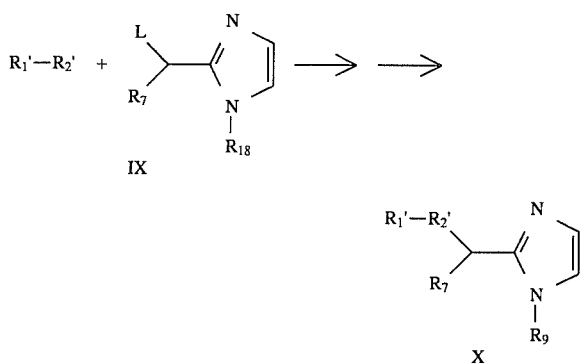

$R_1'$, $R_2'$, $R_1$, $R_7$, $R_9$, and L are the same as previously defined. $R_{18}$ is an imidazole protecting group such as benzyl, trityl, methoxy methyl, diethyl methyl, dimethyl sulfonamoyl, or 2-(trimethyl silyl)ethoxymethyl. It is preferred that the imidazole is protected during the coupling. See Jones, J. Am. Chem, Society 71: 383 (1949), Kirk, J. Org. Chem. 43: 438 (1978), and Turner et al. J. Org, Chem. 56: 5739 (1991).

This reaction occurs at conditions substantially the same as Scheme 1. The reaction usually involves approximately equimolar amounts of the two reagents, although other ratios, especially those wherein the alkylating reagent is in excess, are operative. The reaction is best carried out in a polar aprotic solvent employing an alkali metal salt or such alkylation conditions as are appreciated in the art. When the leaving group is bromo or chloro, a catalytic amount of iodide salt, such as potassium iodide may be added to speed the reaction. Preferred reaction conditions include the following: lithium bromide and dimethylformamide, potassium fluoride on alumina in dimethylformamide, sodium bicarbonate in dimethyl-formamide, sodium hydride in dimethylformamide, potassium carbonate, potassium iodide, and either methylethyl ketone or acetone. The temperature of the reaction is preferably from about ambient temperature to about the reflux temperature of the reaction mixture.

The imidazole protecting group ($R_8$) may be cleaved as pare of the above alkylation. If not, the protecting group must be removed by a deprotection reaction. The imidazole may be deprotected by methods known in the art. For example, the trityl blocking group may be removed by treating the compound with 2N hydrochloric acid at 60°–70° C. See Kelly et at., *J. Med. Chem.* 20: 721–723 (1977). Once the imidazole protecting group is removed, the substituent, $R_9$, may be added to the imidazole by alkylation reactions known in the art and previously discussed.

A process of preparing the compounds of Formula I that contain an tetrazolyl alkyl acid in the $R_4$ moiety ($R_6$ is (g)) involves the alkylation of intermediates of Formula II with an alkylating reagent IX containing the tetrazolyl derivative in a reaction analogous to Scheme 2.

One process of preparing the compounds of Formula I where m is one is summarized in Scheme 3.

Scheme 3

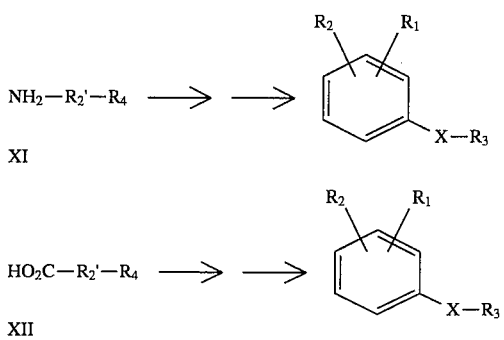

$R_1$, $R_2$, $R_3$, $R_4$, X, and $R_2'$ are the same as previously defined. Preferably, if $R_3$ contains a carboxy moiety (i.e., $R_4$ contains a carboxy) it should be protected during the reaction scheme.

Compounds of Formula I that contain a carboxamide linkage (X is —$(CH_2)_m$CONH—) may be prepared by reacting Compound XI with a carboxylic acid. For example, to form the carboxamide linkage with a tetrazole moiety in $R_1$, Compound XI is coupled with 2-tetrazol-5-yl-benzoic acid.

Compound XI can be prepared by hydrogenating the nitro containing compounds of Formula II by conventional techniques. For example, the nitro may be hydrogenated over palladium on charcoal in an alcohol such as ethanol to form an amine (Compound XI).

The coupling reaction between Compound XI and the substituted benzoic acid may be accomplished by any of several known methods of coupling carboxylic acids to amines.

For example, the carboxylic acid can be transformed into an acid halide, particularly the acid chloride and then reacted with the amine to provide the amide linkage. Conversion of the acid to the corresponding acid chloride may be accomplished upon treatment with a reagent such as thionyl chloride or oxalyl chloride optionally in the presence of an aprotic nonreactive solvent. Preferred combinations include thionyl chloride treatment followed by reaction of the amine in tetrahydrofuran in the presence of potassium carbonate, or reaction of oxalyl chloride with the carboxylic acid followed by addition of the amine in dimethylformamide and triethylamine or diisopropyl ethylamine. The amine can also be introduced as an acid salt and added together with a nonreactive base. Thus, the amine hydrochloride may be added with triethylamine, pyridine, or the like.

Alternatively, other amide condensing reagents may also be employed such as 1,1-carbonyldiimidazole or 1,3-dicyclohexylcarbodiimide. These reagents are usually employed in a nonreactive high boiling solvent such as dimethylformamide and optionally in the presence of reagents such as diisopropylethylamine, hydroxybenzo triazole, and the like in order to facilitate reaction.

The carboxamide type linkage may also be accomplished by reacting the amine (Compound XI) with the corresponding anhydride. This reaction is particularly useful when the acid moiety in $R_1$ is sulfonic or carboxylic. For example, 1,2-benzenedi-carboxylic anhydride or 1,3-isobenzofurandione may be reacted with the amine to form the carboxamide type linkage with $R_1$ as a carboxylic acid. The sulfonic acid may be prepared similarly by reacting sulfobenzoic anhydride with the amine to form the carboxamide type linkage with $R_1$ as a sulfonic acid. These reactions are accomplished by mixing the two reagents in one or more nonreactive solvents, such as tetrahydrofuran or acetonitrile. This reaction is the preferred method of preparing the compounds of Formula I that contain a carboxamide linkage. The anhydride may be readily substituted with a alkoxy, hydroxy or —OCOCH$_3$ to form the desired $R_2$ moiety and reacted as described above.

Alternatively, anhydrides may be reacted with one equivalent of an alcohol to provide a monoacid monoester which may be coupled with Compound XI by methods previously discussed.

Compounds of Formula I that contain a tetrazolyl in the $R_1$ moiety and a carboxamide type linkage (X is —$(CH_2)_m$NHCO—) may be prepared by similar reaction conditions but employing carboxy moiety (Compound XII) with an ortho aminobenzonitrile. Once the coupling is completed, the nitrile may be readily converted to the tetrazolyl or carboxy moiety as previously discussed.

The amine type linkage (X is —NH—) may be accomplished by methods known in the art. For example, an Ullman reaction may be performed on Compound XI and a bromo containing compound such as 2-bromobenzonitrile to form compounds of the Formula I. Typical Ullman conditions include the reaction of the reagents in the presence of copper bronze and copper chloride in pyridine or dimethylformamide.

The ether linkage (X is —$(CH_2)_m$CO—) can also be prepared by the Ullman reaction employing the hydroxy analog of Compound XI. It is preferred chat the acid moieties be protected during the reaction.

The ketone linkage (X is —$(CH_2)_m$CO—) for the compounds of Formula I which are indoles or indazoles may be prepared by coupling compound XIV with a substituted benzenecarbaldehyde as described in Scheme 4.

Scheme 4

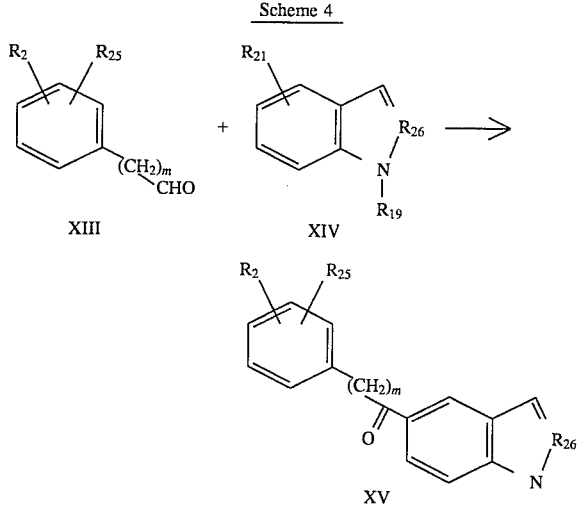

$R_{25}$ is defined to be a protected carboxy group, protected thiol group, protected phosphonic group, oxazoline, or cyano. Preferably, $R_{25}$ is protected as a salt or an ester. $R_{26}$ is C or N. $R_2$ and m are the same as previously defined. However, if $R_2$ is defined to be OH, it must be protected during the coupling reaction. Preferably, the coupling is carried out with the hydroxy protected as an alkoxy and subsequently deprotecting as previously discussed. $R_{19}$ is a indole protecting group as described in Greene, *Protecting Groups of Organic Synthesis*, 218–270 (1981). $R_{21}$ is halo.

Compound XIV is reacted with a lithiating reagent such as an alkyl lithium (e.g., Butyl-Li) in a metal halogen exchange. The resulting litho indole intermediate may then be reacted with the benzenecarbaldehyde (Compound XIII) and oxidized by conventional techniques to provide the desired intermediate XV. The reaction is best carried out in an aprotic solvent with an approximately equimolar ratio of the reactants. The protecting group ($R_{25}$ and/or $R_{19}$ moieties) may be removed by techniques known in the art or previously discussed.

The ketone linkage (X is —$(CH_2)_mCO$—) for the compounds of Formula I which are benzimidazoles or azabenzimidazoles may be prepared as described in Scheme 5.

Scheme 5

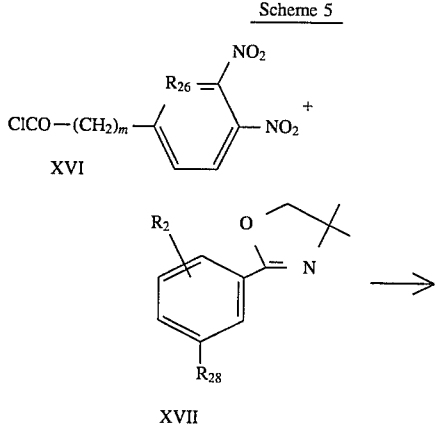

-continued
Scheme 5

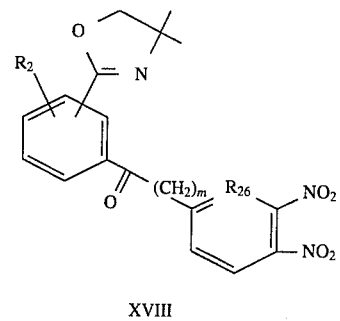

$R_{28}$ is H or halo. $R_2$, m, and $R_{26}$ are the same as previously defined. However, if $R_2$ is defined to be OH, it must be protected during the coupling reaction. It is preferred that the hydroxy is protected as an alkoxy and subsequently deprotecting. Compound XVIII may be prepared by reacting Compound XVII, with a lithiating agent as previously discussed to produce the corresponding lithio intermediate. The lithio intermediate may then be reacted with compound XVI, an acid chloride, to produce compound XVIII with the oxazoline in the preferred ortho position to the ketone linkage.

Alternately, the para oxazoline of Compound XVIII may be prepared by reacting Compound XVII with the acid chloride in a Friedel-Crafts acylation. The Friedel-Crafts acylation is best carried out in the presence of a Lewis acid such as aluminum chloride, in a non-reactive solvent such as dichloromethane.

The oxazoline may be converted to a carboxy moiety or a cyano by techniques known in the art. See Meyers et al., *J. of Am. Chem. Soc.* 97: 7383–7385 (December, 1975).

Compound XVIII may be hydrogenated by conventional techniques and further reacted as described in Scheme 10 to form the benzimidazole or substituted benzimidazole of Formula I.

The process of preparing the compounds of Formula I which are carboxamido derivatives is summarized in Scheme 6.

Scheme 6

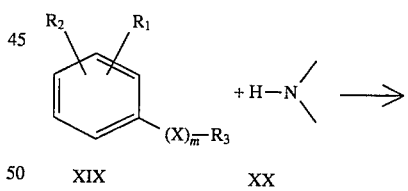

Carboxamido derivatives of Formula I

Compound XIX is a compound of the Formula I in which $R_6$ contains a carboxylic acid. Carboxamido derivatives of Formula I include, for example, compounds in which $R_6$ is defined to be (h), (i), (j), (k), (l), (m), (n), —$CONH(C_1-C_4$ alkyl), —$CONH(C_1-C_4$ trifluoroalkyl), —$CONH$(hydroxy-$C_1-C_4$ alkyl). Compound XX is the appropriate amine to produce the desired carboxamido derivative of Formula I.

The coupling reaction between the Compound XIX and an amine is a standard coupling reaction between carboxylic acids and amines. Preferably, if the amine contains a carboxyl, the carboxyl group is protected during the reaction by a protecting group by methods known in the art. Alternatively, if the amine is a hydroxyproline derivative, the lactone may be prepared to protect the carboxyl during the coupling reaction.

The coupling reaction between carboxylic acids and amines can be accomplished by any of several known methods. The preferred method in this scheme is to employ an amide condensing reagent, 1,3-dicyclohexylcarbodiimide, in a nonreactive high boiling solvent such as dimethylformamide in the presence hydroxybenzotriazole.

The alkyl ester or trifluoroalkyl ester of Formula I ($R_6$ is —COO($C_1$-$C_4$ alkyl) or —COO($C_1$-$C_4$ trifluoroalkyl)) can be prepared by reacting the acid chloride of compound XIX with the appropriate alcohol. For example, to form the trifluorobutyl ester, the acid chloride may be reacted with trifluorobutanol. This coupling may be accomplished by methods known in the art. The reaction is typically carried out in a non reactive solvent in the presence of a non reactive base such as triethylamine or pyridine.

An additional aspect of the present invention is a novel process of preparing the compounds of Formula II which are the intermediates of the indole and substituted indole derivatives of Formula I. The process is summarized in Scheme 7.

Scheme 7

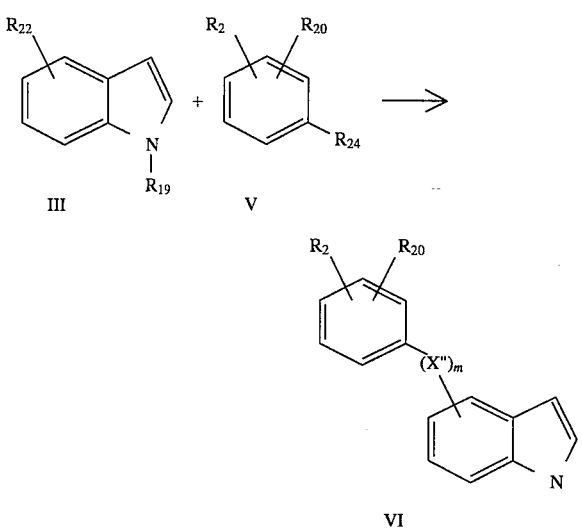

$R_{20}$ is a protected carboxylic group, cyano, nitro or methoxy, located ortho or para to $R_{24}$. X" is —$CH_2$—. $R_2$, m, and $R_{19}$ are the same as previously defined. $R_{22}$ is a bromo, iodo, —$CH_2$-bromo, or —$CH_2$-iodo. $R_{24}$ is bromo or iodo. However, if $R_2$ is defined to be OH, it should be protected during the coupling reaction. It ms preferred to carry out the coupling with the hydroxy protected as a alkoxy and subsequently deprotecting as previously discussed. Preferably, $R_{22}$ is a bromo; $R_{24}$ is bromo; $R_{20}$ is a cyano; and $R_{19}$ is triisopropylsilylindole.

This coupling as depicted in Scheme 7 is a novel process of preparing indole intermediates of the Formula II.

The first step of the process is to react the halo indole (III) with a reagent selected from alkyl lithium, $MgBr_2$ or Mg, $ZnCl_2$ or Zn, or diisobutylaluminum chloride to prepare an organometallic indole of the formula

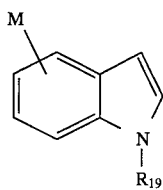

IV wherein M is a Li, $MgR_{22}$, $ZnR_{22}$, or Al(i-Butyl)$_2$ respectively. For example, to prepare the lithium indole, Compound III is reacted with an alkyl lithium. The magnesium halide indole is prepared as a Grignard reagent or by reacting the lithio indole with magnesium bromide. The zinc chloride indole is most readily prepared by reacting the lithio indole with anhydrous zinc chloride. The diisobutylalane (Al(i-Butyl)$_2$) is most readily prepared by reacting lithio indole with diisobutylaluminum chloride. The zinc organometallic indole is the preferred reagent. The zinc organometallic indole is most readily prepared in an aprotic solvent such as ether, dioxane, or preferably tetrahydrofuran below about –60° C.

The catalyst used in the coupling reaction is a Ni(0) or Pd(0) complex catalyst. The preferred catalyst is prepared in situ by reacting nickel acetylacetonate and triphenylphosphine and reducing the nickel using a metal hydride reducing agent such as lithium aluminum hydride or preferably diisobutylaluminum hydride. This catalyst is best prepared ac low temperatures, below about –60° C. Other transition metal catalyst such as palladium chloride, or tetratriphenyiphosphine palladium zero may be employed. When $R_{20}$ is nitro, the palladium catalyst is preferred.

Compound V and the indole solution are added preferably in an approximately equimolar ratios. It is advantageous to add the substituted benzene, Compound V, several minutes before adding the indole solution. The reaction occurs at ambient temperatures. The product, Compound VI—a substituted phenyl indole, is isolated by conventional means.

This process may be used co prepare the indoles of Formula I which contain a —$CH_2$—linkage (X is $CH_2$). To prepare the $CH_2$ linkage, $R_{21}$ is defined to be —$CH_2$—halo. Compound III may then be coupled with compound V as previously described to form compound VI with a —$CH_2$—linkage.

The indole protecting group may be removed by conventional techniques. Greene, *Protecting Groups of Organic Synthesis*, at 283. For example, the triisopropylsilyl group is removed by reacting the protected indole with tetra-n-butylammonium fluoride at room temperature. The deprotection is best carried out in an aprotic solvent such as tetrahydrofuran. This scheme is the preferred process of preparing Compound VI, the intermediates of the indole and substituted indole derivatives of Formula I.

When preparing the phosphonic acid derivatives of Formula I ($R_1$ is $PO_3H_2$), Compound V is nitrobromobenzene ($R_{20}$ is nitro, $R_{21}$ is bromo). The nitro moiety of the resulting Compound VI may be converted to a halo and subsequently to the phosphonic ester by techniques known in the art. For example, the product of the scheme, 5-(2-nitrophenyl)indole, may be converted to an amine by reacting the amine with HBr to form the bromo substituted phenyl and further reacting the bromo moiety with triethyl phosphite in a nickel chloride solution. The phosphonic ester may then be hydrolyzed to form the phosphonic acid.

when preparing the sulfonic acid derivatives of Formula I ($R_1$ is $SO_3H$), Compound V is 1-bromo 2-methoxybenzene. Compound VI therefore contains a methoxy moiety which may be converted to a sulfonic acid by techniques known in the art. For example, Compound VI may be reacted with boron tribromide and chlorothiocarbamate. The resulting intermediate may undergo a Newman rearrangement by applying heat and oxidizing to form the sulfonic moiety. See Newman et al. *J. of Org. Chem.* 31: 3980 (1966).

An alternative process of preparing the compounds of Formula II that are intermediates of indole and substituted indole derivatives of Formula I and that also contain a carboxy moiety in $R_1$ is summarized in Scheme 8.

Scheme 8

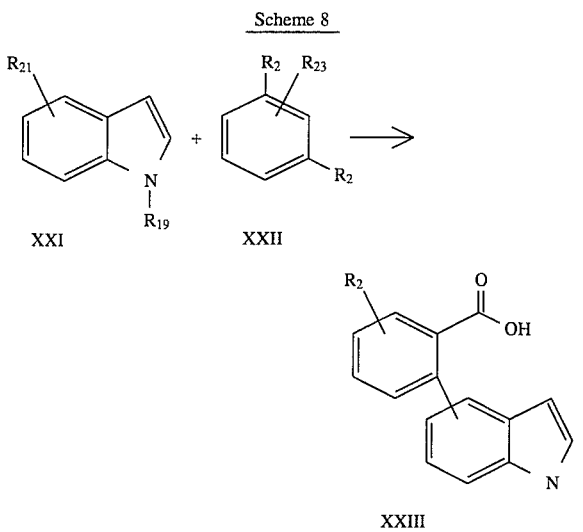

$R_{19}$ and $R_{21}$ are the same as previously defined. $R_2$ is independently the same as previously defined providing that at least one $R_2$ is an alkoxy. However, if $R_2$ is defined to be OH, it must be protected during the coupling reaction. It is preferred to carry out the coupling with the hydroxy protected as an alkoxy and subsequently deprotecting as previously discussed. $R_{23}$ is a oxazoline or substituted amide. Preferably, $R_{19}$ is triisopropyl-silylindole; $R_{21}$ is bromo; $R_{23}$ is an oxazoline; and $R_2$ is methoxy and hydrogen.

This reaction usually involves approximately equimolar ratios of the reactants. The reaction begins with a metal halogen exchange of Compound XXI. Compound XXI, a halo indole, is reacted with a lithiating agent to exchange the halo for a lithium resulting in a lithio indole. The reaction is carried out at low temperatures (below about $-60°$ C.) and in a nonreactive solvent. Preferably, the reaction is carried out in tetrahydrofuran or mixtures of tetrahydrofuran in other solvents.

The subsequent coupling reaction is the displacement of the alkoxy from Compound XXII with the lithio indole produced by the metal halogen exchange. The reaction is best carried out in tetrahydrofuran at ambient temperatures. As previously discussed, the indole protecting group is removed by conventional techniques.

The oxazoline protecting group may be converted to the carboxylic moiety of $R_1$ of Formula I by methods known in the art and previously discussed.

The indoles of Formula I which contain a ketone linkage (X is —CO—) and a meta $R_1$ substitution ($R_1$ is meta to the ketone linkage) may be prepared by reacting Compound XXI with an lithiating agent to exchange the halo for lithium, and then coupling the lithioindole with an acid chloride such as 3-bromobenzoyl. The resulting bromo indole intermediate can be converted to the cyano intermediate and deprotected by techniques previously discussed.

One process of preparing the compounds of Formula I that contain a 3-substituted indazole derivative ($R_3$ is a 3-substituted indazole) is summarized in Scheme 9.

Scheme 9

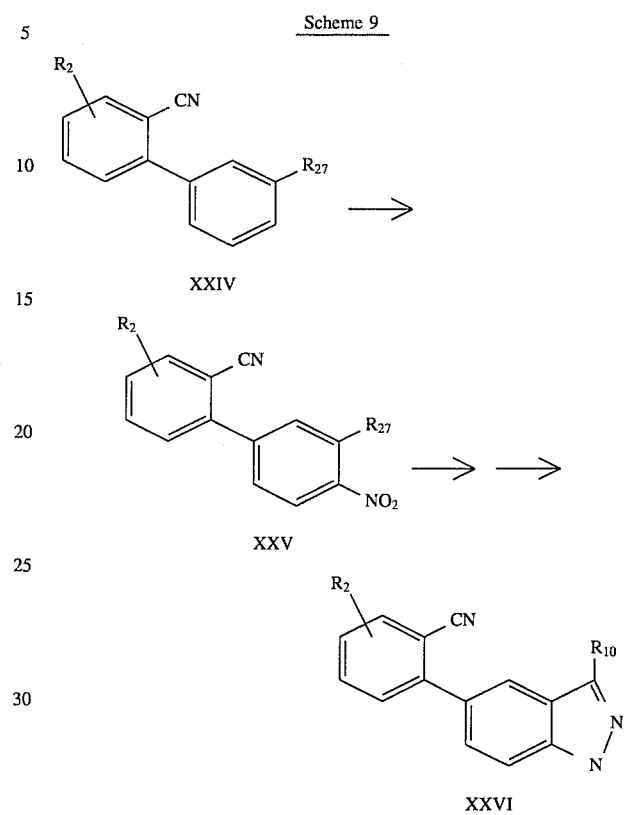

$R_{27}$ is defined to be $C_1$–$C_4$ alkyl. $R_2$ is the same as previously defined. However, if $R_2$ is defined to be OH, it should be protected during the coupling reaction. It is preferred to carry out the coupling with the hydroxy protected as an alkoxy and subsequently deprotecting as previously discussed.

Compound XXIV is nitrated by conventional techniques. For example, Compound XXIV may be added slowly to a mixture of nitric acid and sulfuric acid, diluted with cold water, dissolved in tetrahydrofuran and condensed to the 4-nitro derivative of Compound XXIV. This derivative is then hydrogenated, acetylated with acetic anhydride and further reacted to form the indazole, Compound XXVI, as described in Baumgarten, *Organic Synthesis Collective Volume 5*: 650–653 (1973).

The 3-substitution ($R_{10}$) may be achieved by employing the desired $R_{27}$ substituent. For example, the ethyl substitution ($R_{10}$ is ethyl) may be prepared by employing Compound XXIV with $R_{27}$ defined to a propyl in the above scheme.

A process of preparing the compounds of Formula II which are the intermediates of the benzimidazole and the substituted benzimidazole derivatives of Formula I is summarized in Scheme 10.

Scheme 10

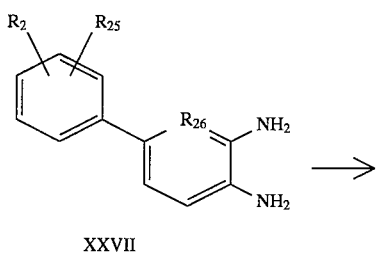

XXVII

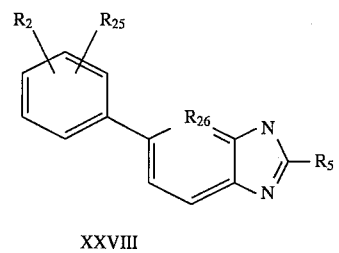

XXVIII $R_2$, $R_{26}$, $R_{25}$ and $R_5$ are the same as previously defined. However, if $R_2$ is defined to be OH, it must be protected during the coupling reaction. It is preferred to carry out the coupling with the hydroxy protected as an alkoxy and subsequently deprotecting as previously discussed.

Compound XXVII, a diamine, may be readily converted into a benzimidazole by techniques known in the art such as reacting Compound XXVII with an ester, carboxylic acid, or an imino ether.

For example, the compounds of Formula II may be prepared by reacting the diamine with the desired carboxylic acid. Therefore, to prepare the unsubstituted benzimidazole, the diamine is reacted with formic acid. Likewise, to prepare a 2-substituted benzimidazole such as trifluoromethyl benzimidazole, the diamine is reacted with trifluoroacetic acid. Preferably, the reaction is carried out at the reflux temperature.

Alternatively, the 2-substituted benzimidazole may be prepared employing the imino ether with Compound XXVII. For example, Compound XXVII may be reacted with ethyl hexanoamidate hydrochloride in ethanol to form the pentyl substitution. Likewise, the —$(CH_2)_m$-amino compounds may be prepared by reacting Compound XXVII with a halo substituted imino ester, e.g., ethyl chloroacetoimidate, and subsequently substituting the halo by an amino-dehalogenation reaction. For example, the 2-chloromethyl substitution of Compound XXVIII may be prepared as described and further reacted with dimethylamine to form 2-dimethylaminomethyl substitution on Compound XXVIII ($R_5$ is dimethyl-aminomethyl).

The compounds of Formula I which contain an acid moiety in $R_5$ may be most readily prepared by reacting Compound XXVII with a dicarboxylic acid in an aprotic solvent. Preferably, one of the carboxy groups is protected. Examples of dicarboxylic acids which contain a protected carboxy group include mono methylsuccinate, mono methylglutarate, and the like. The unprotected carboxy in the acid is reacted co form an active ester by reacting the acid with an alcohol in the presence of a dehydrating agent. The active ester then reacts with the diamine to form Compound XXVIII with $R_5$ containing a protected carboxy. Preferably, the dehydrating agent is dicyclohexylcarbodiimide and the alcohol is hydroxybenzotriazole. The carboxy may then be deprotected by techniques known in the art.

An active ester is defined to mean an ester which renders the carboxyl function of the acylating group reactive to coupling with the diamino groups of Compound XXVII.

The benzimidazoles of Formula I which contain a ketone linkage (X is —$(CH_2)_mCO$—) and a meta $R_1$ substitution ($R_1$ is meta to the ketone linkage) may be prepared by techniques known in the art. For example the ketone linkage (X is —CO—, m is 0) may be prepared by brominating 4-amino-3-nitrobenzophenone and displacing the bromide with a nitrile by techniques known in the art and previously discussed. The nitro may then be hydrogenated and reacted according to Scheme 10 to form 5-(3-cyanobenzoyl)-1H-benzimidazole intermediate.

The 3-substituted indoles of Formula I are readily prepared by techniques known in the art. For example, the 3-substituted indoles of Formula I may be prepared by reacting the indole with a Grignard reagent such as ethyl magnesium bromide and then reacting the indole with an alkyl halide. For instance, to form the 3-propyl indole derivative, the alkyl halide could be propyl bromide.

The substituted phenoxy proline derivatives may be readily prepared in accordance with Scheme 11.

Scheme 11

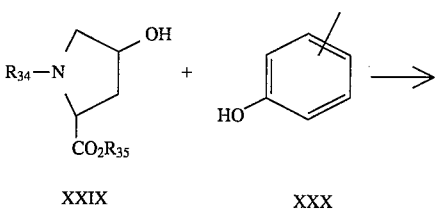

XXIX             XXX

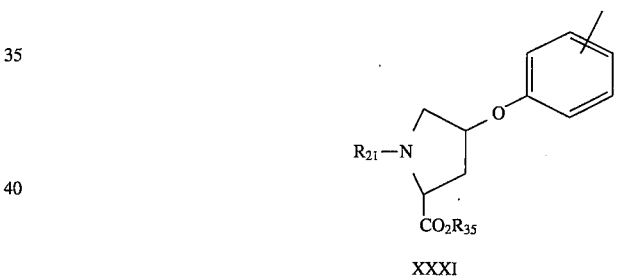

XXXI

In scheme 11 above $R_{34}$ is a amino protecting group, preferably carbobenzyloxy; $R_{35}$ is a carboxy protecting group, preferably a $C_1$–$C_4$ alkyl to form an ester. The phenol, Compound XXX, reacted in accordance with this scheme to prepare the compounds of Formula I wherein $R_{12}$ is a substituted phenyl as previous by defined.

The reaction protrayed is a known in the art as a Mitsunobu reaction. See Mitsunobu, O., *Synthesis* 1 (1981). Preferably, the reaction is carried out in the presence of triphenylphosphine and diethyl azodicarboxylate in an aprotic solvent such as THF. At the completion of this scheme Compound XXXI may be deprotected to form the amino and further reacted in accordance with scheme 6.

As noted above, the compounds of this invention contain at least one chiral center, that being the carbon atom in the group $R_4$. While all of the above schemes address reactions involving racemic reagents and products, each of the reactions can be performed using a chiral starting material to provide a particular enantiomer of interest. The reactions of Scheme 1 and Scheme 2 are particularly useful since the introduction of the chiral center is the penultimate step. Alternatively, particular isomers can be isolated from the racemate by resolution employing standard methods, such as fractional crystallization, high pressure liquid chromatography, reverse phase chromatography and the like. These resolutions can be accomplished either on the final product Formula I, intermediate Formula II, at any stage along the synthetic pathway, or on derivatives of the final product and intermediate.

In all of the above schemes, it is preferred that the reactions be carried out wherein all of the $R_1$ groups are protected during the coupling reaction and deprotected as described above. However, one skilled in the art recognizes that many of these reactions can be performed on the free acid or tetrazole if the appropriate reaction conditions, blocking reagents, or the like are used. Since the $R_1$ moieties are considerably different in their sensitivity to hydrolysis, the sequence for transforming intermediates of the Formula II to final products having both an acid and tetrazole group is not critical.

Compounds III, V, VII, IX, XIII, XIV, XVI, XVII, XX, XXI, XXII, and XXIV, XXIX, XXX and any other reagents required for their transformation, are either commercially available, known in the art, or can be prepared by methods known in the art.

The following examples and preparations are provided merely to further illustrate the invention. The scope of the invention is not construed as merely consisting of the following examples.

In the examples and preparations melting point, nuclear magnetic resonance, mass spectrometry, high pressure liquid chromatography over silica gel, N,N-dimethylformamide, palladium on charcoal, diisobutylaluminum hydride, and tetrahydrofuran are abbreviated M.Pt., NMR, MS, HPLC, DMF, Pd/C, DIBAL and THF, respectively. The terms "NMR" and "MS" indicate that the product spectrum was consistent with the desired structure.

Preparation 1

2-Cyanobiphenyl

A solution of $ZnCl_1$(0.735M, 100 g anhydrous) in THF (200 ml) was cooled to −50° C. Phenyllithium (0.725 moles, 403 ml in cyclohexane/diethyl ether) was slowly added while maintaining the temperature below −35° C. The solution was allowed to warm to −15° C. and then cooled to −50° C.

In a separate container, nickel acetylacetonate (0.036 moles, 9.25 g 5% molar ratio) and triphenylphosphine (0.145 moles, 38.0 g) were dissolved in 200 ml THF and cooled to −30° C. Diisobutylaluminum hydride (36.25 ml of 1M solution in THF) was added. 2-Bromobenzonitrile (0.725 moles, 131.95 g) was added to the solution. The solution was cooled to −50° C. The zinc chloride/phenyl lithium solution was added while maintaining the temperature below −50° C. The temperature was allowed to slowly warm to room temperature. The mixture was partitioned between ether and 250 ml 1N HCl The organic phase was washed with water, dried over sodium sulfate and concentrated to a reddish oil. 2-Cyanobiphenyl was purified by chromatography over silica gel columns eluted with hexane. (MS)

PREPARATION 2

2-Cyano-4-nitrobiphenyl

2-Cyanobiphenyl (0.111 moles, 20.0 g) and ammonium nitrate (10.0 grams) were added to 250 ml chloroform. Trifluoroacetic anhydride (80 ml) was added. The reaction mixture was stirred until the ammonium nitrate was dissolved. The reaction mixture was added to 300 ml of ice water. The organic layer was separated, dried over sodium sulfate, and concentrated in vacuo to yield 23.5 g of 2-Cyano-4nitrobiphenyl. (MS)

M. Pt.: 111–115° C. Calculated for $C_{13}H_8N_2O_2$: C, 69 64; H, 3.60; N, 12.49. Found: C, 69.45; H, 3.74 ; N, 12,26.

PREPARATION 3

4-Acetamino-2-cyanobiphenyl

2-Cyano-4-nitrobiphenyl (0.067 moles, 15.0 g.) was dissolved in 100 ml ethyl acetate/100 ml ethanol and hydrogenated at 40 psi over 3.0 g of 10% palladium on carbon. The catalyst was removed by filtering though celite. The solvents were removed in vacuo. The residue was dissolved in 175 ml of methylene chloride. Acetic anhydride (15 ml) was added. The reaction was stirred at room temperature for 30 minutes and poured over ice. The organic layer was dried, concentrated, and then purified by HPLC over silica gel eluted with a gradient of 0–10% ethyl acetate in chloroform. (MS)

M. Pt.: 173°–174.5° C. Calculated for $C_{15}H_{12}N_2O$: C, 76.15; H, 5.12; N, 11.85. Found: C, 76.12; H, 5.31; N, 11.82.

PREPARATION 4

4-(2-Cyanophenyl)-3-nitroaniline

4'-Acetamino-2-cyanobiphenyl (0.265 moles, 62.47 g.) was added at −15° to −20° C. to 600 ml of concentrated sulfuric acid. While maintaining the temperature below −15° C., nitric acid (0.278 moles, 17.5 g of 90%) in 200 ml of concentrated sulfuric acid was added dropwise. The reaction was stirred for 30 minutes following the addition and then for 3 hours at room temperature. The reaction was poured onto ice with vigorous stirring. The precipitate was filtered and dried. The solid was stirred in methanol (6 liters) and 2N sodium hydroxide (11 liters) for 6 hours, filtered and dried. The reaction produced 60 g of 4-(2-Cyanophenyl)-3-nitroaniline. (MS) (MS)

PREPARATION 5

2-(3,4-Diaminophenyl)benzonitrile 4-(2-Cyanophenyl)-2-nitroaniline (0.042 moles,10 g.) was dissolved in 200 ml ethanol and hydrogenated at 40 psi over 10 g of 10% Pd/C. The solution was filtered, concentrated, and purified by HPLC eluted with a gradient of 0–50% ethyl acetate in toluene. (MS)

Calculated for $C_{13}H_{11}N_3$: C, 74.62; H, 5.30; N, 20.08. Found: C, 74.50; H, 5.41; N, 19.52.

PREPARATION 6

5-(2-Cyanophenyl)benzimidazole 2-(3,4-Diaminophenyl)benzonitrile (0.04 moles, 8.3 g) was refluxed in 100 ml formic acid for 3 hours. The solution was concentrated in vacuo, triturated with toluene, and dissolved in water. The pH of the solution was adjusted to 7.5 with 2N sodium hydroxide. The intermediate was extracted with ethyl acetate. The organic layer was dried over sodium sulfate and concentrated in vacuo. The solid was triturated with 25% ethyl acetate/75% hexane, filtered and purified by HPLC on silica gel eluted with a gradient of 50–75% ethyl acetate in hexane. The reaction yielded 7.3 g of 5-(2-Cyanophenyl)benzimidazole. (MS)

calculated for $C_{14}H_9N_3$: C, 76.60; H, 4 14; N, 19.7. Found: C, 76.40; H 4.12; N 18.92.

PREPARATION 7

5-(2-Cyanophenyl)-1-triisopropylsilylindole sec-Butyllithium (41 mmole, 31.5 ml) was added dropwise over 10 minutes to 5-bromo-1-triisopropylsilylindole (40 mmoles, 14.0 g) in 400 ml THF at −78° C. The solution was stirred for 15 minutes. A solution of anhydrous $ZnCl_2$ in 50 ml THF was added. The solution was warmed to 0° C. and stirred for 40 minutes. In a separate flask nickel acetylacetonate (1.5 mmole, 0.385 g) and triphenylphosphine (6.0 mmoles, 1.60 g) were dissolved in 20 ml of THF and cooled to −78° C. DIBAL (1.5 mmole, 1.5 ml of 1.0M solution in hexane) was added. The solution was stirred for 10 minutes. 2-Bromobenzonitrile (39.9 mmoles, 7.26 g) was added. After stirring for 5 minutes, the indole solution was added over a 10 minute period. The mixture was allowed to warm to room temperature, stirred for 2 hours, and then added to ether and brine. The organic phase was dried over magnesium sulfate and concentrated in vacuo. The product was chromatographed over silica gel eluted with 0–15 % ether in hexane to yield 7.83 g of 5-(2-cyanophenyl)-1-triisopropylsilylindole. (MS)

Calculated for $C_{24}H_{30}N_2Si$: C, 76.95; H, 8.07; N, 7.48. Found: C, 76.60; H, 8.20; N, 7.69.

PREPARATION 8

5-(2-Cyanophenyl) indole

Tetra-n-butylammonium fluoride (8.0 mmoles, 8 ml of 1.0M solution in THF) was added to 5-(2-Cyanophenyl)-1-triisopropylsilylindole (4 mmole, 1.5 g) in 5 ml THF and stirred at room temperature for 5 minutes. The reaction was added to brine and extracted with ether. The ether solution was dried over sodium sulfate and concentrated. The residue was chromatographed over silica gel eluted with chloroform to yield 0.69 g of 5-(2-cyanophenyl) indole. (MS)

Calculated for $C_{15}H_{10}N_2$: C, 82.55: H, 4 62; N 12.84. Found: C , 82.26; H 4.76; N, 12.98.

PREPARATION 9

2-Carboxy-6-hydroxybenzenesulfonic acid

Methyl 2-hydroxy-3-methoxybenzoate (0.027 moles, 5.0 g) was added to a suspension of sodium hydride (0.03 moles, 1.45 g of 50% in mineral oil) in 50 ml DMF and stirred at room temperature for 1 hour. Dimethythiocarbamoyl chloride (0.03 moles, 3.73 g) in 40 ml DMF was added dropwise over 1 hour. The reaction was stirred for 18 hours. Ethyl acetate was added. The solution was thoroughly washed with brine, dried and condensed. The residue was purified by HPLC over silica gel eluted with 50% ethyl acetate in hexane to yield 0.9 g of 0-(2-carbomethoxy-6-methoxyphenyl)-N,N-dimethylthiocarbamate. (MS).

Calculated for $C_{12}H_{15}NO_4S$: C, 53.52; H, 5.61; N, 5.20. Found: C, 53.35; H, 5.54; N, 5.07.

O-(2-Carbomethoxy-6-methoxyphenyl)-N,N-dimethylthiocarbamate (720 mg) was heated at 220° C. for 100 minutes and cooled to yield 700 mg of S-(2-carbomethoxy-6-methoxyphenyl)-N,N-dimethylthiocarbamate. (MS)

Calculated for $C_{12}H_{15}NO_4S$: C, 53.52; H, 5.61; N, 5.20. Found: C, 53.74; H, 5.60; N, 4.92.

S-(2-carbomethoxy-6-methoxyphenyl)-N,N-dimethylthiocarbamate (14.4 mmoles, 3.9 g) was dissolved in 66 ml formic acid. Hydrogen peroxide (24 ml of 30%) was added dropwise with cooling when required. The reaction was stirred at room temperature for 16 hours and condensed. Toluene (100 ml) was added to the residue. The toluene solution was concentrated. The solid was slurried in ether and filtered to yield 3.0 g of 2-Carbomethoxy-6-methoxybenzenesulfonic acid dimethylamine salt.

2-Carbomethoxy-6-methoxybenzenesulfonic acid dimethylamine salt (9.0 mmoles, 2.6 g) was added dropwise at −20° C. to a solution of boron tribromide (27 mmoles, 3.8 ml) in 50 ml methylene chloride and stirred at −20° C. for 10 minutes and at room temperature overnight. The reaction was quenched with water. The pH was adjusted to 8.0 using 2N NaOH. The aqueous solution was washed with methylene chloride. The pH of the water layer was adjusted to 1.0 with 2N HCL. The intermediate was extracted with ethyl acetate and condensed. The solid triturated with ethyl acetate and filtered to yield 1.6 g of 2-carboxy-6-hydroxybenzenesulfonic acid.

PREPARATION 10

N-Carbobenzyloxy-4-trans-hydroxy-L-proline methyl ester.

A solution of silver oxide (I) (1.08 moles, 250 g) in 1500 ml acetone was cooled to −5°–0° C. N-carbobenzyloxy-4trans-hydroxy-L-proline (0.5 moles, 132.6 g) was added. The solution was stirred for 25 minutes. Methyl iodide (1.2 moles, 170.4 g) was added at −6° C. over 25 minutes. The reaction was stirred at room temperature for 5 hours, filtered, and concentrated. The intermediate was dissolved in ethyl acetate, filtered through silica gel and concentrated. (MS)

Calculated for $C_{14}H_{17}NO_5$: C, 60.21; H, 6.13; N, 5.01. Found: C, 60.40; H, 6.26; N, 5.06.

PREPARATION 11

N-Carbobenzyloxy-4-cis-phenoxy-L-proline methyl ester.

N-Carbobenzyloxy-4-trans-hydroxy-L-proline methyl ester (0.267 moles, 74.5 g), phenol (0.282 moles, 26.5 g), and triphenylphosphine (0.279 moles, 73.3 g) were dissolved in 750 ml of THF, and cooled to −3° C. Diethyl azidodicarboxylate (0.284 moles, 45 ml) was added dropwise over 2 hours. The reaction was stirred at room temperature overnight and then concentrated. The residue was dissolved in ether, filtered and concentrated. The intermediate was chromatographed over silica gel eluted with a gradient of 0–40% ethyl acetate in hexane to yield 41.0 g. (NMR)

Preparation 12

4-Bromo-t-butoxybenzene.

4-Bromophenol(57.8 moles, 10.0 g) was added to a −30° C. solution of isobutylene (40 ml) and methylene chloride (50 ml) and then cooled to -78° C. Trifluoromethanesulfonic acid (4 moles, 0.35 ml) was added. The mixture was held at −78° C. for 4 hours and then allowed to warm to room temperature. Triethylamine (0.5 ml) was added; the solvent was removed. The residue was chromatographed over silica gel eluted with 1% ethyl acetate in hexane to yield 12.4 g. (MS)

Calculated for $C_{10}H_{13}BrO$: C, 52.42; H, 5.72. Found: C, 52.69; H, 5.67.

PREPARATION 13

4-t-Butoxyphenol.

Sec-butyllithium (53.2 mmoles, 41 ml of 1.3M in hexane) was added dropwise at −78° C. to 4-bromo-t-butoxybenzene (53.2 mmoles, 12.2 g) in 200 ml THF, stirred at −78° C. for 1 hour, and added slowly to a solution of triisopropylborate (58.5 mmoles, 11.0g) in 50 ml THF while maintaining the temperature below −60° C. The mixture was allowed to warm gradually to −20° C. Chilled acetic acid (80 mmoles, 9.6 ml) was added. Hydrogen peroxide (58.5 mmoles, 5.9 ml of 30% diluted with 5 ml water) was added dropwise over 15 minutes while maintaining the temperature below 0° C. After stirring 10 minutes, the solution was washed with ammonium sulfate solution, dried, and concentrated. The residue was triturated with hexane and filtered to yield 4.2 g of 4-t-butoxyphenol. (MS).

Calculated for $C_{10}H_{14}O_2$: C, 72.26; H, 8.49. Found: C, 72.54; H, 8.27.

PREPARATION 14

Diethyl-(4-hydroxy)-phenethylphosphonate.

A solution of tetraethylmethylenediphosphonate (6.22 g, 21.6 mmol) in 30 mL of anhydrous THF at −30° C. under $N_2$ was treated with nBuLi (15.0 mL, 1.6M solution in hexanes) dropwise via syringe. The resulting solution was warmed to 0° C. for 30 min., and then cooled back to −30° C. 4-Benzyloxybenzaldehyde was then introduced via canula as a solution in 15 mL of anhydrous THF. After warming to room temperature and stirring for 2 hours, the reaction was quenched by pouring into $H_2O$ (200 mL). The aqueous was extracted with ethyl acetate (3×100 mL). The organic was dried ($Na_2SO_4$) and concentrated in vacuo to give an oil. The crude product was chromatographed ($SiO_2$, 25% hexane/ethyl acetate) to give 6.1 g (82%) of the α, B-unsaturated phosphonate as a light yellow oil that solidified on standing.

Calculated for $C_{19}H_{23}O_4P$: C, 65.89; H, 6.69. Found: C, 66.15; H, 6.59.

The phosphonate from the previous reaction (6.1 g, 17.5 mmol) was dissolved in 100 mL of absolute ethanol, and treated with 1.15 g of 5% Pd/C. The mixture was hydrogenated at 40 psi for 1 hour, and then passed through a pad of celite. The filtrate was concentrated in vacuo to yield 4.5 g (100%) of diethyl-(4-hydroxy)phenethylphosphonate as a light yellow oil.

PREPARATION 15

Diethyl-(4-hydroxy)-phenylphosphate.

4-Benzyloxyphenol (15.0 g, 75 mmol) was dissolved in 100 mL of anhydrous THF and cooled to 0° C. NaH (3.0 g, 75 mmol, 60% dispersion in mineral oil) was then introduced in small portions. When gas evolution ceased, diethylchlorophosphate was introduced dropwise via syringe. After stirring the reaction for 1 hour, the mixture was poured into $H_2O$ ethyl acetate (150 mL ea.). The layers were separated, and the organic washed with 0.1N NaOH (2×100 mL). The organic was dried $Na_2SO_4$) and concentrated in vacuo to a light yellow liquid. Chromatography ($SiO_2$, first 20% ethyl acetate/hexanes followed by 40% hexanes/ethyl acetate) provided 23.4 g (93%) of diethyl-(4-benzyloxy)-phenyl phosphate as a colorless liquid.

Diethyl-(4-benzyloxy)-phenyl phosphate (15.0 g, 44.7 mmol) was dissolved in 150 mL of 30% ethyl acetate in ethanol, along with 0.5 mL of concentrated HCl. To this solution was added 3.0 g of 10% Pd/C. The mixture was hydrogenated at 1 atm for 18 hours and then passed through a pad of celite to remove the catalyst. The filtrate was concentrated in vacuo, and the residue chromatographed ($SiO_2$, ethyl acetate) to provide 10.4 g (94%) of diethyl-4-hydroxy-phenyl phosphate as an amber liquid.

PREPARATION 16

Diethyl-(4-hydroxy)-benzenephosphonate

To a solution of 4-benzyloxybromobenzene (10.0 g, 38 mmol) in 150 mL of anhydrous THF at −78° C. under $N_2$ was added nBuLi (26.1 mL, 41.8 mmol, 1.6M in hexanes) dropwise over 30 minutes. After stirring for 15 minutes, diethylchlorophosphate (6.0 mL, 41.8 mmol) was added dropwise via syringe. The resulting mixture was allowed to gradually warm to room temperature whereupon the reaction was quenched by pouring into $H_2O$ ethyl acetate (200 mL ea.). The layers were separated, and the aqueous was extracted with ethyl acetate (2×100 mL). The organic was dried ($Na_2SO_4$), and concentrated in vacuo to a yellow liquid. Chromatography ($SiO_2$, 50–100% ethyl acetate/hexanes) provided 11.1 g (91%) of diethyl-(4-benzyloxy)-benzenephosphonate as a colorless liquid. MS.

Diethyl-(4-benzyloxy)-benzenephosphonate (11.0 g, 34 mmol) was hydrogenated as described in the previous example. Chromatography of the crude reduction product provided 4.3 g (52%) of diethyl-(4-hydroxy)benzenephosphonate as a light yellow liquid. MS.

PREPARATION 17

4-(pyrrolidinosulfonyl)-phenol

To a solution of pyrolidine (17 mL, 237 mmol) in 20 mL of $H_2O$ at room temperature was added p-flourobenzenesulfonyl chloride (15 g, 79 mmol) in portions over a 5 minute period. After 1 hour, the solution was diluted with 100 mL of $H_2O$ and extracted with ethyl acetate (3×50 mL). The organic was dried $Na_2SO_4$) and concentrated in vacuo to give 12.3 g (72%) of 4-(pyrrolidinosulfonyl)flourobenzene as a colorless oil that solidified on standing. This material was used in the following reaction without further purification. MS.

To a solution of benzyl alcohol (6.63 mL, 62.0 mmol) in 200 mL of anhydrous DMF at room temperature was added NaH (2.40 g, 60.0 mmol, 60% dispersion in mineral oil) in small portions. After stirring for 30 minutes, 4-(pyrrodlidinosulfonyl)-fluorobenzene (11.0 g, 51.2 mmol) was added over a 10 minute period. After 30 minutes, a white precipitate formed. The reaction was then diluted with 100 mL of $H_2O$, and the product isolated by vacuum filtration. The solid was dried in vacuo to give 14.85 g (95%) of the 4-(pyrrolidinosulfonyl)-phenylbenzylether as a white solid. MS.

A solution of 4-(pyrrolidinosulfonyl)phenylbenzylether (10.0 g, 33.1 mmol) was dissolved in 100 mL of absolute ethanol. This solution was treated with 2.5 g of 10% Pd/C. The mixture was hydrogenated at 40 psi for 2 hours. The catalyst was then removed by passing the reaction mixture through a pad of celite. The filtrate was concentrated in vacuo to provide 6.8 g (90%) of 4-(pyrrolidinosulfonyl)-phenol as a white solid. MS.

4-(methylaminosulfonyl)-phenol was prepared in a similar manner.

PREPARATION 18

N-(4-hydroxybenzamido)-L-proline methyl ester.

L-Proline methyl ester hydrochloride (7.2 g, 43.8 mmol) was dissolved in 100 mL of anhydrous DMF at 0° C. To this solution was added triethylamine (4.2 g, 43.8 mmol). After vigorous stirring for 1 hour, the solid triethylamine hydrochloride was removed by filtration. To the filtrate was added 4-benzyloxybenzoic acid (10.0 g, 43.8 mmol) followed by DCC (9.9 g, 48.2 mmol). The reaction mixture was allowed to stir overnight at room temperature. The solid DCU was then removed by filtration, and the filtrate distributed between $H_2O$/ethyl acetate 300 mL ea.). The organic was washed several times with 200 mL portions of $H_2O$ to remove DMF. The organic was dried ($Na_2SO_4$), and concentrated in vacuo to a solid residue that was chromatographed ($SiO_2$, 15–100% ethyl acetate/hexanes). Isolation provided 5.3 g (35%) of N-(4-benzyloxybenzamido)-L-proline methyl ester as a white solid. MS.

The above amide (10.0 g, 29.4 mmol) dissolved in 75 mL of absolute ethanol. To this solution was added 3 g of 10% Pd/C. The mixture was hydrogenated at 1 atm for 5 hours The catalyst was then removed by passing the reaction through a pad of celite. Concentration of the filtrate provided crude N-(4-hydroxybenzamido)-L-proline methyl ester that was purified by chromatography ($SiO_2$, 30% ethyl acetate/hexanes) to provide 6.3 g (86%) as a white solid. MS.

EXAMPLE 1

2-[5-(2-Carboxyphenyl) indol-1-yl]octanoic acid

5-Bromo-1-triisopropylsilylindole (25.6 mmoles, 9.0 g) was treated with sec-butyl lithium (37.8 mmoles, 27 ml of 1.4M solution in cyclohexane) and reacted with 4,4-dimethyl-2-(2-methoxy) phenyl-2-oxazoline (30.7 mmoles, 6.3 g) as in Example 2 to produce 1.72 g of 5-[2-(4,4-dimethyloxazolin-2-yl)phenyl]-1-triisopropylsilylindole. (MS)

5-[2-(4,4-Dimethyloxazolin-2-yl) phenyl ]-1-triisopropylsilylindole (1.48 mmoles, 661 mg) in 5 ml THF was treated at 0°C. with tetrabutylammonium fluoride (2.22 mmoles, 2.22 ml of 1.0N solution in THF). The solution was stirred for 3 hours, poured into 30 ml water, and extracted with ether. The organic layer was dried and concentrated. The oil was triturated with ether/hexane, and the solid was isolated by filtration. The reaction yielded 320 mg of 5-[2-(4,4-dimethyloxazolin-2yl)phenyl]indole. (MS)

Calculated for $C_{19}H_{18}N_2O$. 1.5 $H_2O$: C, 71.90; H, 6.69; N, 8.83. Found: C, 71.65; H, 6.72; N, 8.80.

Sodium hydride (0.54 mmoles, 22 mg of 60% in mineral oil) was added to 5-[2-(4,4-dimethyloxazolin-2-yl)phenyl] indole (0.43 mmoles, 125 mg) in 2 ml THF. After stirring 20 minutes, the solution was cooled to 0° C. Ethyl 2-bromooctanoate (0.54 mmoles, 0.135 mg) was added. The solution was stirred for 15 minutes, allowed to warm to room temperature, and stirred for 1.5 hours. The solution was poured into saturated ammonium chloride and extracted with ethyl acetate. The organic phase was dried and concentrated. The oil was chromatographed over silica gel eluted with 20% ether in hexane. The reaction yielded 172 mg of ethyl 2-[5-[2-(4,4-dimethyloxazolin-2-yl)phenyl]indol-1-yl] octanoate. (MS)

Calculated for $C_{29}H_{36}N_2O_3$: C, 75.62; H, 7.88; N, 6.08. Found: C, 75.74; H, 8.10; N, 6.37.

Ethyl 2-[5-[2-(4,4-dimethyloxazolin-2-yl)phenyl]indole-1-yl]octanoate (0.174 mmoles, 80 mg) was dissolved in 1 ml THF. Methyl iodide (0.15 ml, 1.1 mmole) was added. After stirring overnight at room temperature, the solution was concentrated. The residue was dissolved in 7 ml of 2:1 MeOH:2N NaOH and heated at 90° C. for 24 hours. The reaction was cooled to 0° C. and washed with ether. The pH was adjusted to 1.0 using 2N HCL. The product was extracted with 20% EtOH in ethyl acetate. The organic layer dried and concentrated to yield 35 mg of 2-[5-(2-Carboxyphenyl)indol-1-yl]octanoic acid that solidified upon standing. (MS)

M. Pt.: 115°–120° C.

Calculated for $C_{23}H_{25}NO_4$. 0.6 $H_2O$: C, 70.79; H, 6.77; N, 3.39. Found: C, 70.70; H, 6.67; N, 3.69.

EXAMPLE 2

2-[5-(2-Carboxy-3-hydroxyphenyl)indol-1-yl]octanoic acid.

5-Bromo-1-triisopropylsilylindole (0.089 moles, 30 g) was dissolved in THF and cooled to −78° C. Sec-butyl lithium (0.128 moles, 91.3 ml of 1.4M solution in cyclohexane) was added dropwise over 15 minutes. The reaction was stirred for 30 minutes at −60° C. 4,4-Dimethyl-2-(2-6-dimethoxyphenyl)-2-oxazoline (0.107 moles, 22 g.) in 100 ml THF was added dropwise. The reaction was allowed to warm to room temperature, stirred for 1 hour, cooled and quenched with a saturated ammonium chloride solution. The product was extracted into ether, dried over sodium sulfate, and concentrated. The residue was purified by HPLC over silica gel eluted with 25% ethyl acetate in hexane. The reaction yielded 5.65 g of 4,4-dimethyl-2-[2(1-triisopropylsilylindol-5-yl)-6-methoxyphenyl]-2-oxazoline. (MS).

4,4-dimethyl-2-[2-(1-triisopropylsilylindol-5-yl)-6methoxyphenyl]-2-oxazoline (8.5 g, 17.8 mmoles) was dissolved in 300 ml of THF. The solution was cooled to 0° C. Tetrabutylammonium fluoride (17.8 mmoles, 178 ml of 1M in THF) was added dropwise. The reaction was stirred at 0°–4° C. for 40 minutes, poured into ice water, and extracted into ether. The organic phase was dried over sodium sulfate, and the solvent was removed. The reaction produced 5.7 g of 4,4-dimethyl-2-[2-(indol-5-yl)-6-methoxyphenyl]-2-oxazoline. (MS)

4,4-Dimethyl-2-[2'-(1-Triisopropylsilylindol-5-yl)-6methoxy]phenyl- 2-oxazoline (5.7, 17.8 mmoles) was dissolved in 100 ml of THF and added dropwise to a suspension of sodium hydride (50 mmoles, 2.0 g of 60% in mineral oil) in 100 ml THF. The solution was stirred for 20 minutes at 0° C., allowed to warm to room temperature, and cooled to 0° C. Ethyl 2-bromooctanoate 19.6 mmoles, 4.92 g) in 50 ml of THF was added dropwise. The reaction was stirred at room temperature for 4 hours, poured into ice water, and extracted with ether. The organic phase was dried over sodium sulfate, concentrated, and chromatographed over silica gel eluted with diethyl ether. The reaction produced 4.0 g of ethyl 2-[5-[2-(4,4-dimethyloxazolin-2yl)-3-methoxyphenyl]indol-1-yl]octanoate. (MS)

Calculated for $C_{30}H_{38}N_2O_4$: C, 73.37; H, 7.70; N, 5.70. Found: C, 73.44, H, 7,81; N, 5.71.

Ethyl 2-[5-[2-(4,4-dimethyloxazolin-2-yl)-3-methoxyphenyl]indol1yl]octanoate (4.0 g, 8.2 mmoles) was dissolved in 200 ml acetone. Methyl iodide (25 ml) was added. The solution was refluxed for 18 hours. The solvent was removed. The resulting iodide was triturated with ether, filtered, dissolved in 50 ml methanol/50 ml 2N NaOH, and refluxed for 24 hours. The methanol was evaporated under vacuum. The residue was poured into water. The pH was adjusted to 3.0 with 1N HCl. The solid was filtered, washed with water, and dried. The intermediate was purified by HPLC over silica gel eluted with 20% ethanol in ethyl acetate. The reaction yielded 0.3 g of 2-[5-(2-carboxy-3-methoxyphenyl)indol-1yl]octanoic acid. (MS)

M. Pt.: 80°–90° C.

Calculated for $C_{24}H_{27}NO_5 \cdot 1.5\ H_2O$: C, 66.04; H, 6.92; N, 3.20 Found: C, 66.44; H, 6.64; N, 3.22.

2-[5-(2-Carboxy-3-methoxphenyl)indol-1-yl]octanoic acid (240 mg, 0.55 mmoles) was dissolved in 20 ml of methylene chloride. The solution was cooled to −78° C. $BBr_3$ (3.3 mmoles in 10 ml methylene chloride) was added dropwise. The solution was stirred at −78° C. for 10 minutes, allowed to warm to 0° C., and stirred for 1 hour. Water was slowly added. The product was extracted into methylene chloride. The organic phase was dried, concentrated and chromatographed over silica gel eluted with ethyl acetate. The reaction yielded 51 mg of 2-[5-(2-carboxy-3-hydroxyphenol)indol-1-yl]octanoic acid. (MS)

M Pt.: Dec. >230°. Calculated for $C_{23}H_{25}NO_5 \cdot \frac{1}{2} H_2O$: C, 68.30; H, 6.48; N, 3.46. Found: C 68.25; H 6.89; N, 3.64.

EXAMPLE 3

2-[5-[2-(2H-Tetrazol-5-yl)phenyl]-1H-benzimidazol-1-yl]octanoic acid

2-Bromooctanoic acid (0.076 moles, 16.9 g.) was dissolved in 100 ml of methylene chloride. Oxalyl chloride (0.197 moles, 25 g) was added to the solution. The reaction was stirred for 15 minutes. Two drops of DMF were added. The solution was stirred an additional 1 hour. The solvents were removed under vacuum. The resulting acid chloride was added dropwise to a solution of 2-(2-hydroxyethyl)pyridine (0.076 moles, 9.4 g) and triethylamine (0.08 moles, 11.2 ml) in 200 ml of methylene chloride. The reaction was stirred for 3 hours and concentrated. Ethyl acetate and water were added. The ethyl acetate solution was washed with saturated sodium bicarbonate and water, dried over sodium sulfate, and concentrated. The resulting oil, 2-bromooctanoic acid 2-pyridylethylester, was purified by HPLC on silica gel eluted with 25% ethyl acetate in hexane. (MS)

Calculated for $C_{15}H_{22}BrNO_2$: C, 54.87; H, 6.76; N, 4.27. Found: C, 53.47; H, 6.83: N, 3.91.

5-(2-Cyanophenyl)-1H-benzimidazole (0.027 moles, 6.0 g) was dissolved in 150 ml of DMF. Sodium hydride (0.0375 moles, 1.5 g of 60% in mineral oil) was added portionwise. The mixture was stirred for 1 hour. 2-Bromooctanoic acid 2-pyridylethylester (0.027 moles, 9.0 g) in 20 ml of DMF was added dropwise. After stirring 16 hours at room temperature, the solvent was removed under vacuum. Ethyl acetate and water were added. The organic layer was washed with brine and concentrated. The isomers were separated by HPLC on silica gel eluted with 3% EtOH in $CH_2Cl_2$. (MS)

2-[5-(2-Cyanophenyl)-1H-benzimidazol-1-yl]octanoic acid 2-pyridylethylester (0.042 moles, 19.6 g) was dissolved in 20 ml of methanol and 8 ml of 1N NaOH. The solution was stirred at room temperature for 3 hours. The reaction was concentrated under vacuum, dissolved in water, and washed with ether. The pH was adjusted to 3.0 with 5N HCl. The intermediate was extracted with ethyl acetate. The organic phase was washed with brine, dried over sodium sulfate, and concentrated. The reaction produced 13.0 g of 2-[5-(2-cyanophenyl)-1H-benzimidazol-1-yl]octanoic acid. (MS).

Calculated for $C_{22}H_{24}N_3O_2$: C, 73.11; H, 6.41; N, 11.63. Found: C, 73.40; H, 6.53; N, 11.64.

2-[5-(2-Cyanophenyl)1H-benzimidazol-1-yl]octanoic acid (0.032 moles, 11.5 g) was dissolved in 30 g of tributyltinazide. The solution was heated at 90° C. for 48 hours. An additional 10 g of tributyltinazide was added. The solution was heated for an additional 16 hours at 90° C. and allowed to cool. After cooling, acetonitrile, water, and acetic acid (200 ml of an 8:1:1 mixture) were added. The solution was washed three times with 1 liter of hexane. The acetonitrile layer was concentrated under vacuum. The residue was dissolved in ethyl acetate, washed with water, and dried. The ethyl acetate was evaporated. The residue was triturated with hexane and filtered to produce 9.9 g of 2-[5-[2-(2H-tetrazol-5-yl)phenyl]-1H-benzimidazol-1-yl]octanoic acid. (MS)

M Pt. 145°–150° C. Calculated $C_{22}H_{25}N_6O_2$: C, 65.33; H, 5.98; N, 20.78. Found: C, 65.52, H, 6.14; N, 20.50.

EXAMPLE 4

2-[5-[2-(2H-Tetrazol-5-yl)benzamido]-1H-benzimidazol-1-yl]octanoic acid

5-Nitrobenzimidazole (0.109 moles, 17.8 g.) was reacted with sodium hydride (0.122 moles, 4.9 g of 60% in mineral oil) and ethyl 2-bromooctanoate (0.102 moles, 22 ml) as in Example 11 to produce a mixture of the 5 and 6 isomer. The isomers were separated to yield 7.8 g of ethyl 2-(5-nitro-1H-benzimidazol-1-yl)octanoate.

Ethyl 2-(5-nitro-1H-benzimidazol-1-yl)octanoate (6.00 mmoles) was dissolved in ethanol and hydrogenated over 5% Pd/C and filtered over celite. The resulting amine was reacted with 2-(2H-tetrazol-5-yl)benzoic acid as in Example 10. The reaction produced 0.62 g of 2-[5-[2-(2H-tetrazol5yl)benzamido]1H-benzimidazol-1-yl]octanoic acid. (MS)

Calculated for $C_{23}H_{25}N_7O_3$: C, 61.73; H, 5.63; N, 21.91. Found: C, 61.71; H, 5.64; N, 21.90.

EXAMPLE 5

2-[5-[2-(2H-Tetrazol-5-yl)phenyl]-2-methyl-1H-benzimidazol-1-yl]octanoic acid 4-(2-Cyanophenyl)-2-nitroacetanilide (3.91 mmoles, 1.1 g) was dissolved in ethanol and hydrogenated over Pd/C (5%, 1.0 g). The catalyst was removed over a bed of celite. The solvent was removed in vacuo. The resulting 4-(2-cyanophenyl)-2-aminoacetanilide (3.58 moles, 0.9 g) was suspended in 25 ml glacial acetic acid. The reaction was heated to reflux for one hour, quenched with ice water, and layered with ethyl acetate. The pH was adjusted to 7.5 with 5N sodium hydroxide. The organic phase was washed with brine, dried over sodium sulfate, and concentrated. The reaction yielded 800 mg of 5-(2-cyanophenyl)-2-methyl-1H-benzimidazole. (MS)

M. Pt.: 205°–208° C. Calculated for $C_{15}H_{11}N_3$: C, 77.23; H, 4.75; N, 18.01. Found: C, 77.50; H, 4.87; N, 17.75.

5-(2-Cyanophenyl)-2-methylbenzimidazole (3.43 mmoles, 0.8 g) was dissolved in DMF. Sodium hydride (3.75 mmoles, 0.15 g.) was added. The solution was stirred for 30 minutes. Ethyl 2-bromooctanoate was added. The solution was stirred for 1 hour. Water and ethyl acetate were added; and the layers separated. The organic phase was washed with brine, dried over sodium sulfate and concentrated. The intermediate was chromatographed on silica gel eluted with 50% ethyl acetate in hexane to yield 1.0 g of ethyl 2-[5-[2-cyanophenyl]-2-methyl-1H-benzimidazol-1yl]octanoate. The nitrile was dissolved in 10 ml of tributyltinazide and heated at 70° C. for 3 days. The solution was stirred in a mixture of acetonitrile, water, and acetic acid (100 ml of 8:1:1)for 3 hours, washed with hexane (4×250 ml), and concentrated. The residue was dissolved in ethyl acetate, washed with water, dried over sodium sulfate and concentrated in vacuo. The intermediate was triturated with hexane, filtered and chromatographed over silica gel eluded with 10% ethanol in ethyl acetate with 1% acetic acid. The isomers were separated by reverse phase HPLC eluted with a gradient of 30–50% acetonitrile in water with 1% ammonium acetate. The intermediate was dissolved in ethanol (20 ml) and 5N NaOH (5 ml) and heated on a steam bath for 1 hour. The solution was concentrated to 75 ml. The pH was adjusted to 3.0 using 5N HCl. The precipitate was collected and dried. The reaction yielded 110 mg of 2-[5-[2-(2H-tetrazol-5yl)phenyl]2-methyl-1H-benzimidazol-1-yl]octanoic acid. (MS)

M. Pt.: Dec. >165° C. Calculated for $C_{23}H_{26}N_6O_2 \cdot 1.5 H_2O$: C, 62.01; H, 6.56; N, 18.86. Found: C, 62.23; H, 5.88; N, 18.41.

EXAMPLE 6

2-[5-[2-(2H-Tetrazol-5-yl)phenyl]-2-trifluoromethyl-1H-benzimidazol-1-yl-]octanoic acid 2-(3,4-Diaminophenyl)benzonitrile (0.01 moles, 2.09 g) was dissolved in 10 ml trifluoroacetic acid and heated at 85° C. for 16 hours. The solution was poured into water and extracted with ethyl acetate. The pH was adjusted to 3.0 using 5N NaOH. The ethyl acetate was washed with brine, dried over sodium sulfate, and concentrated. The residue was chromatographed on silica gel eluted with 25 % ethyl acetate in hexane. The reaction yielded 2.05 g of 5-(2-cyanophenyl)-2-trifluoromethyl-1H-benzimidazole. (MS)

5-(2-Cyanophenyl)-2-trifluoromethyl-1H-benzimidazole (7.0 mmoles, 2.0 g) was dissolved in 30 ml DMF. Sodium hydride (7.8 mmoles, 0.31 g of 60 % in mineral oil) was added portionwise. The reaction was stirred for 20 minutes. Ethyl 2-bromooctanoate (7.4 mmoles, 1.6 ml) was added. The reaction was stirred for 16 hours at 70° C. Additional ethyl 2-bromooctanoate (0.2 ml) was added. The reaction was stirred for 5 hours at 70° C., allowed to cool, poured into water, and extracted with ethyl acetate. The ethyl acetate solution was washed with brine, dried over sodium sulfate and concentrated. The residue was purified by HPLC over silica gel eluted with a gradient of 0–50% ethyl acetate in hexane. The 5 and 6 isomers were separated by reverse phase chromatography eluted with acetonitrile and water. The intermediate was dissolved in 10 ml tributyltinazide and heated at 90° C. for 36 hours. The solution was allowed to cool. Acetonitrile, water, and acetic acid (50 ml 8:1:1) were added. The acetonitrile mixture was washed with hexane (5×100 ml) and concentrated. The residue was dissolved in ethyl acetate, washed with brine, dried over sodium sulfate and concentrated. The material was dissolved in 25 ml ethanol/6 ml 5N NaOH and refluxed for 15 minutes. After cooling, the solvent was removed under vacuum. The residue was dissolved in water and washed three times with ethyl acetate. The pH of the aqueous phase was adjusted to 3.0 using 5N HCl. The oil was extracted with ethyl acetate. The organic layer was washed with brine, dried over sodium sulfate, and concentrated. The solid was triturated with hexane and filtered. The reaction produced 0.2 g of 2-[5-[2-(2H-tetrazol-5-yl)phenyl]-2-trifluoromethyl-1H-benzimidazol-1-yl]octanoic acid. (MS)

M. Pt.: 128°–130° C. Calculated for $C_{23}H_{23}F_3N_6O_2 \cdot \frac{1}{2} H_2O$: C, 57.38; H, 5.02; N, 17.46. Found: C, 57.10; H, 5.00; N, 17.06.

EXAMPLE 7

2-[5-[2-(2H-Tetrazol-5-yl)phenyl]-1H-benzimidazol-1-yl]heptanaoic acid 5-(2-Cyanophenyl)-1H-benzimidazole (4.56 moles, 1.0 g.) was reacted with sodium hydride (5.47 mmoles, 0.219 and ethyl 2-bromoheptanoate (6.84 mmoles, 1.62 g) as in Example 8 to produce 65 mg of 2-[5-[2-(2H-tetrazol-5-yl)phenyl]heptanoic acid. (MS).

M. Pt.: 123°–130° C. Calculated for $C_{21}H_{22}N_6O_2 \cdot \frac{1}{2} H_2O$; C, 63.14; H, 5.80; N, 21.04. Found: C, 62.96; H, 5.60; N, 20.75.

EXAMPLE 8

2-[5-[2-(2H-Tetrazol-5-yl)phenyl-1H-benzimidazol-1-yl]hexanoic acid 5-(2-Cyanophenyl)benzimidazole (1.36 mmoles, 299 mg) was dissolved in 1 ml DMF. Sodium hydride (1.63 mmoles, 0.5 mg) was added. The reaction was stirred at room temperature for 30 minutes. Ethyl 2-bromohexanoate (1.63 mmoles, 450 mg) in 0.5 ml DMF was added. The reaction was stirred for 16 hours. Water and ethyl acetate were added. The organic phase was washed with water, dried over sodium sulfate and concentrated. The residue was purified by chromatography over silica gel eluted with 70% diethyl ether in hexane to yield 380 mg of the intermediate. The intermediate was dissolved in tributyltinazide (1.0 g, 3.0 mmoles) and heated at 85° C. for 48 hours. The cooled reaction was treated with 2 ml 2N NaOH and washed with ether. The aqueous phase was acidified to pH 4 using 2N HCl. The resulting white precipitate was filtered and dried. The material was purified, and the isomers were separated by reverse phase HPLC. The reaction produced 56 mg of 2-[5-[2-(2H-tetrazol-5-yl)phenyl]-1H-benzimidazol-1yl]hexanoic acid. (MS)

Calculated for $C_{20}H_{20}N_6O_2 \cdot \frac{1}{4}$ HOAc: C, 62.90; H, 5.40; N, 21.47. Found: C, 63.09; H, 5.45; N, 21.20.

EXAMPLE 9

1-[1-Oxo-2-[5-[2-(2H-tetrazol-5-yl)phenyl]-1H-benzimidazole-1-yl]octyl]-L-proline.

L-proline benzyl ester hydrochloride (0.745 moles, 180 mg) and diisopropylethyl amine (0.745 moles, 0.13 ml) were dissolved in 50 ml DMF. The solution was stirred at room temperature for 20 minutes. 1-Hydroxybenzotriazole (0.745 moles, 100 mg), 2-[5-[2-(2H-tetrazol-5yl)phenyl]benzimidazol-1-yl]octanoic acid (0.745 moles, 300 mg) and dicyclohexylcarbodiimide (0.745 mmoles, 153 mg) were added sequentially. The reaction was stirred at room temperature for 12 days and poured into water. Ethyl acetate was added, washed with brine, dried over sodium sulfate, concentrated and purified by chromatography over silica gel eluted with ethyl acetate. The reaction yielded 250 mg of benzyl 1-[1-oxo-2-[5-[2-(2H-tetrazol-5yl)phenyl]-1H-benzimidazole-1-yl]octyl]-L-proline benzyl ester. (MS)

Benzyl 1-[1-oxo-2-[5-[2-(2H-tetrazol-5-yl)phenyl]-1H-benzimidazole-1-yl]octyl ]-2-pyrrolidinecarboxytate (0.388 moles, 230 mg) was dissolved in 5.0 ml methanol/3.0 ml 2N NaOH and stirred at room temperature for 16 hours. The ethanol was removed in vacuo. The aqueous layer washed with ether. The pH was adjusted to 3.5 using 2N HCl with cooling. The precipitate was filtered and dried to yield 75 mg of 1-[1-Oxo-2-[5-[2-(2H-tetrazol-5-yl)phenyl]-1H-benzimidazole-1-yl]octyl]-L-proline. (MS)

M. Pt.: 145°–150° C. Calculated for $C_{27}H_{31}N_7O_3$: C, 64.65; H, 6.23; N, 19.55. Found: C, 64.41; H, 6 25; N 19.25.

EXAMPLE 10

2-[4-[2-(2H-Tetrazol-5-yl)benzamido]-1H-benzimidazol-1-yl]octanoic acid

3-Nitro-1,2-phenylenediamine (0.065 moles, 10.2 g) was added to 200 ml formic acid and heated to reflux for 3 hours. The solution was cooled and then concentrated under vacuum. The residue was dissolved in water. The pH was adjusted to 8.3 using 5N sodium hydroxide. The intermediate was extracted with ethyl acetate. The organic phase was washed with brine, dried over sodium sulfate and concentrated to yield 7.0 g of 4-nitrobenzimidazole. (MS)

M. Pt.: 248°–249° C. Calculated for $C_7H_5N_3O_2$: C, 51.54; H, 3.09; N, 25.76. Found: C, 51.60; H, 3,17; N, 25.57.

4-Nitrobenzimidazole (41.7 mmoles, 6.8 g) was dissolved in 200 ml DMF. Sodium hydride (47.5 mmoles, 1.9 g of 60% in mineral oil) was added portionwise. The reaction was stirred for 30 minutes. Ethyl 2-bromooctanoate was added. The reaction stirred at room temperature for 3 hours and concentrated. Ethyl acetate and water were added; and the layers separated. The organic layer was washed with brine, dried over sodium sulfate and concentrated. The intermediate was purified by HPLC over silica gel eluted with a gradient of 0–50% ethyl acetate in hexane. The reaction yielded 10.3 g of ethyl 2-(4-nitro-1H-benzimidazol-1-yl) octanoate. (MS)

M. Pt.: 86°–89° C. Calculated for $C_{17}H_{23}N_3O_4$: C, 61.25; H, 6.95; N, 12.60. Found: C, 61.52; H, 7.06; N, 12.21.

Methyl 2-cyanobenzoate (0.124 moles, 20.0 g) was dissolved in 55 g tributyltinazide and heated at 85° C. for 72 hours. The solution was allowed to cool. Methanol (200 mi) and water (50 mi) were added. The solution was stirred for 1hour. Ethyl acetate and brine were added. The organic layer was dried and evaporated. The residue was triturated 3 times with large volumes of hexane, dissolved in chloroform, and precipitated with hexane. The precipitate was filtered to yield 10.0 g of ethyl 2-(2H-tetrazol-5-yl)benzoate. The ester (6.8 moles, 1.4 g) was dissolved in 5 ml ethanol and 10 ml of 2N NaOH added and heated on a steam bath for 1 hour. The solvent was removed under vacuum. The residue was dissolved in water. The pH was adjusted to 2.0 using 2N HCl. The intermediate was extracted with ethyl acetate to yield 0.8 g of 2-(2-H-tetrazol-5-yl)benzoic acid.

Ethyl 2-(4-nitro-1H-benzimidazol-1-yl)octanoate (4.44 moles, 1.48 g.) was hydrogenated over 0.6 g of 5% Pd/C in 100 ml ethanol. The catalyst was filtered over celite. The solution was concentrated. The residue was dissolved in 25 ml DMF and added to a stirred mixture of 2-(2H-tetrazol-5-yl)benzoic acid (4.21 mmoles, 0.80 g), dicyclohexylcarbodiimide (4.31 mmoles, 0.89 g.), and hydroxybenzotriazole (4.44 mmoles, 0.60 g) in 50 mi DMF. The reaction was stirred for 4 hours. The solid was removed by filtration. The reaction was concentrated. The residue was dissolved in ethyl acetate, and washed with water. The pH was adjusted to 8.0 using 5N NaOH. The aqueous layer was acidified to pH 2.5 using 2N HCL, and then extracted with ethyl acetate. The organic phase was separated, washed with water, dried and concentrated. The product was purified over silica gel eluted with 2% EtOH in ethyl acetate with 1% acetic acid to yield 0.18 g of 2-[4-[2-(2H-tetrazol-5-yl)benzamido]-1H-benzimidazol-1-yl]octanoic acid. (MS)

M. Pt.: 130°–134° C.

Calculated for $C_{22}H_{25}N_7O_3$: C, 61.73; H, 5.63; N, 21.91. Found: C, 61.86; H, 5.74; N, 22.15.

EXAMPLE 11

4-Butoxy-2-[5(and6)-[2-(2H-tetrazol-5-yl)phenyl]-1H-benzimidazol-1-yl]-butanoic acid Ethyl acetoacetate (0.14 moles, 18.2 g.) was added dropwise to a stirred mixture of sodium hydride (0.14 moles, 5.6 g of 60% in mineral oil) in 500 ml of DMF. 2-Butoxyethyl bromide (0.138 moles, 25 g) was added dropwise. The solution was stirred at room temperature for 2 hours, refluxed for 2 hours, poured onto ice. The intermediate was extracted with ethyl acetate. The ethyl acetate solution was washed with water three times, dried over sodium sulfate and concentrated. The intermediate was purified by HPLC on silica gel eluted with 25% ethyl acetate in hexane to yield 11.6 g of ethyl 2-aceto-4-butoxybutanoate. (MS).

Calculated for $C_{12}H_{22}O_4$: C, 62.58; H, 9.63. Found: C, 62.38; H, 9.55.

Sodium (0.05 moles, 1.2 g.) was dissolved in 200 ml methanol and cooled to −35° C. Ethyl 2-aceto-4-butoxybutanoate (0.048 moles, 11.0 g.) in 20 ml. methanol was added dropwise. N-Bromosuccinimde (0.06 moles, 10.7 g.) was added portionwise while cooling. The reaction was allowed to warm to room temperature and stirred for 16 hours. Water (200 ml) was added dropwise. The mixture was extracted into ethyl acetate and washed with water. The ethyl acetate was dried and concentrated. The intermediate was distilled on a Kugelrohr to yield 2.72 g of methyl 2-bromo-4-butoxybutanoate. (MS)

5-(2-Cyanophenyl)-1H-benzimidazole (7.0 mmoles, 1.5 g.) was dissolved in 50 ml. of DMF. Sodium hydride (8.0 mmoles, 0.33 g. of 60% in mineral oil) was added portionwise. The solution was stirred for 30 minutes. Methyl 2-bromo-4-butoxybutanoate (11.0 moles, 2.72 g) was added dropwise. The solution was stirred for 16 hours at room temperature. The mixture was poured into ice water and extracted with ethyl acetate. The organic phase was washed three times with water, dried over sodium sulfate, and concentrated. The intermediate was purified by HPLC over silica gel eluted with a gradient of 50–100% ethyl acetate in hexane to yield 1.6 g of methyl 4-butoxy-2-[5(and 6)-(2-cyanophenyl)-1H-benzimidazol-1-yl]butanoate. (MS )

Calculated for $C_{21}H_{25}N_3O_3$: C, 70.57; H, 6.44, N, 10.73. Found: C, 70.44; H, 6.40; N, 10.61.

Methyl 4-butoxy-2-[5(and 6)-(2-cyanophenyl)-1H-benzimidazol-1-yl]butanoate (4.0 mmoles, 1.6 g) was dissolved in 25 ml methanol and 5.5 ml 2N NaOH. The solution was stirred at room temperature for 3 hours. The solution was concentrated. The residue was dissolved in water and extracted with ether. The pH of the aqueous layer was adjusted to 3.0 using 2N HCL. The intermediate was extracted with ethyl acetate. The ethyl acetate was dried over sodium sulfate, concentrated, and purified by HPLC over silica gel eluted with 50% ethyl acetate in hexane to yield 1.4 g of 4-butoxy-2-[5(and 6)-(2-cyanophenyl)-1H-benzimidazol-1-yl] butanoic acid.

4-Butoxy-2-[5(and 6)-(2-cyanophenyl)-1H-benzimidazol1-yl]butanoic acid (2.5 mmoles, 950 mg.) was dissolved in 2 g tributyltinazide and heated at 90° C. for 48 hours. The reaction was cooled and washed with 50 ml hexane. The residue was concentrated in vacuo, triturated with ether and filtered. The reaction yielded a 1:1 mixture of the 5 and 6 isomers of 4-butoxy-2-[5(and6)-[2-(2H-tetrazol-5-yl)phenyl]-1H-benzimidazol-1-yl]butanoic acid (NMR)

EXAMPLE 12

2-[1-[5-[2-(2H-Tetrazol-5-yl)phenyl]-1H-benzimidazol-1-yl]hexyl]-1H-imidazole-1-acetic acid.

2-[1-(1-Hydroxy)hexyl]-1-tritylimidazole (17.8 moles, 7.3 g) and dropwise diisopropylethylamine (0.018 moles, 18.0 mmoles) in methylene chloride were added to methanesulfonic anhydride (18 moles, 3.13 g) in 300 ml methylene chloride at −55° to −60° C. 5-(2-Cyanophenyl)-1H-benzimidazole (17.8 moles, 3.9 g.) was added dropwise with the temperature maintained below −55° C. The solution was stirred for 3 hours, then warmed to room temperature, and stirred for 3 days. Water was added. The intermediate was extracted with dichloromethane. The organic phase was washed with water, dried over sodium sulfate, and concentrated. The residue was purified by HPLC over silica gel eluted with a gradient of 50–100% ethyl acetate in hexane. The reaction yielded 2.1 g of 2-[1-[5-(2-cyanophenyl)-1H-benzimidazol-1-yl]hexyl]-1H-imidazole. (MS)

Calculated for $C_{42}H_{37}N_5$: C, 82.46; H, 6.10; N, 11.45. Found: C, 82.20; H, 6.33; N, 11.69.

2-[1-[5-(2-Cyanophenyl)-1H-benzimidazol-1-yl]hexyl]-1-trityl-1H-imidazole (3.44 moles, 2.1 g) was dissolved in 200 ml ether, 240 ml formic acid, and 24 drops of water. The solution was stirred for 1 hour at room temperature and concentrated. Ethyl acetate was added. The ethyl acetate solution was washed with water, dried over sodium sulfate, filtered and concentrated. The residue was dissolved in 50 ml DMF. Sodium hydride (3.8 moles, 152 mg of 60% in mineral oil) was added. The reaction was stirred at room temperature for 2 hours. Ethyl bromoacetate (3.8 moles, 0.634 g.) in 50 ml DMF was added. The reaction was stirred for 1 hour, poured into ice water, and extracted with ethyl acetate. The organic solution was washed with brine, dried over sodium sulfate, and concentrated. The intermediate was purified by chromatography over silica gel eluted with ethyl acetate to give 830 mg of ethyl 2-[1-[5-[2-(2-cyanophenyl-1H-benzimidazol-1-yl]hexyl]-1H-imidazole-1acetate. (MS)

The ester was dissolved in 20 ml ethanol and 40 ml of 2N NaOH and stirred at room temperature overnight. The solution was concentrated. The residue was dissolved in water and washed with ether. The pH was adjusted to 3.5 using 2N HCl. The precipitate was dissolved in ethyl acetate, washed with water, dried over sodium sulfate and concentrated to yield 770 mg of 2-[1-[5-(2-cyanophenyl)-1H-benzimidazol-1-yl]hexyl]-1H-imidazole-1-acetic acid. (MS)

The nitrile was dissolved in 2.0 g of tributyltinazide and heated at 95° C. for 2 days. The solution was allowed to cool. Acetonitrile, water, and acetic acid (40 ml of 8:1:1) were added. The solution was washed with hexane and concentrated. The product was extracted with ethyl acetate. The ethyl acetate solution was washed with water, dried over sodium sulfate, and concentrated. The product was purified by HPLC eluted with a gradient of acetonitrile in water with 1% acetic acid. The reaction yielded 63 mg of 2-[1-[5-[2-(2H-tetrazol-5-yl)phenyl]-1H-benzimidazol-1yl]hexyl]-1H-imidazole-1-acetic acid. (MS)

M. Pt.: 150°–160° C. Calculated for $C_{25}H_{26}N_8O_2$. HOAc: C, 61.12; H,5.70; N, 21.12. Found:

C 60.26; H, 5.80; N 21.17.

EXAMPLE 13

1-[oxo-2-[5-[2-(2H-tetrazol-5-yl)phenyl]-1H-benzimidazole-1-yl]octyl]-4-hydroxyl-L-proline.

The N-carbobenzyloxy-4-hydroxy-L-proline lactone (4.04 mmoles, 1.0 g) was prepared according to the procedure in Heterocycles 20: 823 (1983). The lactone was deprotected by dissolving the lactone in 10 ml dioxane and passing HBr gas through the solution for 30 minutes. The white precipitate was filtered and dried to yield 153 mg of 4hydroxy-L-proline lactone hydrobromide. (MS)

M. Pt.: 197°–200° C. Calculated for $C_5H_8NO_2Br$: C, 30.95; H, 4.16; N, 7.22. Found: C, 31.75; H, 4.16; N, 6.98.

4-Hydroxy-L-proline lactone hydrobromide (0.74 mmoles, 143 rag) and 2-[5-(2-tetrazol-5-ylphenyl)benzimidazol-1-yl]octanoic acid (0.74 mmoles, 300 mg) were dissolved in 30 ml DMF and cooled to 0° C. N,N-Diisopropylethylamine (0.74 mmoles, 0.15 ml) was added. The solution was stirred for 10 minutes. Hydroxybenzotriazole (0.74 mmoles, 100 mg) and then dicyclohexylcarbodiimide (0.74 mmoles, 153 mg) were added. The solution was stirred at room temperature for 3 days. The intermediate was extracted in ethyl acetate. The ethyl acetate solution was washed with water, dried over sodium sulfate, concentrated. The residue was chromatographed over silica gel eluted with 10% methanol in ethyl acetate. The reaction yielded 200 mg of 1-[1-oxo-2-[5-[2-(2H-tetrazol-5-yl)phenyl]-1H-benzimidazol-1-yl]octyl]-4-hydroxy-L-proline lactone. (MS). The lactone was dissolved in 2.0 ml methanol/2.0 ml 2N NaOH and stirred at room temperature for 16 hours The solvent was removed in vacuo. Water was added. The solution was extracted with ether. The pH of the aqueous layer was adjusted to 3.2 using 2N HCl. The precipitate was filtered, washed with water, and dried to yield 37 mg. The aqueous phase was extracted with ethyl acetate, dried and concentrated to yield an additional 60 mg of 1-[1-oxo-2-[5-[2-(2H-tetrazol-5-yl)phenyl]-1H-benzimidazole-1-yl]octyl]-4-hydroxy-L proline. (MS)

M. Pt.: 155°–160° C. Calculated for $C_{27}H_{31}N_7O_4$: C, 62.66; H, 6.04; N, 18.94. Found: C 62.91; H, 6.16; n,18.67.

EXAMPLE 14

1-Methyl-2-[1-[5-[2-(2H-Tetrazol-5-yl)phenyl)-1H-benzimidazol-1yl]heptyl]-1H-imidazole n-Butyllithium (26.8 moles, 16.8 ml of 1.6M solution in hexane) was added at −78° C. to N-methyl-1H-imidazole (25.6 mmoles, 2.0 g) in 20 ml THF. The solution was warmed to −35° C. for 10 minutes and then cooled to −78° C. 1-Heptanol (26.8 mmoles, 3.0 g) in 15 ml THF was added dropwise over 15 minutes. The reaction was stirred at 0° C. for 1 hour, poured into saturated ammonium chloride, extracted with ethyl acetate, and concentrated to yield 4.3 g of the alcohol. The alcohol (15.6 mmoles, 3.0 g) was dissolved in 10 ml THF and cooled to 0° C. Thionyl chloride (15.6 mmoles, 1.84 g.) was added dropwise. After 10 minutes, the solution was concentrated to yield 2-[1-(1-Chloro)heptyl]-1-methyl-1H-imidazole hydrochloride. (NMR)

Sodium hydride (5.0 moles, 200 mg of 60% in mineral oil) was added at 0° C. to 5-(2-cyanophenyl)-1H-benzimidazole (2.28 moles, 0.50 g) in 3 ml DMF. The reaction was stirred for 15 minutes, and allowed to warm to room temperature. 2-[1-(1-Chloroheptyl]-1-methyl-1H-imidazole hydrochloride (2.30 mmoles, 0.57 g) was added portionwise over 15 minutes. The solution was stirred for 24 hours. The intermediate was extracted with ethyl acetate. The ethyl acetate solution was washed with brine, dried and concentrated in vacuo. The intermediate was chromatographed over silica gel eluted with 10% hexane in ethyl acetate to yield 320 mg of 1-methyl-2-[1-[5-(2-cyanophenyl)-1H-benzimidazole-1-yl]heptyl]-1H-imidazole. The intermediate was a 1:1 mixture of regioisomers. (MS)

1-Methyl-2-[1-[5-(2-Cyanophenyl)-1H-benzimidazole-1-yl]heptyl]-1H-imidazole (0.79 mmoles, 315 mg) was heated in 0.750 g of tributyltinazide at 85° C. for 3 days. 2N NaOH (5 ml) was added. The solution was stirred for 30 minutes and extracted twice with ether. The pH of the aqueous layer was adjusted co 4.0 using 2N HCl. The precipitate was filtered. The pure 5 regioisomer was obtained after purification by HPLC over reverse phase columns to yield 20 mg of 1-methyl-2-[1-[5-[2-(2H-tetrazol-5-yl)phenyl)-1H-benzimidazol-1-yl]heptyl]-1H-imidazole. (MS)

M. Pt.: 88°–93° C.

EXAMPLE 15

1-[1-oxo-2-[5-[2-(2H-tetrazole-5-yl)phenyl]-1H-benzimidazol-1-yl]octyl]-4-cis-methoxy-L-proline.

N-Carbobenzyloxy-4-hydroxy-L-proline lactone (17.2 mmoles, 4.24 g) was dissolved in 5 ml methanol, cooled to 0° C., treated with 10 ml of 2N NaOH, and stirred at room temperature for 3 hours. The reaction was acidified to pH 3.5 using 2N HCl. The intermediate was extracted with ethyl acetate. The solution was dried over sodium sulfate and concentrated. The intermediate acid was dissolved in acetone (26 ml). Silver (I) oxide (48.2 mmoles, 11.34 g) and methyl iodide (55.5 mmoles, 12.3 ml) were added. The solution was stirred for 40 hours, filtered, concentrated and chromatographed over silica gel eluted with 30% ethyl acetate in hexane to yield 2.87 g of N-carbobenzyloxy-4-cis-methoxy L-proline methyl ester. (MS)

N-carbobenzyloxy-4-cis-methoxy-L-proline methyl ester (5.70 moles, 1.68 g) was hydrogenated at 40 psi in 50 ml ethyl acetate over 0.5 g of 10% Pd/C. The solution was filtered, concentrated to yield 835 mg of 4-cis-methoxy L-proline methyl ester. The amine (1.23 mmoles, 196 mg) was dissolved in a solution of 2-[5-[2-(2H-tetrazol-5yl)phenyl]-1H-benzimidazol-1-yl]octanoic acid (1.23 mmoles, 500 mg) in DMF. 1-Hydroxybenzo-triazole (170 mg) and dicyclohexyl-carbodiimide were added. The solution was stirred for 48 hours at room temperature. The solution was filtered. The solvent was removed in vacuo. The residue was chromatographed over silica gel eluted with 0–50% ethanol in ethyl acetate. The resulting ester was dissolved in 2.0 ml methanol and 3.0 ml 2N HCl and stirred for 3 hours. The solvent was removed. The residue was poured into ice and extracted into ethyl acetate. The ethyl acetate solution was filtered and concentrated. The reaction yielded 170 mg of 1-[1-oxo-2-[5-[2-(2H-tetrazole-5-yl)phenyl]-1H-benzimidazol-1-yl]octyl]-4-cis-methoxy-L-proline. (MS)

Calculated for $C_{28}H_{33}N_{7O4}$: C, 63.26; H, 6.23; N, 18.44. Found: C, 60.13; H, 6.71; N, 16.20.

EXAMPLE 16

2-[5-[2-(3H-Tetrazol-5-yl)phenyl]-1H-benzimidazol-1-yl]nonynoic acid.

Sodium hydride (0.10 mole, 4.0 g. of 60% in mineral oil) was added portionwise to a stirred solution of ethyl acetoacetate (0.10 mole, 13.0 g) in 100 ml DMF. The solution was stirred at room temperature for 30 minutes. Potassium iodide (50 mg) was added dropwise. 1-Chloro-3-heptyne (0.11 mole, 14.6 g) was added dropwise over 30 minutes. The solution was stirred at room temperature for 24 hours and at 50° C. for 24 hours. The solution was concentrated. Ethyl acetate and water was added. The organic phase was separated, washed three times with brine, dried over sodium sulfate and concentrated. The intermediate was purified by HPLC over silica gel eluted with a gradient of 0–30% ethyl acetate in hexane to yield 8.3 g of ethyl 6-(2-acetyl-)nonynoate (NMR)

Ethyl 6-(2-acetyl)nonynoate (37 moles, 8.3 g) was added to a solution of sodium (37 mmoles, 0.85 g.) in 80 ml methanol. The solution was cooled to −35° C. bromosuccinimide 37 mmoles, 6.76 g) was added portionwise. After stirring for 4 hours at room temperature, 100 ml of water was added. The intermediate was extracted with ether. The organic phase was dried and concentrated. The intermediate was purified by HPLC over silica gel eluted with a gradient of 0–50 % ethyl acetate in hexane to yield 5.0 g of methyl 6-(2-bromo)nonynoate. (MS)

5-(2-Cyanophenyl)benzimidazole (7.1 mmoles, 1.55 was dissolved in 70 ml DMF. Sodium hydride (7.1 mmoles, 0.284 g of 60 % in mineral oil) was added portionwise. The solution was stirred for 30 minutes. Methyl 6-(2-bromo)nonynoate (7.8 mmoles, 2.0 g) was added dropwise. The solution stirred at room temperature for 2 hours. Water was added. Methyl 2-[5(and 6)-(2-cyanophenyl)- 1H-benzimidazol-1-yl]nonynoate was extracted with ethyl acetate, washed with water, dried over sodium sulfate, and concentrated. (MS)

Methyl 2-[5(and 6)-(2-cyanophenyl )-1H-benzimidazole-1 -yl]nonynoate (7.1 mmoles,2.7 g.) was dissolved in tributyltinazide (21 mmoles, 7.0 g) and heated at 85° for 3 days. The solution was allowed to cool. Acetonitrile, water and acetic acid (100 ml of 8:1:1) were added. The solution was stirred for 30 minutes, washed twice with hexane and concentrated. The residue was dissolved in ethyl acetate, dried, concentrated and purified by HPLC on silica gel eluted with 5% ethanol in methylene chloride with 1% acetic acid to yield 1.6 g of ester. The ester was dissolved in 50 ml methanol and 100 ml 2N NaOH and stirred at room temperature for 3 hours. The reaction was concentrated. Water was added. The pH was adjusted to 3.0 using 2N HCl. The precipitate was filtered and dried to yield 1.2 g of a mixture of the isomers. The isomers were separated by HPLC on reverse phase chromatography eluted with 50% methanol in water with 0.5% sodium acetate. 2-[5-[2-(2H-Tetrazol-5-yl)phenyl]-1H-benzimidazol-1-yl]nonynoic acid. (MS)

Calculated for $C_{23}H_{22}N_6O_2 \cdot H_2O$: C, 63.93; H, 5.55; N, 19.44. Found: C, 63.69, H, 5.36; N, 19.25.

EXAMPLE 17

1-[1Oxo-2-[5-[2-(2H-tetrazol-5-yl)phenyl]-1H-benzimidazol-1yl]octyl]-2-pyrrolidineacetic acid.

N-Carbobenzyloxy-L-proline (0.048 moles, 12.0 g) was dissolved in 50 ml THF and cooled to 0° C. Borane-methyl sulfide complex (0.05 moles, 25 ml of 2M in THF) was added dropwise. The reaction was stirred for 16 hours at room temperature and then cooled to 0° C. water (50 ml) was added dropwise. The solution was filtered. The solid was washed with ethyl acetate. The organic solutions were combined, washed with water, dried over sodium sulfate and concentrated to yield 10.3 g of N-carbobenzyloxy-2-hydroxymethyl pyrrolidine. N-carbobenzyloxy-2-hydroxymethyl pyrrolidine (0.038 moles, 9.0 g) and triethylamine (0.076 mole) were dissolved in 150 ml of chloroform. Tosyl chloride (0.0475 moles, 9.05 g) was added portionwise followed by dimethylaminopyridine (200 mg). The solution was stirred overnight at room temperature. Chloroform was added. The solution was washed with water, dried over sodium sulfate, and concentrated. The resulting tosylate (0.0385 moles, 15.0 g) and sodium cyanide (0.048 moles, 2.35 g) were dissolved in 150 ml DMSO. The reaction was heated to reflux until completion as measured by thin layer chromatography. The reaction was cooled; water was added. The intermediate was extracted with ethyl acetate and concentrated to yield 9.56 g of 2-pyrrolidineacetonitrile. The nitrile was hydrolyzed by dissolving in 150 ml ethanolic HCl and slowing adding water to the solution. The solution was then concentrated in vacuo. Ethyl acetate and sodium bicarbonate were added. The ethyl acetate solution was concentrated. The residue dissolved in ethyl acetate, filtered and concentrated. The resulting acetate was chromatographed on silica gel eluted with a gradient of 5.0–100% ethyl acetate in hexane followed by a gradient of 0–20% ethanol in ethyl acetate to yield 4.35 g of ethyl 2-pyrrolidineacetate. (MS)

2-[5-]2-(2H-Tetrazol-5yl)phenyl]-1H-benzimidazol-1-yl]octanoic acid {(0.74 mmoles, 300 mg), ethyl 2-pyrrolidineacetate 0.74 mmoles, 116 mg) and hydroxy benzotriazole (0.74 mmoles 100 mg) were dissolved in 5.0 ml DMF. Dicyclohexylcarbodiimide (0.74 mmoles, 152 mg) was added. The reaction was purified and hydrolyzed as in Example 48. The reaction produced 50 mg of 1-[1-oxo-2-[5-[2-(2H-tetrazol-5-yl)phenyl]-1H-benzimidazol-1-yl]octyl]-2-pyrrolidineacetic acid. (MS)

M. Pt.: 122°–125° C. Calculated for $C_{28}H_{33}N_7O_3$: C, 65.23; H, 6.45; N, 19.02. Found: C, 65.27; H, 6.42; N, 18.82.

EXAMPLE 18

1-[1-Oxo-2-[5-[2-(2H-tetrazol-5-yl)phenyl]-1H-benzimidazol-1-yl]octyl]-4-trans-hydroxy-L-proline.

Methyl N-carbobenzyloxy-4-trans-hydroxy-L-proline ester (0.0286 moles, 8.0 g), trimethylacetyl chloride (0.0315 moles, 3.87 ml), triethyl amine (0.0315 moles, 4.38 ml) and dimethylaminopyridine (350 mg) were dissolved in 100 ml of THF and stirred at room temperature for 16 hours. The pH was adjusted to 2.5 with 0.2N HCl. The intermediate was extracted with ethyl acetate. The organic phase was washed with water, dried over sodium sulfate and concentrated. The resulting oil (17 mmoles, 6.3 g) was dissolved in ethyl acetate (75 ml) with p-toluenesulfonic acid (17 mmoles, 3.39 g)and hydrogenated at 40 psi over 10.g of 10% Pd/C for 2.25 hours mixture was filtered and concentrated to a white solid. The solid was triturated with ether and filtered to yield 7.3 g of 4-trans-trimethylacetoxy-L-proline methyl ester tosylate M. Pt.: 109°–112° C. Calculated for $C_{18}H_{23}NO_7S$: C, 53.85; H, 6.78; N, 3.49. Found: C, 53.63; H, 6.67; N, 3.61.

4-Trans-trimethylacetoxy-L-proline methyl ester tosylate (0.742 mmoles, 330 mg) was dissolved in 50 ml DMF. Diisopropylethylamine (0.142 ml), 2-[5-[2-(2H-tetrazol-5-yl]-1H-benzimidazol-1-yl]octanoic acid (300 mg), hydroxybenzotriazole (100 mg) and dicyclohexylcarbodiimide (153 mg) were added to the solution. The solution was stirred for 48 hours and filtered. The product was extracted in ethyl acetate, washed with brine, dried over sodium sulfate, and concentrated. The reaction yielded 280 mg of methyl 1-[1-oxo-2-[5-[2-(2H-tetrazol-5-yl)phenyl]-1H-benzimadazol-1-yl]octyl]-4-trans-hydroxy-2-pyrrolidinecarboxylate (MS). The ester was hydrolyzed by adding 20 ml 2N LiOH and 10 ml methanol and stirring for 16 hours. The acid solution was concentrated. The residue was dissolved in water and washed with ether. The pH was adjusted to 3.5 using 2 N HCl. The product was extracted into ethyl acetate, dried over sodium sulfate, and concentrated to yield 80 mg of 1-[1-oxo-2-[5-[2-(2H-tetrazol-5-yl)phenyl]1H-benzimidazol-1-yl]octyl]-4-trans-hydroxy-2-pyrrolindinecarboxylic acid. (MS)

Calculated for $C_{27}H_{31}N_7O$: C, 62.66; H, 6.04; N, 18.94. Found: C,62.86;: H, 6.38; N, 17.71.

EXAMPLE 19

N-[1-Oxo-2-[5-[2-(2H-tetrazol-5yl]phenyl]-1H-benzimidazol-1-yl]octyl]-lysine N-carbobenzyloxy-L-Lysine methyl ester (1.0 mmoles, 0.295 g) and 2-[5-[2-(2H-tetrazol-5-yl)phenyl]-1H-benzimidazol-1-yl]octanoic acid (1.0 moles, 0.405 g) were reacted with 1.0 moles of hydroxybenzotriazole and dicyclohexylcarbodiimide as in Example 37. The stereoisomers were separated on silica gel eluted with 5% EtOH in chloroform with 1% acetic acid. Each was hydrolyzed with sodium hydroxide as in Example 37 and hydrogenated to remove the carbobenzyloxy group in ethanol over 5% Pd/C for 4 hours. The catalyst was removed by filtering through celite. The solvent was removed in vacuo to yield 74 mg of N-[1-Oxo-2-[5-[2-(2H-tetrazol-5-yl)phenyl]-1H-benzimidazol-1-yl]octyl]-lysine. Isomer A (MS)

Calculated for $C_{28}H_{36}N_8O_3 \cdot 5H_2O$ C, 54.02; H, 7.39; N, 18.01. Found: C, 54.15; H, 6.84;N, 17.73.

EXAMPLE 20

2-[5-[2-(2H-Tetrazol-5-yl)phenyl]indol-1-yl]octanoic acid 5-(2-Cyanophenyl)indole (5.04 mmoles, 1.1 g) in 70 ml THF was treated with sodium hydride (255 mg, 50% in mineral oil) and stirred at 0° C. for 30 minutes. Ethyl 2-bromooctanoate (5.5 mmoles) in 40 ml THF was added dropwise. The reaction was stirred at room temperature for 4 hours, cooled, poured onto ice, extracted with ethyl acetate. The organic phase was dried and concentrated. The intermediate was chromatographed over silica gel eluted with 20% ether in hexane. The reaction yielded 1.1 g of ethyl 2-[5-(2-cyanophenyl)indol-1-yl]octanoate. (MS)

Ethyl 2-[5-(2-cyanophenyl)indol-1-yl]octanoate (2.55 mmoles, 990 mg) was dissolved in 2.5 g tributyltinazide and heated at 85°–95° C. for 48 hours. The solution was cooled. Acetonitrile, water, and acetic acid (100 ml of 8:1:1) were added and stirred for 30 minutes. The acetonitrile solution was washed twice with hexane, concentrated, dissolved in ethyl acetate, washed, dried over sodium sulfate and concentrated. The resulting ester was chromatographed over silica gel eluted with 50% ethyl acetate in hexane. (MS). The ester was hydrolyzed by stirring in 20 ml of methanol and 40 ml 2N NaOH at room temperature for 2 hours. The reaction mixture was concentrated. Water was added, and the pH was adjusted to 2.5 using 2N HCl. The resulting precipitate was filtered and dried to yield 400 mg of 2-[5-[2-(2H-tetrazol-5-yl)phenyl]indol-1-yl]octanoic acid. (MS)

M. Pt.: 105°–115° C. Calculated for $C_{23}H_{25}N_5 \cdot 0.5\ H_2O$: C, 66.97; H, 6.35; N, 16.97. Found: C, 66.85; H, 6.17; N, 17.26.

EXAMPLE 21

3-[5-[2-(2Tetrazol-5-yl)phenyl]indol-1-yl]nonanoic acid

Sodium bis (trimethylsilyl)amide (5.6 ml of 1M solution in THF) in 40 ml THF was added dropwise at 0° C. to a solution of 5-(2-cyanophenyl)indole (5.04 mmoles, 1.1 g) in 100 ml THF and stirred at 0° C. for 30 minutes. Methyl 3bromononanoate (5.6 mmoles, 1.32 g) in 20 ml THF was added dropwise. The reaction was stirred at room temperature for 12 hours. An additional 5 mmoles of the base and the bromide were added. The reaction was stirred an additional 12 hours, added To ice water and extracted into ethyl acetate. The organic phase was dried over sodium sulfate and concentrated. The intermediate was chromatographed over silica gel eluted with 50% ether in hexane to yield 700 mg of methyl 3-[5-(2-cyanophenyl)indol-1-yl]nonanoate.

Methyl 3-[5-(2-cyanophenyl)indol-1-yl]nonanoate (1.82 mmoles, 680 mg) was reacted with tributyltinazide (3 g) and hydrolyzed with sodium hydroxide as in Example 20 to yield 80 mg of 3-[5-[2-(2H-tetrazol-5-yl)phenyl]indol-1-yl] nonanoic acid. (MS)

Calculated for $C_{24}H_{27}N_5O_2$: C, 69.04; H, 6.52; N, 16.77. Found: C, 69.10; H, 6.66; N, 16.50.

EXAMPLE 22

2-[5-[2(2H-Tetrazol-5-yl)phenyl]indol 1-yl]heptanoic acid 5-(2-cyanophenyl)indole (5.04 moles, 1.1 g) was reacted with sodium hydride (1.5 mmoles) and ethyl 2-bromoheptanoate (5.6 mmoles, 1.4 g) in DMF. The nitrile was then reacted with tributyltinazide (3.0 g), and the ester hydrolyzed as in Example 20 to yield 330 mg of 2-[5-[2-(2H-tetrazol-5-yl)phenyl]indol-1-yl]heptanoic acid. (MS).

Calculated for $C_{22}H_{23}N_5O_2 \cdot H_2O$: C 64.79; N, 6.13 N, 17.17. Found: C, 64.75; H, 6.07; N, 17.13.

EXAMPLE 23

2-[3-Ethyl-5-[2-(2H-tetrazol-5-yl)phenyl] indol-1-yl]octanoic acid.

5-(2-cyanophenyl)indole (1.26 mmoles, 630 mg) was dissolved in THF (20 ml) and treated with ethylmagnesium bromide (1.26 mmoles, 0.630ml) and ethyl iodide (3.45 mmoles, 0.54 g) as in Example 24 to yield 98 mg of 5-(2-cyanophenyl)-3-ethylindole. (MS)

5-(2-Cyanophenyl)-3-ethylindole (0.36 mmoles, 89 mg) was reacted with sodium hydride(0.40 moles) and ethyl 2-bromoacetate in DMF as in Example 24. The resulting nitrile ester was reacted with tributyltinazide (0.40 g) and hydrolyzed as in Example 20 to yield 134 mg of 2-[3-ethyl-5-[2-(2H-tetrazol-5-yl)phenyl]indol-1-yl]octanoic acid. (MS)

M. Pt.: 110°–113° C. Calculated for $C_{25}H_{29}N_5O_2 \cdot H_2O$: C, 66.79; H, 6.95; N, 15.31. Found: C, 67.11; N, 7.03; H, 15.31.

EXAMPLE 24

2-[3-benzyl-5-[2-(2H-tetrazol-5-yl)phenyl]indol-1-yl]octanoic acid 5-(2-Cyanophenyl)indole (2.3 mmole, 0.50 g) was dissolved in 3 ml THF, cooled to 0° C. Ethyl magnesium bromide (2.41 mmoles, 1.21 ml of 2.0M solution in ether) was added dropwise. Benzyl bromide (94.6 mole, 0.80 g) was added dropwise to the solution. The reaction was refluxed for 24 hours and poured into aqueous ammonium chloride and ethyl acetate. The organic phase was washed with water, dried over sodium sulfate, and concentrated. The intermediate was chromatographed over silica gel eluted with 10% ethyl acetate in hexane to yield 229 mg of 3-benzyl-5-(2-cyanophenyl)indole. (MS)

3-Benzyl-5-(2-cyanophenyl)indole (0.42 mmoles, 130 mg) was reacted with sodium hydride and ethyl 2-bromooctanoate. The nitrile ester was reacted with tributyltinazide and hydrolyzed with sodium hydroxide as in Example 20 to yield 36 mg of 2-[3-benzyl-5-[2-(2H-tetrazol-5-yl)phenyl] indol-1-yl]octanoic acid. (MS)

M. Pt.: 108°–112° C. Calculated for $C_{30}H_{30}N_5O_2$: C, 73.00; H, 6.33; N, 14.19. Found: C, 72.77; H, 6 34; N 14.31.

EXAMPLE 25

2-[5-[2-(2H-tetrazol-5-yl)phenyl]indol-1yl]-3-octenoic acid.

N-Bromosuccinimide (112.5 mmoles, 20.25 g ) was suspended in i00 ml methylene chloride and cooled to 0° C. Dimethylsulfide (135 mmole, 9.2 ml) in 10 ml methylene chloride was added dropwise. The solution was stirred 10 minutes. 1-Hydroxy-2-trans-hexene (75 mmoles, 7.5 g) in 15 ml methylene chloride was added dropwise. The solution was stirred for 30 minutes. Pentane (100 ml) was added. The solution was filtered and concentrated to yield 9.81 g of 1-bromo-2-trans-hexene. The bromo hexene (30.3 mmoles, 6.4 g) was added to a solution of sodium hydride (57 mmoles, 2.3 g) and ethyl acetoacetate (65 mmoles, 3.5 g); and then brominated with N-bromosuccinimide (31.7 mmoles, 5.70 g) as in Example 11 to yield 6.39 g of ethyl 2-bromo-3-transoctenoate.

Ethyl 2-bromo-3-trans-octenoate (2.19 mmole, 0.47 ml) was reacted with 5-2-cyanophenyl)indole (1.83 mole, 0.40 g). The resulting nitrile ester was then reacted with an excess of tributyltinazide, and hydrolyzed with sodium hydroxide according to Example 11 to yield 38 mg of 2-[5-[2-(2H-Tetrazol-5-yl)phenyl]indol-1-yl]-3-trans-octenoic acid. (MS)

M. Pt.: 101°–105° C. Calculated for $C_{23}H_{23}N_5O_2 \cdot H_2O$: C, 65.86; H, 6.05; N, 16.72. Found: C, 65.69; H, 5.78; N, 16.73.

1-hydroxy-2-cis-hexene (75 mmoles, 7.5 g) was converted to ethyl 2-bromo-3-cis-octenoate as above. The resulting bromide was reacted with 5-(2-cyanophenyl)indole to yield 28 mg of 2-[5-[2-(2H-tetrazol-5yl)phenyl]indol-1-yl]-3-cis-octenoic acid. (MS)

M. Pt.: 95°–100° C. Calculated for $C_{23}H_{22}N_5O_2.0.4H_2O$: C, 67.5; H, 5.88; N, 17.11. Found: C, 67.78; H, 5.90; N, 16.71.

EXAMPLE 26

2-[3-Bromo-5-[2-[2H-tetrazol-5-yl)phenyl]indol-1 yl]octanoic acid.

5-(2-Cyanophenyl)indole (1.38 mmoles, 300 mg)was dissolved in DMF (1 ml). A solution of bromine (1.4 mmols, 0.074 ml) in 0.5 ml DMF was added. The reaction was poured into ethyl acetate and brine. The organic phase was washed with water, dried over sodium sulfate, and concentrated. The intermediate was chromatographed over silica gel eluted with 50 % ether in hexane to yield 380 mg of 3-bromo-5-(2-cyanophenyl) indole (MS)

Calculated for $C_{15}H_9N_2Br$: C, 60.83; H, 3.05; N, 9.43. Found: C, 61.16; H, 3.12; N, 9.17.

3-Bromo-5-(2-cyanophenyl)indole (1.21 mmoles, 360 mg) was reacted with sodium hydride (1.5 mmoles, 60 mg) and ethyl 2-bromooctanoate. The resulting nitrile ester was then reacted with an excess of tributyltinazide, and hydrolyzed with sodium hydroxide according to Example 24 to yield 63 mg of 2-[3-bromo-5-[2-[2H-tetrazol-5-yl)phenyl]-indol-1-yl]octenoic acid. (MS)

M. Pt.: 109°–115° C. Calculated for $C_{23}H_{24}N_5O_2.1.25 H_2O$: C, 54.71; H, 5.11; N, 13.79. Found: C, 54.54; H, 5.11; N, 13.79.

EXAMPLE 27

2-[5-(2-2H-Tetrazol-5-phenyl)-indazol-1and 2)-yl]ocatanoic acid

3-Bromotoluene (17.5 mmoles, 3.0 g) was reacted with t-BuLi(19.3 mmoles) and $ZnCl_2$ (19 3 moles, 2.62 g) followed by a $Ni(PPh_3)_4$ coupling to 2-bromobenzonitrile (17.5 mmole, 3.2 g) as in Preparation 1. The intermediate was purified by chromatography over silica gel eluted with 20% ether in hexane to yield 1.58 g of 2-(3-methylphenyl)-benzonitrile (MS)

2-(3-Methylphenyl)benzonitrile (18.1 mmoles, 3.5 g) was added slowly at –5° C. to a mixture of 10 ml nitric acid and 10 ml sulfuric acid. After 5 minutes, the reaction was diluted with cold water. The solid was collected, dissolved in THF. The solution was dried and concentrated. The solid was recrystallized from ether and hexane to yield 2.45 g of 2-(3-methyl-4-nitrophenyl)benzonitrile. (MS)

M. Pt.: 128°–136° C. Calculated for $C_{14}H_{10}N_2O_2$: C, 70.38, H, 4.23; N, 11.76. Found: C, 70.88; H, 4.25; N, 11.80.

2-(3-Methyl-4-nitrophenyl)benzonitrile (6.3 moles, 1.5 g) was hydrogenated in ethyl acetate (50 ml) over 5% Pd/C (0.50 g). The catalyst was filtered, and the solution concentrated to an oil. The oil was dissolved in 10 ml of methylene chloride and triethylamine (9.4 mmoles, 1.4 ml). Acetic anhydride (9.4 mmoles, 0.960 g) and 4-dimethylaminopyridine (50 mg) were added. The reaction was stirred for 1 hour and poured into 20 ml of 5N HCl. The organic phase was washed with saturated sodium bicarbonate solution, dried over sodium sulfate, and concentrated. The product was crystallized from ether and hexane to yield 1.2 g of 2-(4-acetamino-3methylphenyl)benzonitrile. (MS)

M. Pt.: 135°–143° C. Calculated for $C_{16}H_{14}N_2O$: C, 76.77; H 5.64; N, 11.19 Found: C, 77.04; , H, 5.51; N 10.97.

2-(4-Acetamino-3-methylphenyl)benzonitrile (15.2 mmole, 3.8 g) was dissolved in 50 ml acetic acid and treated for 1 hour at room temperature with a scream of gaseous $N_2O_5$ generated by the addition of nitric acid to sodium nitrite. Benzene and brine were added to the reaction. The organic layer was separated, dried and warmed gently on a rotorvap (45° C.) for 1 hour. The solution was concentrated. Ether and saturated sodium bicarbonate were added. The organic phase was dried and concentrated. The residue was chromatographed over silica gel eluded with 50% ether in hexane to yield 240 mg of 5(2-cyanophenyl)indazole. (MS)

M. Pt.: 163°–170° C. Calculated for $C_{14}H_9N_3$: C, 76.72;, H, 4.14; N, 19.17. Found: C, 76.34; H, 4.29; N, 18.70.

5-(2-Cyanophenyl)-1H-indazole (1.0 mmole, 220 mg) was dissolved in DMF and at room temperature. Sodium hydride (1.1 mmoles, 44 mg of 60%) was added.

The solution was stirred for 30 minutes. Ethyl 2-bromooctanoate (1.5 mmoles, 384 mg.) was added and stirred for 16 hours. Ethyl acetate was added. The solution was washed with brine, dried over sodium sulfate and concentrated. The 1- and 2- substituted derivatives of ethyl 2-[5-(2-cyanophenyl)-1H-indazol-1(and 2)-yl]octanoate were separated by column chromatography over silica gel eluted with 15% ether in hexane.

Ethyl 2-[5-(2-cyanophenyl)-1H-indazol-1-yl]octanoate (0.307 mmole, 120 mg) was dissolved in tributyltinazide (1.5 mmoles, 0.5 g) and heated at 85° C. for 2 days. A solution of acetonitrile, water, and acetic acid (8:1:1) was added. The solution was washed with hexane. The acetonitrile solution was concentrated. The residue was treated with 10 ml of 1N NaOH and stirred for 1hour. Ether was added. The aqueous layer was filtered through a cotton plug and acidified to pH 3.0 using 2N HCl. The intermediate was extracted with 5% ethanol in ethyl acetate, dried over sodium sulfate, and concentrated. The residue was triturated with ethyl acetate/hexane to yield 58 mg of 2-[5-[2-(2H-tetrazol-5-yl)phenyl]-2H-indazol-1-yl]octanoic acid. (MS)

M. PC.: 105°–110° C. Calculated for $C_{22}H_{24}N_6O_2$: C,65.33; H, 5.98; N, 20.78. Found: C, 65.38; H, 6.20; N, 20.28.

Ethyl 2-[5-(2-cyanophenyl)indazol-2-yl]octanoate (0.167 mmole, 65 mg) was reacted in the same manner as the -1-yl isomer to yield 67 mg of 2-[5-(2-2H-tetrazol-5-ylphenyl)-1H-indazol-2-yl]octanoic acid. (MS)

M. Pt.: 113°–120° C. Calculated for $C_{22}H_{24}N_6O_2$: C, 65.33; H, 5.98; N, 20.78. Found: C, 65.64; H, 6.00; N, 19.74.

EXAMPLE 28

5-[2-(2H-tetrazol-5-yl)phenyl]-1-[1-(3 -trifluoromethylphenyl)-1-pentyl]indole

1-Bromo-1-(3-trifluoromethylphenyl)pentane (3.5 mmoles, 1.01 g) was reacted with sodium hydride (3.5 mmoles) and 5-(2-cyanophenyl)indole (3.2 mmoles, 700 mg) in DMF. The tetrazole moiety was formed according to the procedures in Example 29 to yield 120 mg of 5-[2-(2H-tetrazol-5yl)phenyl-1-[1(3-trifluoromethyl-phenyl)-1pentyl-1pentyl]indole. (MS)

M. Pt.: 75°–80° C. Calculated for $C_{27}H_{24}F_3N_5$: C, 68.20; H, 5.09; N, 14.73. Found: C, 68.44; H, 5.25; N, 14.45.

EXAMPLE 29

5-[2-(2H-tetrazol-5-yl)phenyl]1-[1-(4-trifluoromethylphenyl)-1-pentyl]indole.

Sodium hydride (5 mmoles, 200 mg of 60% in mineral oil) was added to 5-(2-cyanophenyl)indole (4.6 mmoles, 1.0 g.) in 50 ml DMF and stirred for 45 minutes. 1-Bromo-1-(4-trifluoromethylphenyl)pentane (5 mmoles, 1.44 g) was added. The reaction was stirred at room temperature overnight, poured into ice water, and extracted into ethyl acetate. The organic layer was dried over sodium sulfate and concentrated. The intermediate was chromatographed over silica gel eluted with 10% ethyl acetate in hexane to yield 820 mg of 5-(2-cyanophenyl)-1-[1-(4-trifluoromethylphenyl)-1pentyl]indole.

5-(2-Cyanophenyl)-1-[1-(4-trifluoromethylphenyl)-1-pentyl]indole (1.9 mmoles, 800 mg) was dissolved in 2.0 g of tributyltinazide and heated at 95° C. for 24 hours. The solution was cooled. Acetonitrile, water, and acetic acid (50 ml of 8:1:1) were added. The acetonitrile solution was washed with hexane, concentrated, diluted with ethyl acetate, washed with water, dried over sodium sulfate and concentrated. The product was chromatographed on silica gel eluted with ethyl acetate to yield 120 mg of 5-[2-(2H-tetrazol-5-yl)phenyl]-1-[1-(4-trifluoromethylphenyl)-1pentyl]indole.

Calculated for $C_{27}H_{24}F_3N_5$: C, 68.20; H, 5.09; N, 14.73. Found: C, 68.34; N, 5.02; N, 14.49.

EXAMPLE 30

2-[1-Hexyl-5-[2-(2H-tetrazol-5-yl)phenyl]-1H-benzimidazol-2yl]propionic acid.

Dicyclohexylcarbodiimide (0.11 moles, 2.26 g), hydroxybenzotriazole, (0.011 moles, 1.48 g) and monomethylsuccinate (0.011 moles, 1.45 g) were dissolved in 75 ml of DMF. 2-(3,4-Diaminophenyl)benzonitrile (0.01 moles, 2.0 g) was added. The reaction was stirred at room temperature for 48 hours The solvent was removed in vacuo. The residue was dissolved in ethyl acetate and washed thoroughly with brine. The ethyl acetate solution was dried over sodium sulfate and filtered. The solvent was removed. The residue was purified by HPLC on silica gel eluted with ethyl acetate. The material was dissolved in 400 ml toluene with 5 mg of p-toluenesulfonic acid and refluxed for 8 hours. The solvent was removed. The residue was purified by HPLC on silica gel eluted with ethyl acetate to yield 2.3 g of methyl 3-[5-(2-cyanophenyl)-1H-benzimidazole-2-yl]propionate. (MS).

Calculated for $C_{18}H_{15}N_3O_2$: C, 70.81; H, 4.95; N, 13.76. Found: C, 70.70; H, 5.06; N, 13.75.

Potassium carbonate (7.0 mmoles, 0.87 g) and 1bromohexane (7.0 moles, 1.15 g. ) were added to methyl 3-[5(2-cyanophenyl)-1H-benzimidazol-2-yl]propionate (6.3 mmoles, 1.94 g) in 20 ml DMF. The reaction was stirred at room temperature for 48 hours. Ethyl acetate was added and washed thoroughly with water. The organic phase was dried over sodium sulfate. The solvents were removed in vacuo to yield 1.56 g of methyl 3-[5(and 6)-(2-Cyanophenyl)-1-hexyl-1H-benzimidazol-2-yl]propionate. (MS)

Methyl 3-[5-(2-cyanophenyl)-1-hexyl]-1H-benzimidazol-2-yl]propionate (4 mmoles, 1.56 g) was dissolved in 4 g of tributyltinazide and heated at 90° C. for 48 hours. Ethyl acetate was added. The organic layer was washed with water, dried over sodium sulfate, filtered and concentrated in vacuo. Methanol (100 ml) and 2N NaOH (75 ml) were added to the residue. The solution was stirred for 2 hours. The solvent was removed. The residue was dissolved in ether and washed with water. The pH of the water layer was adjusted to 2.0 with 1N HCl. The solid was filtered and dried. The isomers were separated by HPLC using reverse phase chromatography eluted with 28% acetonitrile in water with 0.5% sodium acetate. 2-[1-Hexyl-5-[2-(2H-tetrazol-5-yl)phenyl]benzimidazol-2-yl] propionic acid. (MS)

M. Pt.: Dec. 130°–135° C. Calculated for $C_{23}H_{26}N_2O_2$: C, 66.01; H, 6.26; N, 20.08. Found: C, 65.72, H, 6.41; N, 19.88.

EXAMPLE 31

2-[2-Dimethylamino-5-[2-(2H-tetrazol-5-yl) phenyl]1H-benzimidazol-1-yl]octanoic acid.

2-(3,4-Diaminophenyl) benzonitrile (1.25 mmole, 262 mg) and phosgene iminochloride (1.56 moles, 256 mg) were dissolved in 5 ml chloroform and heated at 50° C. for 1 hour. The solution was filtered, concentrated and chromatographed over silica gel eluted with 30% hexane in ethyl acetate to yield 208 mg of 5-(2-cyanophenyl)-2-dimethylamino-1H-benzimidazole (MS) M Pt. 148°–155° C.

5-(2-Cyanophenyl)-2-dimethylamino-1H-benzimidazole (5.1 moles, 1.33 g) in 10 ml DMF was treated with sodium hydride (6.6 mmoles, 0.26 g of 60% in mineral oil) and stirred for 15 minutes. Ethyl 2-bromooctanoate (6.6 moles, 1.66 g) was added. After stirring for 2 hours at room temperature, ethyl acetate was added. The ethyl acetate solution was washed with water, dried, concentrated. The residue was chromatographed over silica gel eluted with 50% ether in hexane. The resulting nitrile (2.5 mmoles, 0.90 g) and tributyltinazide (5.0 mmole, 1.6 g) were heated am 85° C. for 32 hours, chromatographed over silica gel eluted with 5% ethanol in ethyl acetate to yield 500 mg of a mixture of regioisomers. The regioisomers were separated and purified by reverse phase chromatography eluted with acetonitrile with 1% ammonium acetate co yield 139 mg of the 5-regioisomer, 2-[2-Dimethylamino-5-[2-(2H-tetrazol-5-yl)phenyl]-1H-benzimidazol-yl]octanoic acid. (MS)

M. Pt.: Dec. >155° C. Calculated for $C_{24}H_{29}N_7O_2 \cdot 0.3H_2O$: C, 63.64; H, 6.59; N, 21.65. Found: C, 63.69; H,6.63; N, 21.41.

EXAMPLE 32

2-[5-[2-(2H-Tetrazol-5-yl)phenyl-2-diethylamino-1H-benzimidazol-1-yl]octanoic acid.

2(3,4-Diaminophenyl)benzonitrile (4.78 mmoles, 1.0 g) was reacted as described in Example 31 with (dichloroethylene) diethylammonium chloride (1.435 mmoles, 2.73 g prepared following the procedure described in Angew. Chem., Ed. 12: 806 (1973)) to yield 0.91 g of 5-(2-cyanopheny)-2-diethylamino-1H-benzimidazole.

M. Pt.: 138°–142° C.

5-(2-Cyanophenyl)-2-diethylamino-1H-benzimidazole (4.8 mmoles, 0.91 g) was reacted with sodium hydride (6.3 mmoles, 0.252 g), ethyl 2-bromooctanoate (6.3 mmoles, 1.58 g) and then tributyltinazide according to the procedure in Example 31 to yield 50 mg of 2-[5-[2-(2H-tetrazol-5-yl)phenyl-2-diethylamino-1H-benzimidazol-1-yl]octanoic acid. (MS)

M. Pt.: 150°–155° C. Calculated for $C_{26}H_{33}N_7O_2$: C, 65.66; H, 6.99; N, 20.61. Found: C, 65.90; H, 7.13; N, 20.40.

EXAMPLE 33

2-[2-Pentafluoroethyl-5-[2-(2H-tetrazol-5-yl)phenyl]-1H-benzimidazol-1-yl]octanoic acid.

2-(3,4-Diaminophenyl)benzonitrile (9.6 mmoles, 2.0 g) was dissolved in 40 ml of pentafluoropropionic acid and heated at 115° C. for 20 hours. After cooling, the solvent was removed in vacuo. The residue was dissolved in ethyl acetate. The ethyl acetate solution was added slowly to saturated sodium bicarbonate. The intermediate was extracted with ethyl acetate, washed with brine, dried over sodium sulfate and concentrated. The residue was chromatographed over silica gel eluted with 25% ethyl acetate in hexane to yield 1.1 g of 5-(2-cyanophenyl)-2-pentafluoroethyl-1H-benzimidazole. (MS).

Calculated for $C_{16}H_8F_5N_3$: C, 56.98; H, 2.39; N, 12.46. Found: C, 57.17; H, 2.49; N, 12.38.

5-(2-Cyanophenyl)-2-pentafluoroethyl-1H-benzimidazole (3.3 mmoles, 1.1 g) was dissolved in 25 ml DMF. Sodium hydride (3.75 mmoles, 0.15 g of 60% in mineral oil) was added. The solution was stirred for 20 minutes. Ethyl 2-bromooctanoate (4.66 mmoles, 1.0 ml) was added. The reaction was heated at 65° C. for 16 hours, cooled and concentrated in vacuo. Ethyl acetate was added. The solution was washed with dilute sodium bicarbonate, water and brine. The organic layer was dried over sodium sulfate, concentrated and purified by chromatography over silica gel eluted with 10% ethyl acetate in hexane to yield 1.0 g of ethyl 2-[5(and 6)-(2-cyanophenyl)-2-pentafluoroethyl-1H-benzimidazol-1-yl]octanoate (MS)

Ethyl 2-[5(and 6)-(2-cyanophenyl)-2-pentafluoroethyl-1H-benzimidazol-1-yl]octanoate (1.9 mmoles, 1.0 g) was dissolved in 10 ml tributyltinazide and heated at 95° C. overnight. The reaction mixture was cooled. Acetonitrile, water, and acetic acid (100 ml of 8:1:1) were added and washed three times with 250 ml hexane. The acetonitrile was removed in vacuo. Ethyl acetate was added. The ethyl acetate solution was washed with water and brine, dried over sodium sulfate, and concentrated. The regioisomers were purified over a silica gel column eluted with 50% ethyl acetate in hexane with 1% acetic acid and separated by reverse phase HPLC eluted with acetonitrile/water. The reaction yielded 0.14 g of ethyl 2-[5-[2-(2H-tetrazol-5-yl)phenyl]-2-pentafluoroethyl-1H-benzimidazol-1-yl]octanoate. (MS).

M. Pt.: 70°–72° C. Calculated for $C_{26}H_{27}F_5N_6O_2$: C, 56.72; H, 4.93; N, 15.26. Found: C, 56.46; H, 5.07; N, 15.34.

Ethyl 2-[5-[2-(2H-tetrazol-5-yl)phenyl]-2-pentafluoroethyl-1H-benzimidazol-1-yl]octanoate (0.25 mmoles, 0.14 g) was dissolved in 25 ml ethanol and 1 ml 5N NaOH. The solution heated on a steam bath for 1 hour. The solvent was removed in vacuo. The residue was dissolved in water. The pH was adjusted to 3.0 using 5N HCl. The precipitate was collected and dried to yield 0.12 g of 2-[2-pentafluoroethyl-5-[2-(2H-tetrazol-5-yl)phenyl]-1H-benzimidazol-1-yl]octanoic acid. (MS)

M. Pt.: Dec. 130°–135° C. Calculated for $C_{24}H_{23}F_5N_6O_2 \cdot 1.5\ H_2O$: C, 52.46; H, 4.77; N, 15.29. Found: C, 52.27; H, 4.40; N, 15.20.

EXAMPLE 34

2-[5-[2-(2H-Tetrazol-5-yl)phenyl]-1H-benzimidazol-1-yl]hexyl-5-tetrazole.

5-(2-Cyanophenyl)-1H-benzimidazole (2.28 mmole, 0.5 g) was dissolved in 5 ml DMF. Sodium hydride (2.4 mmoles, 110 mg. of 60% in mineral oil) was added portionwise. After 10 minutes, 2-bromooctanonitrile (2.4 mmoles, 489 mg.) was added. The solution was stirred two hours at room temperature. Water was added. The intermediate was extracted with ethyl acetate. The organic phase was dried and concentrated. The residue was chromatographed over silica gel with a gradient of 0–50% ethyl acetate in ether. The intermediate was dissolved in tributyltinazide (5.0 mmole, 1.85 g) and heated at 90° C. for 2 days. NaOH (5 ml of 1N) and 1 ml EtOH were added. The solution stirred at 40° C. for 3 hours. Ether was added. The aqueous phase was separated and extracted with ether. The pH was adjusted to 3.0 using 2N HCl. The product was extracted with 10% ethanol in ethyl acetate. The ethyl acetate layer was dried and concentrated to a white solid. The regioisomers were separated by reverse phase chromatography. The reaction produced 45 mg of 2-[5-[2-(2H-tetrazol-5yl)phenyl]-1H-benzimidazol-1-yl]hexyl-5-tetrazole. (MS)

M. Pt.: 160°–163° C. Calculated for $C_{22}H_{24}N_{10} \cdot 0.4$ HOAc: C, 60.25; H, 5.72; N, 30.55. Found C, 60.23; H, 5.87; N, 30.92.

EXAMPLE 35

2-[2-Dimethylaminomethyl-5-[2-(2H-tetrazol-5yl)phenyl]-1H-benzimidazol-1-yl]octanoic acid 2-(3,4-Diaminophenyl)benzonitrile (4.8 mmoles, 1.0 g) was reacted with ethyl chloroacetamidate (5.0 mmoles, 0.78 g) as in Example 45 to yield 820 mg of 2-chloromethyl-5-(2-cyanophenyl)-1H-benzimidazole. (MS).

M. Pt.: 150°–158° C.

2-Chloromethyl-5-(2-cyanophenyl)-1-benzimidazole (1.31 mmole, 0.350 g) was dissolved in 2 ml THF and cooled to 0° C. Dimethylamine (1ml) was added. The solution was stirred at room temperature for 20 minutes. Ethyl acetate was added. The organic phase was washed with water, dried over sodium sulfate, and concentrated to yield 270 mg of 5-(2-cyanophenyl)-2-dimethylaminomethyl-1H-benzimidazole. (MS)

Calculated for $C_{17}H_{16}N_4$: C, 73.89; H, 5.84; N, 20.27. Found: C, 74.24; H, 5.88; N, 19.54.

5-(2-Cyanophenyl)-2-dimethylaminomethyl-benzimidazole (2.5 mmoles, 0.693 g) in DMF was treated with sodium hydride (3.8 mmoles, 0.152 g) and ethyl 2-bromooctanoate (3.8 mmoles, 0.954 g) as in Example 45 to yield 720 mg of the nitrile ester. The nitrile ester was dissolved in 2.5 g of tributyltinazide and heated at 85° C. for 48 hours. The mixture was chromatographed over silica gel eluted with ether then 20% ethanol in ethyl acetate to yield 720 mg of a mixture of the regioisomers, 2-[2-dimethylaminomethyl-5(and 6)-[2-(2H-tetrazol-5-ylphenyl]-1H-benzimidazol-1-yl]octanoic acid. The regioisomers were separated and purified by reverse phase HPLC. The 5-substitution was hydrolyzed with sodium hydroxide as in Example 45 to yield 60 mg of 2-[2-dimethyl-aminomethyl-5-[2-(2H-tetrazol-5ylphenyl]1H-benzimidazol-1-yl]octanoic acid. (MS) M. Pt. 155° C.

Calculated for $C_{25}H_{31}N_7O_2 \cdot 0.6\ H_2O$: C, 63.57; H, 6.87; N, 20.76. Found: C, 63.7; H, 6.81; N, 20.43.

EXAMPLE 36

2-[2-(1Pyrrolidinomethyl)-5-[2-(2H-tetrazol-5-yl)phenyl]-1H-benzimidazol-1-yl]octanoic acid 2-Chloromethyl-5-(2-cyanophenyl)-1H-benzimidazole (2.28 mmoles, 0.54 g-see Example 35) and pyrrolidine (5.26 mmole, 0.375 g.) were dissolved in THF and stirred at room temperature. The solvents were removed in vacuo. The residue was dissolved in ethyl acetate, washed with water, and concentrated to yield 0.583 g of 5-(2-Cyanophenyl)-2(1-pyrroidinomethyl)-1H-benzimidazole.

5-(2-Cyanophenyl)-2-(1-pyrrolidinomethyl)-1H-benzimidazole (1.93 mmoles, 0.583 g) was treated with sodium hydride and ethyl 2-bromooctanoate (2.26 mmoles, 0.66 g) as in Example 45 to yield 0.750 g of the nitrile ester. The nitrile ester was converted to the tetrazole and hydrolyzed as in Example 45 to yield 100 mg of 2-[2-(1pyrrolidinomethyl)-5-[2-(2H-tetrazol-5-yl)phenyl]-1H-benzimidazol-1-yl]octanoic acid. (MS).

M. Pt.: Dec. 190° C. Calculated for $C_{27}H_{32}N_7O_2 \cdot 1.5 H_2O$: C, 63.16; H, 6.36; N, 19.10. Found: C, 62.80; H, 6.64; N, 19.32.

EXAMPLE 37

1-[1-Oxo-2-[5-[2-(2H-tetrazol-5-yl)phenyl]-1H-benzimidazol-1-yl]octyl]-N-methylglycine Sarcosine hydrochloride (1.23 mmoles, 190 mg) was dissolved in DMF. Diisopropylethylamine (1.23 moles, 0.215 ml) was added. The solution was treated with 1.23 mmoles of 2-[5-[2-(2H-tetrazol-5-yl)phenyl]-1H-benzimidazol-1-yl]octanoic acid, hydroxybenzotriazole and dicyclohexylcarbodiimide as in Example 13. The resulting ester was hydrolyzed with 5.0 ml methanol and 5.0 ml 1N NaOH for 2 hours. The solvents were removed. Water was added. The solution was washed with ether. The pH was adjusted to 4.0 using 2N HCl. The precipitate was filtered and dried to yield 1-[1-oxo-2-[5-[2-(2H-tetrazol-5-yl)phenyl]-1H-benzimidazol-1-yl]octyl]-N-methylglycine.

Calculated for $C_{24}H_{30}N_7O_3$: C, 61.91; H, 6.19; N, 20,22. Found: C, 61.98; H, 6.05, N, 19.72.

EXAMPLE 38

N-[5-[2-(2H-Tetrazol-5-yl)phenyl]-1-hexyl-1H-benzimidazol-2-yl]methyl-L-proline.

2-Chloromethyl-5-(2-cyanophenyl)-1H-benzimidazole (1.87 mmoles, 0.50 g-prepared according to Example 35) was added to a mixture of L-proline hydrochloride benzyl ester (5.61 moles, 1.3 6 g) and diisopropylethyl amine (11.77 mmoles, 1.45 g) in 5 ml THF. The solution was stirred at room temperature for 2 hours. Ethyl acetate was added, washed with water, dried, concentrated and chromatographed over silica gel eluted with 40% hexane in ethyl acetate to yield 327 mg of N-[5-(2-cyanophenyl)-1H-benzimidazol-2-yl]methyl-L-proline benzyl ester. (MS)

Calculated for $C_{27}H_{24}N_4O_2$: C, 74.29; H, 5.54; N, 12.83. Found: C, 73.92; H, 5.47; N, 12.27.

N-[5-(2-cyanophenyl)-1H-benzimidazol-2-yl]methyl-L-proline benzyl ester (2.02 mmoles, 885 mg) was dissolved in DMF and treated with sodium hydride (3.0 moles, 0.121 mg) and then 1-bromohexane (3.0 moles, 0.50 g.). After stirring for 20 minutes, ethyl acetate was added, washed with water, dried over sodium sulfate, concentrated and chromatographed over silica gel eluted with 10% ethyl acetate in ether to yield 667 mg of nitrile. The nitrile was treated with tributyltinazide (1 g) and heated at 85° C. for 2 days. Sodium hydroxide was added. The solution was washed with ether, acidified to pH 3.0 using 2N HCl and extracted with 10% ethanol in ethyl acetate. The organic phase was dried over sodium sulfate, concentrated, and purified by reverse phase HPLC to yield 25 mg of N-[5-[2-(2H-tetrazol-5-yl)phenyl]-1-hexyl-1H-benzimidazol-2-yl]methyl-L-proline. (MS).

M. Pt. 150°–155° C. Calculated for $C_{26}H_{31}N_7O_2$: C, 65.94; H, 6.60; N, 20.70. Found; C, 65.72; H, 6.55; N, 20.53.

EXAMPLE 39

1-[1-Oxo-2-[5-[2-(2H-tetrazol-5-yl)phenyl]-1H-benzimidazol-1-yl]methyl-5-hexyl-L-proline N-Benzyl-glutamic acid (35 g) was dissolved in 300 ml of water and refluxed for 15 hours. The solution was extracted with methylene chloride, washed with brine, dried over sodium sulfate and concentrated to yield 32 g of N-benzyl-5-oxo-proline. The acid (55.25 mmoles, 12.1 g) was dissolved in 15 ml of DMF and 30 ml acetonitrile. The solution was cooled to −25° C. Oxalyl chloride (5.0 ml) in 10 ml acetonitrile was added. The solution was stirred vigorously for 30 minutes. A solution of t-butanol (135 mmoles, 10.0 g) and pyridine (13.2 g) in 10 ml acetonitrile was added over 30 minutes and then warmed to 0° C. Brine and ethyl acetate were added. The organic phase was diluted and washed with water, dried and concentrated to yield 10.7 g of N-benzyl-5-oxo-L-proline t-butyl ester. (MS)

M. Pt.: 59°–63° C. Calculated for $C_{16}H_{21}NO_3$: C, 69.79; H, 7.69; N, 5.09. Found: C, 69.59; H, 7.85; N 5.11.

Triflic anhydride (71 mmoles, 20 g) was added at −27° C. to a solution of pyridine (74 mmoles, 5.9 g) in 150 ml methylene chloride with vigorous stirring. The solution was warmed to room temperature. Benzyl 2-hydroxyhexanoic acid (57 mmoles, 12.65 g) in 15 ml methylene chloride was added over 2 minutes. The solution was stirred for 1 hour and filtered. The filtrate was concentrated, filtered through silica gel eluted with hexane, and evaporated to yield 17.0 g of benzyl 2-(trifluoromethanesuifonylhydroxy)hexanoic acid. (MS)

Calculated for $C_{13}H_{17}F_3O_5S$: C, 47.45; H, 4.84. Found: C, 47.75; H, 5.01.

N-Benzyl-5-oxo-L-proline t-butyl ester (37 mmole, 10.2 g) was dissolved in 300 ml THF. $P_4O_{10}$ (11.3 mmoles, 5.04 g) was added portionwise at 1 hour intervals. The solution was filtered, concentrated, dissolved in ether, washed with 10% sodium bicarbonate, dried over sodium sulfate and concentrated to yield 7.3 g of N-Benzyl-5-thioxo-L-proline t-butyl ester. (MS).

M. Pt.: 72°–78° C. Calculated for $C_{16}H_{21}NO_2S$: C, 65.95; H, 7.26; N, 4.81. Found: C, 66.23; H, 7.49; N, 4.81.

The thiolactam (23.7 mmole, 6.9 g) was dissolved in 8 ml acetonitile and cooled to 0° C. A solution of benzyl 2-(trifluoromethanesulfonylhydroxy)hexanoic acid (24.9 mmoles, 8.8 g) in 4 ml acetonitrile was added. The reaction was stirred ac room temperature for 4 hours. The reaction was cooled to 0° C.

Triphenylphosphine (2.84 mmoles, 7.45 g) and 100 ml of methylene chloride were added. A solution of N-methylpiperidine (42.7 mmoles, 4.2 g) in 15 ml methylene chloride was added dropwise over 30 minutes. The reaction was stirred at 0° for 4.5 hours. The reaction was poured into cold phosphoric acid. Saturated sodium bicarbonate was added. The organic phase was dried over sodium bicarbonate and concentrated. The residue was chromatographed over silica gel eluted with 20% ether in hexane to yield 9.55 g of the carbamate. (MS) The carbamate (3.02 mmoles, 1.40 g.) and ammonium formate (27.5 mmole, 1.75 g) in 10 ml methanol and 10 ml acetic acid was added to 10% Pd/C. The reaction was sonicated for 1.5 hours at room temperature, filtered through celite, and concentrated. The residue was diluted with water. Solid NaHCO$_3$ was added. The intermediate was extracted with chloroform, dried over sodium sulfate, and concentrated to yield 0.584 g of 5-cis-hexyl-L-proline t-butyl ester. (MS)

Calculated for C$_{14}$H$_{26}$NO$_2$: C, 69.66; H, 11.27; N, 5.80. Found: C, 69.62; H, 11.16; N, 5.51.

1-[5-(2-Cyanophenyl)-1H-benzimidazol-1-yl]acetic acid (1.8 mmoles, 0.50 g, prepared by reacting 5-(2-Cyanophenyl)benzimidazole with sodium hydride and ethyl bromoacetate in DMF as in Example 3) was dissolved in 2 ml DMF and reacted with 5-cis-hexyl-L-proline t-butyl ester (1.8 mmole, 0.43 1 g), hydroxybenzotriazole and dicyclohexylcarbodiimide as in Example 48. The nitrile ester was chromatographed over silica gel eluted with ethyl acetate co yield 583 mg of t-butyl 1-[1-oxo-2-[5-(2cyanophenyl)-1H-benzimidazol-1-yl]methyl-5-butyl-2-pyrrolidinecarboxylate.

t-Butyl 1-[1-oxo-2-[5-(2-cyanophenyl)-1H-benzimidazol-1-yl]methyl-5-butyl-2-pyrrolidinecarboxylate (1.06 mmoles, 530 mg) was reacted with tributyltinazide (3.18 mmole, 1.05 g) and hydrolyzed as in Example 33. The tetrazole was cooled to 0° C. Trifluoroacetic acid (1.0 ml in 0.2 ml anisole) was added. The solution was allowed co warm to room temperature for 30 minutes. The solvent was removed. The residue was dissolved in 1N NaOH and acidified to pH 3.5 using 2N HCl. The precipitate was filtered to yield 177 mg of 1-[1-Oxo-2-[5(and 6)-[2-(2H-tetrazol-5-yl]-phenyl-]-1H-benzimidazol-1-yl]methyl-5-hexyl-L-proline. The regioisomers were separated, and the 5-isomer purified by reverse phase HPLC eluted with acetonitrile with 1% ammonium acetate. 1-[1-Oxo-2-[5-[2-(2H-tetrazol-5-yl]phenyl]1H-benzimidazol-1-yl]methyl-5-hexyl-L-proline. (MS)

M. Pt.: 160°–165° C. Calculated for C$_{26}$H$_{29}$N$_{7O3}$.H$_2$O: C, 61.77; H, 6.18; N, 19.39. Found: C, 61.43; H, 6.60; N, 19.47.

EXAMPLE 40

1-[1-oxo-2-[5-[2-2H-tetrazol-5-yl)phenyl]-1H-benzimidazol-1-yl]octyl-4,4-ethylenedioxy-L-proline.

A chromic acid solution (10.66 ml of concentrated H$_2$SO$_4$ and 13.4 g CrO$_3$ diluted to 55 ml) was added dropwise at 0° C. to N-carbobenzyloxy-4-trans-hydroxy-L-proline methyl ester (0.054 moles, 15.0 g) in 400 ml acetone and stirred for 1 hour. Methanol (40 ml) was added. The solution was stirred with celite, filtered, concentrated and chromatographed over silica gel eluted with ethyl acetate in hexane. The resulting ketone (9.0 m/mole, 2.5 g), ethylene glycol (10 ml) and p-toluenesulfonic acid (0.5 g) were refluxed in 100 ml toluene for 16 hours. A Dean-Stark trap was added, and the water was removed. The mixture was poured into ice water, concentrated and chromatographed over silica gel. The protecting group was removed by hydrogenation in 50 ml ethanol over 0.3 g of 10% Pd/C to yield 421 mg of methyl 4,4-ethylenedioxy-L-proline. (MS)

4,4-Ethylenedioxy-L-proline methyl ester (1.23 mmoles, 254 mg), 2-[5-[2-(2H-tetrazol-5-yl)phenyl]-1H-benzimidazol-1-yl]octanoic acid (123 mmoles, 500 mg) and hydroxybenzotriazole (1.23 mmoles, 183.5 mg) were dissolved in 5.0 ml DMF. Dicyclohexylcarbodiimide (1.23 mmoles, 280 mg.) was added. The product was hydrolyzed and purified as in Example 15 to yield 190 mg. (MS)

M. Pt.: 150°–155° C. Calculated for C$_{29}$H$_{33}$N$_7$O$_5$.2H$_2$O: C 58.48; H, 6.26; N, 16.46. Found: C, 58.42; H, 6.04; N, 16.40.

EXAMPLE 41

N-[1-Oxo-2-[5-[2-(2H-tetrazol-5-yl)phenyl]-1H-benzimidazol-1-yl]octyl]-L-aspartic acid L-Dimethyl aspartate (1.0 mmole, 0.161 g), 2-[5-[2(2H-tetrazol-5-yl)phenyl]-1H-benzimidazol-1-yl]octanoic acid (1.0 mmoles, 0.405 g), hydroxybenzotriazole (1.00 mmoles, 0.135 g) and dicyclohexylcarbodiimide (1.0 mmoles, 0.206 g) were reacted and purified as in Example 19. The resulting ester was hydrolyzed as in Example 37 to yield 0.12 g of N-[1-Oxo-2-[5-[2-(2H-tetrazol-5-yl)phenyl]-1H-benzimidazol-1-yl]octyl]-L-aspartic acid (MS).

M. Pt.: 190°–195° C. Calculated for C$_{26}$H$_{29}$N$_7$O$_5$: C, 60.11; H, 5.63; N, 18.87. Found: C, 60.92; H, 5.84; N, 17.51.

EXAMPLE 42

N-[1-Oxo-2-[5-[2-(2H-tetrazol-5-yl)phenyl]-1H-benzimidazol-1-yl]octyl]-L-serine

Serine methyl ester (1.0 mmoles, 0.119 g ), diisopropylethylamine (1.0 mmoles, 0.206 g), 2-[5-[2-(2H-tetrazol-5-yl)phenyl]-1H-benzimidazol-1-yl]octanoic acid (1.0 mmoles, 0.405 g), hydroxybenzotriazole (1.0 mmole, 0.135 g), and dicyclohexylcarbodiimide (1.0 mmoles, 0.206 g) were reacted as in Example 37. The resulting ester 0.19 moles, 0.097 g) was hydrolyzed as in Example 37 to yield 0.052 g of N-[1-oxo-2-[5-[2-(2H-tetrazol-5-yl)phenyl]-1H-benzimidazol-1-yl]octyl]-L-serine (MS).

M. Pt.: 170°–180° C.

EXAMPLE 43

1-[1-Oxo-2-[5-[2-(2H-tetrazol-5-yl]phenyl]-1H-bezimidazol-1-yl]octyl-2-azetidinecarboxylic acid 2-Azetidinecarboxylic acid (39.6 moles, 4.0 g) was dissolved in sodium hydroxide 44 ml, 1N and 30 t-butanol. Di-t-butyldicarbonate (39.6 mmoles, 8.83 g) was added over 1 hour. The reaction was stirred at room temperature overnight, washed with 50 ml hexane, and acidified to pH 1.5 using 2N HCl. The product was extracted with ether. The ether solution was dried and concentrated to yield 6.15 g of N-t-Boc-azetidine-carboxylic acid. The acid (24.9 mmoles, 5.0 g) was dissolved in DMF and cooled to 0°. Potassium carbonate (50 mmoles, 7.0 g) was added. The solution was stirred for 30 minutes. Methyl iodide (50 mmoles, 7.1 g) was added. The reaction was stirred for 5 hours and poured into ethyl acetate and brine. The organic phase was washed with water, dried over sodium sulfate and concentrated. The residue was chromatographed over silica gel eluted with 50% ethyl acetate in hexane. The oil was cooled to 0° C. Trifuoroacetic acid (7 ml) was added. The solution was warmed to room temperature, and azeotroped with xylene co yield 1.49 g of methyl 2-azetidinecarboxylate trifluoroacetic acid salt.

The free amine of methyl 2-azetidinecarboxylate trifluoroacetic acid salt was formed by dissolving the salt in 3 ml DMF and adding diisopropylethyiamine (1.24 mmoles, 0.215 ml). The free amine was then reacted with 2-[5-[2( 2H-tetrazol-5-yl)phenyl]]-1H-benzimidazol-1-yl]octanoic acid (1.24 mmoles, 0.50 g), purified and hydrolyzed as in Example 48 to yield 119 mg, of 1-[1-oxo-2-[5-[2-(2H-tetrazol- 5-yl]phenyl]-1H-benzimidazol-1-yl]octyl-2-azetidinecarboxylic acid (MS).

M. Pt.: 115°–119° C. Calculated for $C_{26}H_{29}N_7O_3 \cdot 1.7$ HCl: C, 56.82; H, 5.63; N, 17.84. Found: C, 56.70; H, 5.47; N, 17.53.

EXAMPLE 44

1-[1-Oxo-2-[5-(2H-tetrazol-5-yl)phenyl]-1H-benzimidazol-1-yl]octyl]-3-pyrrolidinecarboxylic acid A suspension of lithium aluminum hydride (7.50 g) in 150 ml THF was cooled to −5° C. A solution of methyl 1-benzyl-5-oxo-3-pyrrolidine carboxylate (0.064 moles, 15.0 g) in THF was added dropwise. The mixture was heated to 40° C. for 16 hours. Water (25 ml) was added. The mixture was filtered and extracted with ether. The organic phase was washed with water, dried over sodium sulfate and concentrated to yield 11.65 g of N-benzyl-3-hydroxymethylpyrrolidine. (MS) The alcohol (0.06 moles, 11.5 g) in 75 ml 2N sulfuric acid was added dropwise to a stirred solution of chromium dioxide (0.15 moles, 15.0 g) in 100 ml 2N sulfuric acid. The solution was stirred at room temperature for 16 hours. The solution was treated with barium hydroxide hydrate (0.317 mmoles, 100 g) in 250 ml hot water. The solid was filtered and washed with water. The aqueous solution was extracted with ether. Carbon dioxide was bubbled through the solution until the pH was 7.0. The solution was filtered and concentrated to yield 4.5 g of N-benzyl-3-pyrrolidinecarboxylic acid. (MS) The oil was dissolved in 50 ml methanol. Dry HCl gas was bubbled through the solution. The solution was heated to near reflux for 4 hours and concentrated. The residue was neutralized with aqueous sodium bicarbonate. The product was extracted with ether, dried and concentrated to yield 3.0 g of methyl N-benzyl-3-pyrrolidinecarboxylate.

Methyl N-benzyl-3-pyrrolindinecarboxylate (0.0133 moles, 3.0 g) was debenzylated in 15 ml ethanol over 0.6 g of 10% Pd/C, filtered and concentrated. (MS) The amine (1.24 mmoles, 0.5 g), 2-[5-[2(2H-tetrazol-5-yl)phenyl]-1H-benzimidazol-1-yl]octanoic acid (1.24 mmoles, 0.16 g) and 1-hydroxybenzotriazole hydrate (1.24 mmoles, 184 mg) were dissolved in 3 ml DMF, and cooled to 0° C. Dicyclohexylcarbodiimide(1.24 moles, 200 mg) was added. The reaction was stirred for 48 hours and treated as in Example 48 to yield 205 mg, of 1-[1-Oxo-2-[5-(2H-tetrazol-5-yl)phenyl]-1H-benzimidazol-1-yl]octyl]-3-pyrrolidinecarboxylic acid. (MS)

M. Pt.: 121°–127° C. Calculated for $C_{27}H_{31}N_7O_3 \cdot 0.75$ HCl : C, 61.31; H, 6.05; N, 18.54. Found: C, 61.42; H, 5.90; N, 18.45.

EXAMPLE 45

2-[2-Benzyl-5(and 6)-[(2H-tetrazol-5-yl)phenyl-1H-benzimidazol-1-yl]octanoic acid 2-(3,4-Diaminophenyl)benzonitrile (2.4 mmoles, 0.50 g) was dissolved in 3 ml ethanol. Ethyl phenylacetamidate hydrochloride (2.88 mmoles, 0.573 g) (prepared from HCl gas bubbled through benzyl cyanide and ethanol) was added. The reaction was warmed on a steam bath for 10 minutes. Ethyl acetate and brine were added. The organic phase was separated dried and concentrated. The product was precipitated from ethyl acetate and hexane and filtered to yield 290 mg of 2-benzyl-5-(2-cyanophenyl)-1H-benzimidazole. (MS)

M. Pt.: 133°–140° C. Calculated for $C_{21}H_{15}N_3$: C, 81.53; H, 4.89; N, 13.58. Found: C 81.33; H 5.12; N, 13.40.

2-Benzyl-5-(2-cyanophenyl)-1H-benzimidazole (0.81 mmole, 250 mg)was dissolved in 1 ml DMF. Sodium hydride (0.97 mmoles, 40 mg of 60%) was added. The solution was stirred for 10 minutes. Ethyl 2-bromooctanoate (0.97 mole, 242 mg) was added. After stirring for 20 minutes, ether was added. The organic phase was washed with saturated ammonium chloride, dried over sodium sulfate and concentrated. The residue was dissolved in tributyltinazide (2.0 mmoles, 0.7 g) and heated at 85° C. for 32 hours. The reaction mixture was chromatographed over silica gel eluted with 100% hexane in ether, and then ethyl acetate. The material was hydrolyzed with 2 ml of 2N NaOH. The aqueous phase washed with ether. The pH was adjusted to 4.0 using 2N HCl. The precipitate was collected and dried. The regioisomers were separated by reverse phase HPLC to yield 38 mg of 2-[2-Benzyl-5-[2-(2H-tetrazol-5-yl)phenyl-1H-benzimidazol-1-yl]octanoic acid and 46 mg 2-[2-Benzyl-6-[2-(2H-tetrazol-5-yl)phenyl-1H-benzimidazol-1-yl]octanoic acid. (MS)

Calculated for $C_{29}H_{30}N_6O_2 \cdot 1.5 H_2O$: C, 66.78; H, 6.38; N, 16.11. Found: C, 66.96; H, 6.61; N, 15.25.

EXAMPLE 46

1-[1-Oxo-2-[5-[2(2H-tetrazol-5-yl)phenyl]indol-1-yl]-4-hydroxy-L-proline

4-Hydroxy-L-proline lactone hydrobromide (0.88 mmoles, 170 mg-Example 13) in DMF was reacted with diisopropylethylamine (0.101 ml), and then reacted with 2-[5-[2-(2H-tetrazol-5-yl)phenyl]indol-1-octanoic acid (0.74 mmoles, 300 mg, Example 20), dicyclohexylcarbodiimide, and hydroxybenzotriazole. The resulting nitrile ester was converted to the tetrazole and hydrolyzed as in Example 13 yield 75 mg of 1-[1-Oxo-2-[5-[2-(2H-tetrazol-5-yl)phenyl]indol-1-yl]-4-hydroxy-L-proline. (MS)

M. Pt.: 122°–128° C. Calculated for $C_{28}H_{32}N_6O_4$: C, 65.10; H, 6.24; N, 16.27. Found: C, 65.00; H, 6.26; N, 15.99.

EXAMPLE 47

2-[5-(2-Carboxyphenyl)-4-aza-1H-benzimidazol-1-yl]octanoic acid

2'-Bromoacetophenone(0.1 moles, 20.0 g) was reacted with sodium methoxide (0.13 moles) in 150 ml methanol and treated with Gold's Reagent (0.13 moles, 21.2 g) according to the procedure in *J. Org. Chem.* 45: 4525 (1988). The intermediate was purified by chromatography over silica gel eluted with 75–100% ethyl acetate in hexane. The resulting amine was dissolved in ethanol with 1,1-bis(methylthio)-2-nitroethylene (0.074 moles, 12.3 g) and sodium acetate (22.5 g) and refluxed for two hours. An additional 45 g of sodium acetate was added. The solution continued to reflux for 16 hours. The reaction was concentrated. Ethyl acetate and water were added. The organic phase was dried and evaporated. The product was chromatographed over silica gel eluted with a gradient of 25–100% ethyl acetate in hexane to yield 2.6 g of 2-amino-6-(2-bromophenyl)-3-nitropyridine. (MS)

Calculated for $C_{11}H_8BrN_3O_2$: C, 44.92; H, 2.74; N, 14.29. Found: C, 44.96; H, 2.64; N, 14.11.

2-Amino-6-(2-bromophenyl)-3-nitropyridine (8 mmoles, 2.5 g) was refluxed for 16 hours with copper cyanide (8.8 mmoles, 0.80 g) in 50 ml DMF. The reaction was cooled, extracted with ethyl acetate and water, and filtered. The organic phase was dried and concentrated. (MS) The nitro group was reduced by hydrogenation in ethyl acetate and ethanol (1:1) over 1.01 g of 5% Pd/C. The reaction was filtered and concentrated. The diamine (3.33 mmoles, 700 mg) was refluxed in 50 ml formic acid for 2 hours. Water and ethyl acetate were added. The pH was adjusted to 9.5 using 2N NaOH. The solution was dried, and the ethyl acetate evaporated. The intermediate was taken up in ethanol and filtered. The ethanol solution was concentrated under vacuum to yield 700 mg of ethyl 2-[5-(2-Carboxyphenyl)-4-aza-1H-benzimidazol-1-yl]octanoate. (MS)

The azabenzimidazole (3 moles, 660 mg) was dissolved in DMF. Sodium hydride (3 mmoles, 120 mg of 60% in mineral oil) was added. Ethyl 2-bromooctanoate (3 mmoles, 717 mg) was added. The reaction was stirred for 16 hours. The reaction was extracted with ethyl acetate added and washed with water. The ethyl acetate was dried and evaporated. The intermediate was purified by chromatography over silica gel eluted with a gradient of 25–50% ethanol in ethyl acetate to yield 52 mg of ethyl 2-[5-(2-carboxyphenyl)-4-aza-1H-benzimidazol-1-yl]octanoate 214 mg) and 214 mg of the Ethyl 2-[6-(2-carboxyphenyl)-4-aza-1H-benzimidazol-1yl]octanoate. (MS)

Calculated for $C_{23}H_{35}N_3O_7 \cdot 0.4H_2O$: C, 57.37; H, 7.33; N, 8.73. Found: C, 57.97; H, 6.71; H, 8.75.

The ester was heated on a steam bath for 30 minutes in 10 ml ethanol and 1 ml 5N NaOH, cooled, and concentrated. Water was added. The solution was washed with ethyl acetate. The pH was adjusted to 3.0 using 2N HCl. The product was extracted with ethyl acetate, dried and concentrated to yield 17 mg of 2-[5-(2-Carboxyphenyl)-4-aza-1H-benzimidazol-1-yl]octanoic acid. (MS)

Calculated for $C_{21}H_{23}N_3O_4 \cdot 1.3\ H_2O$: C, 62.30; H, 6.38; N, 10.38. Found: C, 62.64; H, 6.13; N, 10.08.

EXAMPLE 48

1-[1-Oxo-2-[5-[2-(2H-tetrazol-5-yl)phenyl]-1H-benzimidazol-1-yl]octyl]-4-cis-phenoxy-L-proline N-Carbobenzyloxy-4-trans-hydroxy-L-proline methyl ester (35.84 mmole, 0.0 g) was dissolved in 100 ml of THF and cooled to 0° C. Phenol (51.96 mmoles, 4.90 g) and triphenylphosphine (51.96 mmoles, 13.82 g) were added. Diethylazodicarboxylate (51.96 moles, 9.44 ml) was added dropwise over 1 hour while maintaining the temperature from 0° to −5° C. The reaction stirred at room temperature for 16 hours. The solution was concentrated. 50% Ether in hexane was added. The solid was filtered. The solution was concentrated to a yellow oil. The oil was chromatographed over silica gel eluted with a gradient of 20–40% ether in hexane to yield 3.01 g of N-Carbobenzyloxy-4-cis-phenoxy-L-proline methyl ester. (MS)

Calculated for $C_{20}H_{21}NO_5$: C, 67.59; H, 5.96; N, 3.94. Found: C, 67.29; H, 6.00; N, 4.00.

N-carbobenzyloxy-4-cis-phenoxy-L-proline methyl ester was hydrogenated in ethyl acetate over 5% Pd/C, filtered and concentrated. The amine (3.24 moles, 716 mg), 2-[5-[2-(2H-tetrazol-5-yl)phenyl]-1H-benzimidazol-1-yl]octanoic acid (3.24 mole, 733 mg) and hydroxybenzotriazole (3.56 mmoles, 480 mg) were dissolved in 4 ml DMF. Dicyclohexylcarbodiimide (3.56 mmoles, 733 mg) was added. The solution was stirred overnight. Ethyl acetate was added. The solution was filtered, washed with water, dried and concentrated. The ester was chromatographed over silica gel eluted with 1–3% methanol in chloroform. The mixture of stereoisomers was chromatographed by reverse phase HPLC eluted with 40% acetontrile in water with 1% ammonium acetate. Each ester was hydrolyzed by stirring in 1ml of 2N NaOH for 1 hour at room temperature. The solution was filtered. The pH was adjusted to 3.5 with 1N HCl. The solid was collected and dried to yield 1-[1-oxo-2-[5-[2-(2H-tetrazol-5-yl]phenyl]-1H-benzimidazol-1-yl]octyl]-4-cis-phenoxy-2-pyrrolidine carboxylic acid.

Isomer A: 220 mg (MS)

M. Pt.: 160°–165° C. Calculated for $C_{33}H_{35}N_7O_4 \cdot 1.5$ HCl: C, 61.13; H, 5.67; N, 15.12. Found: C, 61.05; H, 5.56; N, 14.96.

Isomer B: 250 mg (MS)

M. Pt.: 158°–165° C. Calculated for $C_{33}H_{35}N_7O_4 \cdot 1.3$ HCl: C, 61.83; H, 5.71; N, 15.29. Found C, 61.99; H, 5.59; N, 15.07.

EXAMPLE 49

1-[1-Oxo-2-[5-[2-(2H-tetrazol-5-yl]phenyl]-1H-benzimidazol-1-yl]octyl-4-cis-4-fluorophenoxy-L-proline.

N-Carbobenzyloxy-4-trans-hydroxy-L-proline methyl ester (35.84 mole, 10.0 g) was converted to the cis-4-fluorophenoxy derivative following Example 40 to yield 2.20 g of N-carbobenzyloxy 4-cis-4-fluorophenoxyphenyl-L-proline methyl ester.

N-Carbobenzyloxy-4-cis-4-fluorophenoxyphenyl-L-proline methyl ester was hydrogenated and reacted with 2-[5-[2-(2H-tetrazol-5-yl)phenyl]-1H-benzimidazol-1-yl]octanoic acid (1.24 mmole, 0.50 g) following the procedure in Example 48 to yield 127 mg of 1-[-1-Oxo-2-[5-[2-(2H-tetrazol-5-yl]phenyl]-1H-benzimidazol-1-yl]octyl]-4-cis-4-fluorophenoxy-L-proline. (MS)

M. Pt.: 131°–140° C. Calculated for $C_{33}H_{34}N_7O_4F \cdot 1.5\ H_2O$: C, 59.48; H, 5.37; N, 14.71. Found: C, 59.71; H, 5.16; N, 14.57.

EXAMPLE 50

1-[1-Oxo-2-[5-[2-(2H-tetrazol-5-yl)phenyl]-1H-benzimidazol-1-yl]-7-trifluoromethylhexyl]-4-cis-phenoxy-L-proline.

Ethyl acetoacetate was reacted with sodium hydride and 4-trifluoromethylbutyl bromide and then brominated with N-Bromosuccinimide as in Example 11 to yield ethyl 2-Bromo-7-trifluoromethylhexanoate.

5-(2-Cyanophenyl)-1H-benzimidazole was reacted with sodium hydride and ethyl 2-bromo-7-trifluoromethylhexanoate. The nitrile ester was converted to the tetrazole with tributyltinazide and hydrolyzed with sodium hydroxide as in Example 8 to yield 7-trifluoromethyl-2-[5-[2-(2H-tetrazol-5-yl)phenyl]-1H-benzimidazol-1-yl]octanoic acid.

7-Trifluoromethyl-2-[5-[2-(2H-tetrazol-5-yl)phenyl]-1H-benzimidazol-1-yl]octanoic acid (1.69 mmoles, 0.750 g) was reacted with cis-phenoxy-L-proline methyl ester (2.19 mmoles, 523 mg), hydroxybenzotriazole (1.86 mmoles, 250 mg) and dicyclohexylcarbodiimide (1.86 mmoles, 380 mg) in 5 ml DMF as in Example 48. The resulting ester was hydrolyzed with sodium hydroxide to yield 526 mg of 1-[1-oxo-2-[5-[2-(2H-tetrazol-5-yl)phenyl]-1H-benzimidazol-1-yl]-7-trifluoromethylhexyl]-4-cis-phenoxy -L-proline. (MS).

Calculated for $C_{32}H_{30}N_7O4F_3 \cdot 0.9$ HCl: C, 57.67; H, 4.67; N, 14.71. Found: C, 57.80; H, 4.60; N, 14.60.

EXAMPLE 51

1-[1-Oxo-2-[5-[2-(2H-tetrazol-5-yl)phenyl]-1H-benzimidazol-1-yl]octyl-4-trans-phenoxy-L-proline N-carbobenzyloxy-4-cis-hydroxy-L-proline methyl ester (24.20 mmoles, 6.75 g) was dissolved in 100 ml THF and cooled to 0° C. Triphenylphosphine (35.1 mmoles, 9.33 g) and then phenol (35.1, 3.31 g) were added followed by dropwise addition of diethylazodicarboxylate (35.1 mmoles, 6.40 ml) over 1 hour. The reaction was stirred for 48 hours at room temperature. The solvent was removed. The residue was dissolved in ether and filtered. The filtrate was concentrated and chromatographed over silica gel eluted with a gradient of 10–25% ethyl acetate in hexane to yield 4.12 g of N-carbobenzyloxy-4-trans-phenoxy-L-proline methyl ester.

N-Carbobenzyloxy-4-trans-phenoxy-L-proline methyl ester was hydrogenated and reacted with 2-[5-[2-(2H-tetrazole-5-yl)phenyl]-1H-benzimidazole-1-yl]octanoic acid (1.1 mmole, 400 mg) as in Example 48 to yield 196 mg of 1-[1-Oxo-2-[5-[2-(2H-tetrazol-5-yl)phenyl]-1H-benzimidazol-1-yl]octyl-4-trans-phenoxy-L-proline. (MS)

M. Pt.: 128°–133° C. Calculated for $C_{33}H_{35}N_7O_4 \cdot 0.5$ HCl: C, 64.77; H, 5.85; N, 16.02. Found: C, 64.82, H, 5.95 N, 16.26

EXAMPLE 52

1-[1-Oxo-2-[5-[2[-2H-tetrazol-5-yl]phenyl]-1H-benzimidazol-1-yl]octyl]-4-cis-thiophenoxy-L-proline Triethylamine (0.06 moles, 8.4 ml), p-toluenesulfonyl chloride (0.04 moles, 7.75 g of 98%) and 4-dimethyaminopyridine (146 mg) were added to N-carbobenzyloxy-4-trans-hyrdroxy-L-proline methyl ester (0.04 moles, 11.1 g) in 75 ml CHCL$_3$. The reaction was stirred at room temperature for 23 hours, poured into ice water, washed with water, dried and concentrated. The residue was chromatographed over silica gel eluted with 25–40% ethyl acetate in hexane. The resulting tosylate (23.2 mmoles, 10 g) was added to a solution of sodium (50 mmoles, 1.15 g) in ethanol (60 ml) with thiophenol (49.0 mmoles, 5.4 g) and stirred for 16 hours. The reaction was concentrated; water and methylene chloride were added. The organic phase was washed with saturated sodium bicarbonate and water, dried over sodium sulfate and concentrated. The residue was purified by chromatography over silica gel eluted with 20% ethyl acetate in hexane to yield 6.0 g of N-carbobenzyloxy-4-cis-thiophenoxy-L-proline methyl ester.

N-carbobenzyloxy-4-cis-thiophenoxy-L-proline methyl ester(16.5 mmole, 6.02 g) was dissolved in 18 ml 1N sodium hydroxide, 30 ml methanol and 5 ml THF, and stirred for 16 hours at room temperature. The reaction was concentrated. Water and ether were added. The aqueous layer was acidified using 2N HCl and extracted with ethyl acetate. The ethyl acetate solution was dried and evaporated to yield N-carbobenzyloxy-4-cis-thiophenoxy-L-proline methyl ester (MS).

The carbobenzyloxy was removed by dissolving the acid (1.877 g, 16.5 mmoles) in glacial acetic acid and HBr and refluxing for I hour. The reaction was concentrated. Isopropanol was added twice and evaporated to yield 4.1 g of oil which still contained some isopropanol. The acid was dissolved in methanol and cooled to −30° C. Concentrated HCl (1.55 ml) was added. The reaction was stirred cold for 2 hours and at room temperature for 24 hours. The reaction was concentrated. Water was added, 10% sodium bicarbonate was added. The product was extracted with methylene chloride, dried and evaporated to yield 1.97 g of 4-cis-thiophenoxy-L-proline methyl ester.

4-Cis-thiophenoxy-L-proline methyl ester (1.75 mmoles, 465 mg) was reacted with 2-[5-[2-(2H-tetrazol-5-yl)phenyl]-1H-benzimidazol-1-yl]octanoic acid (1.24 mmoles, 0.5 g) and hydrolyzed according to Example 48 to yield 308 mg of 1-[1-Oxo-2-[5-[2-[2H-tetrazol-5-yl]phenyl]-1H-benzimidazol-1-yl]octyl]-4-cis-thiophenoxy-L-proline. (MS)

M. Pt.: Dec. 140° C. Calculated for $C_{33}H_{35}N_7O_3S \cdot 0.75$ HCl: C, 62.21; H, 5.66; N, 15.39. Found: C, 62.25; H, 5.71; N, 15.08.

EXAMPLE 53

1-[1-Oxo-2-[5-[2-(2H-tetrazol-5-yl)phenyl]-1H-benzimidazol-1-yl]octyl-4-cis-phenylsulfone-L-proline 1-[1-Oxo-2-[5-2-(2H-tetrazol-5-yl)phenyl]-1H-benzimidazol-1-yl]octyl]-4-cis-thiophenoxy-L-proline (0.165 mmoles, 100 mg.) was dissolved in 2 ml methanol and cooled in an ice bath. Sodium periodate (0.198 mmoles, 43 mg) in 0.5 ml water was added. The reaction was stirred at room temperature overnight, filtered and concentrated. The residue was dissolved in a trace of methanol and ethyl acetate added to yield 51 mg of 1-[1-Oxo-2-[5-[2-(2H-tetrazol- 5-yl]phenyl]-1H-benzimidazol-1-yl]octyl-4-cis-phenylsulfone-L-proline. (MS)

EXAMPLE 54

1-[1-Oxo-2-[5-[2-(2H-tetrazol-5-yl)phenyl]-1H-benzimidazol-1-yl]octyl]-4-cis-(3-pyridyloxy)-L-proline N-Carbobenzyloxy-4-trans-hydroxy-L-proline methyl ester (17.9 mmoles, 5.0 g) was converted according to Example 48 to yield 2.93 g of N-Carbobenzyloxy-4-cis-3-pyridyloxy-L-proline methyl ester.

N-Carbobenzyloxy-4-cis-3-pyridyloxy-L-proline methyl ester was deprotected, reacted with 2-[5-[2-(2H-tetrazol-5-yl)phenyl]1H-benzimidazol-1-yl]octanoic acid (1.24 mmole, 0.50 g) as in Example 48. The stereoisomers were separated by chromatography over silica gel eluted with a gradient of 3–10% methanol in CHCl$_3$. Each ester was hydrolyzed as in Example 48 to yield 1-[1-Oxo-2-[5-[2-[(2H-tetrazol-5-yl]phenyl]-1H-benzimidazol-1-yl]octyl]-4-cis-(3-pyridyloxy)-L-proline.

Isomer A: 157 mg (MS)

M. Pt.: Dec. 230° C. Calculated for $C_{32}H_{34}N_8O_4 \cdot 0.68$ HCl: C, 62.05; H, 5.64; N, 18.09; Found: C, 62.11; H, 5,80; N, 17.86.

Isomer B: 227 mg (MS)

M. Pt.: Dec. 230° C. Calculated for $C_{32}H_{34}N_8O_4 \cdot 0.68$ HCl: C, 62.05; H, 5.64; N, 18.09. Found C, 62.07; H, 5.77; N, 18.02.

EXAMPLE 55

N-[1-oxo-2-[5-[2-(2H-tetrazole-5-yl]phenyl]-1H-benzimidazol-1-yl]octyl]-L-phenylalanine L-Phenylalanine hydrochloride (1.75 mmoles, 380 mg), diisopropylethylamine (1.93 mmoles, 0.34 mi), 2-[5-[2-(2H-tetrazol-5-yl)phenyl]-1H-benzimidazol-1-yl]octanoic acid (1.24 mmoles, 0.50 g), hydroxybenzotriazole (1.36 mmoles 184 mg) and dicyclohexylcarbodiimide (1.36 mmoles, 280 mg) were reacted as in Example 37. The stereoisomers were separated by chromatography over silica gel eluted with 2% methanol in chloroform. The isomers were hydrolyzed as in Example 37 to yield N-[1-oxo-2-[5-[2-(2H-tetrazole-5-yl) phenyl]-1H-benzimidazol-1-yl]octyl]-L-phenylalanine.

Isomer A: 187 mg (MS)

M. Pt.: 5 Dec. 165° C. Calculated for $C_{31}H_{33}N_7O_3.0.9$ HCl: C, 63.75; H, 5.85; N, 16.79. Found: C, 63.86; H, 6.00; N, 16.09.

Isomer B: 80 mg (MS).

M. Pt.: Dec. 160° C.

Calculated for $C_{31}H_{33}N_7O_3.0.89$ HCl: C, 63.75; H, 5.85; N, 16.79. Found: C, 63.76; H, 5.85; N, 16.70.

EXAMPLE 56

1-[1-Oxo-2-[5-[2-(2H-tetrazol-5-yl)phenyl-1H-benzimidazol-1-yl]octyl]-4-phenyl-L-proline.

Phenylmagnesium bromide (0.180 mole, 60 ml of 3M in ether) was added at 0° C. to N-carbobenzyloxy-4-keto-L-proline (0.0722 moles, 19.0 g) in 300 ml THF and stirred overnight at room temperature. Ammonium chloride 400 ml of was added with cooling and acidified to pH 3.0 using 5N HCl. The intermediate was extracted with ethyl acetate, dried and concentrated. The residue was dissolved in 2N NaOH, washed with enter, and acidified with 2N HCl. The intermediate was extracted with ethyl acetate, dried and concentrated to yield N-carbobenzyloxy-4-cis-phenyl-trans-hydroxy-L-proline. (MS)

The alcohol (0.022 moles, 7.60 g) was refluxed in 20 ml trifluoroacetic acid and 20 ml dichloromethane. The solution was concentrated and dissolved in ether. The solution was cooled at 0° C., treated with diazomethane and concentrated. The residue was chromatographed over silica gel eluted with ethyl acetate in hexane to yield 4.25 g of N-carbobenzyloxy-4-cis-phenyl-L-proline methyl ester. (MS) The ester was dissolved in 5 ml ethyl acetate and 25 ml methanol and hydrogenated at 32 psi over 250 mg of 5% Pd/C for 2.5 hours. The solution was filtered through celite, and concentrated to yield 450 mg of 4-cis-phenyl-L-proline methyl ester.

4-cis-Phenyl-L-proline methyl ester (1.63 mmoles, 0.33 g), 2-[5-[2-(2H-tetrazol-5-yl)phenyl-1H-benzimidazol-1-yl] octanoic acid (1.24 mmoles, 0.50 g), hydroxybenzotriazole (1.36 mmoles, 184 mg) and dicyclohexylcarbodiimide (1.36 mmoles, 280 mg) in DMF were reacted, purified and hydrolyzed as in Example 13 to yield 270 mg of 1-[1-Oxo-2-[5-[2-(2H-tetrazol-5-yl)phenyl-1H-benzimidazol-1-yl]octyl]-4-phenyl-L-proline. (MS)

M. Pt.: 160°–164° C. Calculated for $C_{33}H_{35}N_7O_3.1.5$ HCl: C, 63.20; H, 5.87; N, 15.63. Found: C, 63.17; H, 5.77; N, 15.41.

EXAMPLE 57

1-[1-Oxo-2-[5-[2-(2H-tetrazol-5-yl)phenyl]-1H-benzimidazol-1-yl]octyl-4-benzyl-L-proline.

Benzyl triphenyl phosphonium bromide (0.15 moles, 66.07 g) was added portionwise to a suspension of sodium hydride (0.15 moles, 6.0 g of 60% in mineral oil) in 350 ml DMSO and heated at 70°–80° C. until dissolved. The solution was cooled. N-Carbobenzyloxy-4-keto-L-proline (0.025 moles, 13.2 g) in 50 mi DMSO was added dropwise. The solution was heated at 70° for 4 hours and stirred at room temperature overnight. A solution of 15 g potassium bicarbonate in 1 l of water was added. The solution was washed with ether and acidified to pH 4 0 using 2N HCl. The product was extracted with chloroform. The chloroform solution was dried and concentrated. The resulting oil was triturated with ether. The ether solution was extracted with 10% sodium bicarbonate. The aqueous layer was acidified with 2N HCl. The acid was extracted with ether. The organic solution was dried and concentrated. (MS) The acid (5.9 mmoles, 2.0 g) in ether was esterified at 0° C. with an excess of diazomethane and chromatographed over silica gel eluded with ethyl acetate in hexane. The protecting group was removed by dissolving the ester (2.7 mmoles, 0.9 g) in 20 ml methanol and hydrogenating over Pd/C (200 mg) for 4 hours at 30 psi. The solution was filtered through celite and concentrated co yield 400 mg of 4-benzyl-L-proline methyl ester. (MS)

4-Benzyl-L-proline methyl ester (1.75 mmoles, 381 mg), 2-[5-[2-(2H-Tetrazol-5-yl)phenyl]-1H-benzimidazol-1-yl] octanoic acid (1.24 mmoles, 0.50 g), hydroxybenzotriazole (1.36 mmoles, 184 mg) and dicyclohexylcarbodiimide (1.36 mmoles, 280 mg) were dissolved in 1.5 ml DMF, purified and hydrolyzed as in Example 13 to yield 240 mg of 1-[1-Oxo-2-[5-[2-(2H-tetrazol-5-yl)phenyl]-1H-benzimidazol-1-yl]octyl-4-benzyl-L-proline. (MS)

M. Pt.: 127°–131° C. Calculated for $C_{34}H_{37}N_7O_3. 0.5 H_2O$: C, 67.98; H, 6.35; N, 15.91. Found: C, 68.13; H, 6.35; N, 15.91.

EXAMPLE 58

1-[1-oxo-2-[5-[2-(2H-tetrazol-5-yl)phenyl]-1H-benzimidazol-1-yl]octyl]-4-cis-benzyloxy-L-proline 4-cis-Benzyloxy-2-L-proline methyl ester (prepared in a method analogous to 4-cis-phenoxy-L-proline methyl ester in Example 48 was reacted with 2-[5-[2-(2H-tetrazol-5-yl)phenyl]-1H-benzimidazol-1H-yl]octanoic acid, purified and hydrolyzed as in Example 48 to yield 420 mg of 1-[1oxo-2-[5-[2-(2H-tetrazol-5-yl)phenyl]-1H-benzimidazol-1-yl]octyl]-4-cis-benzyloxy-L-proline. (MS)

M. Pt.: 149°–155° C. (mixture) Calculated for $C_{34}H_{37}N_7O_3.1.3$ HCl: C, 62.34; H, 5.89; N, 14.97. Found: C, 62.33; H, 5.83; N, 14.82.

EXAMPLE 59

1-[1-Oxo-2-[5-2-(2H-tetrazol-5-yl)phenyl]-1H-benzimidazol-1-yl]octyl]-4,4-dimethoxy-L-proline N-Carbobenzyloxy-4-keto-L-proline (7.3 mmoles, 2.0 g—see Example 40) and p-toluenesulfonic acid (35 mg) were dissolved in 60 ml methanol and refluxed for 16 hours. A Dean-Stark trap was added. The water was removed. The mixture was poured into ice water and extracted with ethyl acetate. The organic phase was dried and concentrated. The product was deprotected by hydrogenation in ethyl acetate over 0.5 g Pd/C at 40 psi for 1 hour. The solution was filtered and concentrated to yield 880 mg of 4,4-dimethoxy-L-proline methyl ester. (MS)

4,4-Dimethoxy-L-proline methyl ester (1.35 mmoles, 0.257 g) and 2-[5-[2-(2H-tetrazol-5-yl)phenyl]-1H-benzimidazol- 1-yl]octanoic acid (1.23 mmoles, 0.5 g) were reacted in the presence of hydroxybenzotriazole and dicyclohexylcarbodiimide as in Example 15 to yield 0.220 g of 1-[1-oxo-2-[5-2-(2H-tetrazol-5-yl)phenyl]-1H-benzimidazol-1-yl]octyl]-4,4-dimethoxy-L-proline. (MS).

Calculated for $C_{28}H_{36}N_7O_5.H_2O$: C, 60.10; H, 6.39; N, 16.92. Found: C, 60.36; H, 6.24; N, 17.37.

EXAMPLE 60

2-[5-[2-(2H-Tetrazol-5-yl)phenyl]-1H-benzimidazol-1-yl]-6-methyl-5-heptenoic acid.

Sodium hydride was added portionwise to a stirred solution of ethyl acetoacetate (0.1 mole, 13.0 g) in 300 ml THF. The solution was stirred for 30 minutes. 5-Bromo-2-methyl-2-pentene (0.11 moles, 17.9 g) was added dropwise over 30 minutes. The solution stirred at room temperature for 40 hours. The solution was concentrated in vacuo. Ethyl acetate and water were added. The organic phase was dried over sodium sulfate and concentrated. The product was purified by HPLC over silica gel eluted with a gradient of 0–40% ethyl acetate in hexane to yield 4.5 g of ethyl 2-acetyl-6-methyl-5-heptenoate.

Ethyl 2-acetyl-6-methyl-5-heptenoate (0.016 moles, 3.5 g.) was treated with sodium methoxide and the N-bromosuccinimide as in the procedure in Example 16 to yield 2.1 g of methyl 2-bromo-6-methyl-5-heptenoate.

Methyl 2-bromo-6-methyl-5-heptenoate (6.34 mmoles, 1.49 g) was added to a solution of 5-(2-cyanophenyl)-1H-benzimidazole (6.44 mmoles, 1.41 g) and sodium hydride (7.75 mmoles, 0.31 g of 60% in mineral oil) as in the procedure in Example 16 to yield 1.5 g of methyl 2-[5(and6)-(2-cyanophenyl)-1H-benzimidazol-1-yl]-6-methyl-5heptenoate. (MS)

Methyl 2-[5(and6)-(2-cyanophenyl)-1H-benzimidazol-1-yl]-6-methyl-5-heptenoate (4.02 mmoles, 1.5 g) was dissolved in tributyltinazide (3 ml), converted to the tetrazole and purified as in the procedure in Example 33 to yield 0.31 g of methyl 2-[5-[2-(2H-Tetrazol-5-yl)phenyl]-1H-benzimidazol-1-yl]-6-methyl-5-heptenoate.

Methyl 2-[5-[2-(2H-tetrazol-5-yl)phenyl]-1H-benzimidazol-1-yl]-6-methyl-5-heptenoate 0.7 mmoles, 0.30g) was hydrolyzed as the procedure in Example 33 to yield 0.22 g of 2-[5-[2-(2H -tetrazol-5-yl)phenyl]-1-H-benzimidazol-1-yl]-6-methyl-5-heptenoic acid.

Calculated for $C_{22}H_{22}N_6O_2$: C, 65.66, H, 5.51; N, 20.88. Found: C, 65.76; H, 5.55; N, 20.70.

EXAMPLE 61

1-[5(and 6)-[2-(2H-2H-Tetrazol-5-yl)phenyl]-2-pentyl-1H-benzimidazol- 1-yl]acetic acid 2-(3,4-Diaminophenyl)benzonitrile (4.3 mmoles, 0.9 g) and ethyl hexanoamidate hydrochloride were dissolved in 20 ml ethanol and stirred for 2.5 hours. The solvent was removed in vacuo. The residue was dissolved in ethyl acetate and washed with water, saturated $NaHCO_3$ and brine. The organic phase was dried and concentrated. The residue was chromatographed on silica gel eluted with 1:1 ethylacetate/hexane to yield 1.0 g of 5-(2-Cyanophenyl)-2-pentyl-1H-benzimidazole.

5-(2-Cyanophenyl)-2-pentylbenzimidazole (3.46 mmoles, 1.0 g) was dissolved in 20 ml DMF. Sodium hydride (4.75 mmoles, 0.19 g of 60 % in mineral oil) was added. The solution was stirred for 20 minutes. Ethyl bromoacetate (5.2 mmoles, 0.58 ml) was added. The solution was stirred for 30 minutes. The mixture was poured into water and extracted with ethyl acetate. The ethyl acetate was washed with brine, dried and concentrated to yield 1.2 g of oil. The oil was dissolved in 10 ml of tributyltinazide and heated at 90° C. for 48 hours. Acetonitrile, water, and acetic acid (90 ml of 8:1:1) were added to the solution. The solution was stirred for 1 hour and washed 5 times with 200 ml portions of hexane. The acetonitrile solution was concentrated. The residue was dissolved in ethyl acetate and washed with brine, dried over sodium sulfate and concentrated. The residue was dissolved in 10 ml methanol and precipitated with 100 ml ethyl acetate. The solid was collected and dried to produce 1-[5(and 6)-[2-(2H-Tetrazol-5-yl)phenyl]-2-pentyl-1H-benzimidazol-1-yl]acetic acid. (NMR). (MS).

EXAMPLE 62

1-[1-Oxo-2-[5-[2-(1H-tetrazol-5-yl]phenyl]-1H-benzimidazol-1-yl]octyl]4-cis-(4-hydroxyphenoxy)-L-proline N-Carbobenzyloxy-4-cis-(4-t-butoxyphenoxy)-L-proline methyl ester was prepared as in Example 48. (MS)

Calculated for $C_{24}H_{29}NO_6$: C, 67.43; H, 6.84; N, 3.28. Found: C, 67.15; H, 6.84; N, 3.30.

N-Carbobenzyloxy-4-cis-(4-t-butoxyphenoxy)-L-proline methyl ester (2.48 moles) was deprotected and reacted with 2-[5-[2-(2H-tetrazol-5-yl)phenyl]2H-benzimidazole-1-yl] octanoic acid (2.48 moles, 1.0 g), hydroxybenzotriazole (2.73 moles, 368 mg) and dicyclohexylcarbodiimide (2.73 mmoles, 560 mg) as in Example 48. The ester was dissolved in 5 ml of 2% anisole in trifluoroacetic acid and stirred at room temperature for 3 hours. After concentrating the reaction, the ester was hydrolyzed as in Example 48. The stereoisomers were separated. (MS)

Calculated for $C_{33}H_{35}N_7O_5.0.5$ HCl: C,63.12; H, 5.67; N, 15.59. Found: C,63.12; H, 5.67; N, 15.61.

EXAMPLE 63

1-[1-Oxo-2-[5-[2-(1H-tetrazol-5-yl]phenyl]-1H-benzimidiazol-1-yl]octyl]-4-cis-(4-methoxyphenoxy)-L-proline.

N-Carbobenzyloxy-4-cis-(4-methoxyphenoxy)-L-proline methyl ester was prepared as in Example 48. (MS)

Calculated. for $C_{21}H_{23}NO_6$: C, 65.44; H, 6.01; N, 3.63. Found: C, 65.40; H, 6.07; N, 3.90.

1-[1-Oxo-2-[5-[2-(1H-tetrazol-5-yl]phenyl]-1H-benzimidazol-1-yl]octyl]-4-cis-4-methoxyphenoxy)-L-proline was prepared as in Example 48. (MS).

M. Pt.: 162°–170° C. Calculated for $C_{34}H_{37}N_7O_5$: C, 65.48; H, 5.98; N, 15.72. Found: C, 65.74; H, 5.97; N, 15.64.

The following compounds were prepared in a manner analogous to Example 12:

EXAMPLE 64

2-[1-[5-[2-(2H-Tetrazol-5-yl)phenyl]-
1H-benzimidazol-1-yl]hexyl]-1-
(2H-tetrazol-5yl)methyl imidazole (MS)

Yield: 26% Calculated for $C_{25}H_{26}N_{12}$: C, 60.46; H, 5.42; N, 21.68 Found: C, 60.48; H, 5.42; N, 20.89

EXAMPLE 65

2-[1-[5-[2-(2H-Tetrazol-5-yl)phenyl]-
1H-benzimidaozyl-1-yl]pentyl]-1H-imidazole-1-acetic acid (MS)

Yield: 34% Calculated for $C_{24}H_{24}N_8C_2H_4O_2$: C, 58.47; H, 5.45; N, 30.30 Found: C, 57.93; H, 5.29; N, 30.16.

The following compounds were prepared in a manner analoguous to Example 48:

EXAMPLE 66

1-[1-Oxo-2-[5-[2-(1H-tetrazol-5-yl)phenyl]-
1H-benzimidazol-1-yl]octyl]-4-cis-
(4-carboxymethylphenoxy)-L-proline (MS)

M. Pt.: 159°–169 ° C. dec. Calculated for $C_{35}H_{37}N_7O_6 \cdot 0.32$ HCL: C, 63.37; H, 5.67; N, 14.78 Found: C, 63.38; H, 5.78; N, 14.79

The compounds of Formula I are potent effective antagonists of angiotensin II. The ability of representative compounds of Formula I to block angiotensin II receptor binding was determined using the adrenal glomerulosa assay. The ability to antagonize angiotensin-induced vasoconstriction was evaluated in the rabbit aorta test system.

Adrenal Glomerulosa Test System

Binding of $I^{125}$-angiotensin II to adrenal membranes was routinely carried out in 96-well filtration plates. Adrenal membranes were prepared from the capsular portion (glomerulosal layer attached) of rat adrenal glands by differential centrifugation. Briefly, capsules were homogenized in a solution containing sucrose, 250 mM; $MgCl_2$, 1 mM; and tris, 5 mM at pH 7.5 and 4° C. using a polytron at setting 5 for 20 seconds. The homogenate was stirred gently for 15 minutes at 4° C. and then centrifuged 10 minutes, at 1000×g, 4° C. The supernatant was centrifuged 30 minutes, at 30,000×g, 4° C., and the resulting pellet resuspended in 50 mM tris. Membrane preparations were stored in aliquots at −70° C. until used. Binding of $I^{125}$-angiotensin II to adrenal membranes was performed at room temperature for 90 minutes in 96-well plates containing a hydrophilic polyvinylidene fluoride membrane (0.45 μm, Millipore-GV multiscreen). Each 250 μl incubate contained the following (final concentration): tris, 50 mM; NaCl, 120 mM; $MgCl_2$, 5mM; dithiothrietol 1 mM; bovine serum albumin, 0.05%; $I^{125}$-angiotensin II, 0.1 nM; and adrenal membrane protein, 8–15 μg. Antagonists were added in concentrations from 10 nM to 100 μM. Non-specific binding was measured in the presence of 0.1 μM $Sar_1$, $Ile_8$ angiotensin II. Binding was terminated by vacuum filtration. Receptor-ligand complex trapped on filters was washed 3 times with 300 μl ice-cold wash solution (tris, 50 mM; NaCl, 120 mM; $MgCl_2$, 5 mM; dithiothrietol, 1 mM). Filter discs were dried, punched out and counted in a gamma counter at 52% efficiency. Specific binding represented 96% of total binding (approximately 150 fmol angiotensin II/mg protein). The molar concentration (IC50) of the inhibitor that displaced 50% of the binding of $I^{125}$ angiotensin II for each compound was calculated using a 4 parameter logistics model (NonLin, SAS Institute). Data are expressed as $K_I$ (μm) calculated using the Cheng Prusoff equation. See Cheng et al. *Biochem. Pharmacol.* 22: 3099 (1973).

Rabbit Aorta Test System

New Zealand white rabbits Hazelton, 2–3 kg) were sacrificed by cervical dislocation. The thoracic aortae were removed and cleaned of excess fat and connective tissue. Rings of tissue (3 mm wide) were mounted in 10 ml tissue baths between 2 L-shaped stainless steel hooks. The lower hook was attached to a stationary rod. The upper hook was attached to a force displacement transducer (Grass model FT.03). The bath chambers were maintained at 37° C., aerated with 95% $O_2$/5% $CO_2$, and contained physiological solution of the following composition (mM): NaCl, 117; glucose, 5.6; $NaH_2PO_4$, 1.0; $MgSO_4$, 0.7; KCl , 5.2; $CaCl_2$, 1.3; $NaHCO_3$, 26; and phentolamine HCl, 0.003.

Rings were equilibrated for 1 hour with 2 g of tension. During the equilibration period, the tissues were washed by overflow every 15 minutes. Rings were then exposed to $10^{-8}$M angiotensin II (AII) and were allowed to contract until a steady state was reached. Tissues were then washed every 15 minutes for 1 hour. This was repeated every hour until the AII response stabilized. A cumulative concentration response curve to AII ($10^{-10}$ to $10^{-7}$M) was then obtained. At the conclusion of the concentration response curve, tissues were washed every 2 minutes until baseline tension was reached, then every 15 minutes for 30 minutes. Compounds were added in a volume of 10 μl DMSO and allowed to incubate for 30 minutes before repeating the concentration response curve to AII. Contractions to AII were expressed as a percent of the maximum contraction obtained in the control curve (the first AII concentration response curve). $EC_{50}$'s (concentration that contracted the tissues to ½ the control maximum) for each curve were calculated using a 4 parameter logistics model (NonLin, SAS Institute). Potency is expressed as the $PA_2$ (defined as $-\log K_B$, where $K_B$=[molar concentration of antagonist]/[($EC_{50}$ AII with antagonist/$EC_{50}$ AII without antagonist)−1]).

Using the methology described, representative compounds of the present invention were evaluated and were found to exhibit activity as measured by a $pA_2$ of at least 4.1 using the rabbit aorta test system thereby demonstrating and confirming the utility of the compounds of the invention as effective angiotensin II antagonists.

TABLE 1

| Example | Adrenal Glomerulosa ($K_I$, μm) | Rabbit Aorta ($pA_2$) |
| --- | --- | --- |
| 1 | 3.86 | 6.7 |
| 2 | 9.45 | 6.3 |
| 3 | 5.60 | 7.6 |
| 4 | * | 5.3 |
| 5 | 0.36 | 7.4 |
| 6 | 0.085 | 7.1 |
| 7 | * | 7.6 |
| 8 | * | 7.0 |
| 9 | 0.029 | 7.7 |
| 10 | * | 6.6 |

TABLE 1-continued

| Example | Adrenal Glomerulosa ($K_I$, μm) | Rabbit Aorta ($pA_2$) |
|---|---|---|
| 11 | * | 6.7 |
| 12 | * | 7.4 |
| 13 | 0.0042 | 7.5 |
| 14 | 1.08 | 6.0 |
| 15 | * | 7.1 |
| 16 | * | 7.2 |
| 17 | * | 7.2 |
| 18 | * | 7.2 |
| 19 | * | 6.6 |
| 20 | * | 7.7 |
| 21 | 2.26 | 7.9 |
| 22 | 1.72 | 7.7 |
| 23 | * | 6.0 |
| 24 | 13.7 | 6.4 |
| 25 A | * | 6.5 |
| B | | 7.3 |
| 26 | 5.72 | 6.4 |
| 27 2H | 5.43 | 6.7 |
| 1H | | 7.0 |
| 28 | 14.3 | 5.4 |
| 29 | 19.2 | 5.4 |
| 30 | * | 6.5 |
| 31 | * | 7.3 |
| 32 | * | 6.7 |
| 33 | * | 6.8 |
| 34 | 0.062 | 7.2 |
| 35 | * | 6.7 |
| 36 | * | 6.4 |
| 37 | 0.0814 | 7.1 |
| 38 | * | 6.1 |
| 39 | * | 6.2 |
| 40 | 0.25 | 6.6 |
| 41 | 0.10 | 7.0 |
| 42 | 0.265 | 6.5 |
| 43 | 0.069 | 7.2 |
| 44 | 0.199 | 6.8 |
| 45 | * | 5.7 |
| 46 | * | 6.8 |
| 47 | * | 6.4 |
| 48 | * | 8.2 |
| 49 | * | 7.4 |
| 50 | * | 7.2 |
| 51 | * | 6.2 |
| 52 | * | 6.9 |
| 53 | * | 7.6 |
| 54 | * | 8.4 |
| 55 | * | 4.1 |
| 56 | * | 7.3 |
| 57 | * | 6.9 |
| 58 | * | 7.3 |
| 59 | * | 5.8 |
| 60 | * | 6.2 |
| 61 | * | 5.4 |
| 62 | * | 8.5 |
| 63 | * | 8.9 |
| 64 | * | 7.0 |
| 65 | * | 6.3 |
| 66 | * | 9.1 |

*indicates data not available

The term "pharmaceutically effective amount", as used herein, represents an amount of a compound of the invention which is capable of blocking angiotensin II receptors in mammals. The particular dose of the compound administered according to this invention will, of course, be determined by the particular circumstances surrounding the case, including the compound administered, the route of administration, the particular condition being treated, and similar considerations. The compounds can be administered by a variety of routes including the oral, rectal, transdermal, subcutaneous, intravenous, intraocular, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg. The term "treating," as used herein, describes the management and care of a patient for the purpose of combating the disease, condition, or disorder. The term "treating" includes the administration of a compound of present invention to prevent the onset of the symptoms, alleviating the symptoms, or eliminating the disease, condition, or disorder.

The term "enhancing cognitive performance," as used herein, describes facilitating memory and learning in patients in need of such treatment. Examples include patients suffering from cognitive impairments like age associated mental impairment and Alzheimer's disease.

The compounds of Formula I are preferably formulated prior to administration. Therefore, yet another embodiment of the present invention is a pharmaceutical formulation comprising a compound of Formula I and one or more pharmaceutically acceptable carriers, diluents or excipients therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium) ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 co about 300 mg, of the active ingredient. The term "unit dosage form" refers to physically discrete units suitable as unitary dosages for human subjects and ocher mammals, each unit containing a predetermined quantity on active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| 1-[1-Oxo-2-[5-[2-(1H-tetrazol-5-yl)phenyl]-1H-benzimidazol-1-yl]octyl]-4-(4-t-butyloxyphenoxy)-L- | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/capsule) |
|---|---|
| 1-[1-Oxo-2-[5-[2-sulfophenyl]-1H-benzimidazol-1-yl]octyl]-4-cis-(4-thiomethoxyphenoxy)-L-proline | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

| | Quantity (mg/capsule) |
|---|---|
| 1-[1-Oxo-2[5-[2-sulfophenyl]-1H-benzimidazol-1-yl]octyl]-4-cis-(4-hydroxyphenoxy)-L-proline | 0.25 |
| ethanol | 29.75 |
| Propellant 22 | 70.00 |
| (chlorodifluoromethane) | |
| Total | 100.00 |

The active compound is mixed with ethanol. The mixture is added to a portion of the Propellant 22, cooled to −30° C. and transferred co a filling device. The required amount is then fed co a stainless steel container and diluted with the remainder of the propellant. The valve units are then fitted to the container.

Formulation 4

Tablets each containing 60 mg of active ingredient are made as follows:

| | Quantity (mg/capsule) |
|---|---|
| 1-[1-Oxo-2-[5-[2-(1H-tetrazol-5-yl)phenyl]-1H-benzimidazol-1-yl]octyl]-4-cis-(4-methoxyphenoxy)-L-proline. | 60 mg |
| starch | 45 mg |
| microcrystalline cellulose | 35 mg |
| polyvinylpyrrolidone | 4 mg |
| (as 100% solution in water) sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | Quantity (mg/capsule) |
|---|---|
| 1-[1-Oxo-2-[5-[2-sulfophenyl]-1H-benzimidazol-1-yl]octyl]-4-cis-((4-methylene phosphonic acid)-L-proline. | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| | Quantity (mg/capsule) |
|---|---|
| 1-[1-Oxo-2-[5-[2-(2H-tetrazol-5-yl)phenyl]-1H-benzimidazol-1-yl]octyl]-4-cis-(4-carboxymethylphenoxy)-L-proline. | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary,. The mixture is then poured into a suppository mold of nominal 2 g capacity and allowed to cool.

| Formulation 7 |
| Suspensions each containing 50 mg of medicamenc per 5 ml dose are made as follows: |

|  | Quantity (mg/capsule) |
| --- | --- |
| 1-[1-Oxo-2-[5-[2-(2H-tatrazol-5-yl)phenyl]-1H-benzimidazol-1-yl]octyl-4-trans-(4-methoxyphenoxy-L-proline | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

| Formulation 8 |
| An intravenous formulation may be prepared as follows: |

|  | Quantity (mg/capsule) |
| --- | --- |
| 1-[1-Oxo-2-[5-[2-sulfophenyl]-1H-benzimidazol-1-yl]octyl]-4-cis-phenoxy-L-proline | 250 mg |
| isotonic saline | 1000 mg |

The solution of the above ingredients is administered intravenously at a rate of 1 ml per minute to a subject in need of treatment.

We claim:

1. A process for preparing compounds of the formula:

$R_1'$—$R_2'$ wherein:

$R_1'$ is

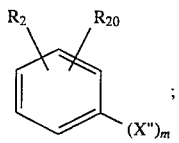

$R_2'$ is

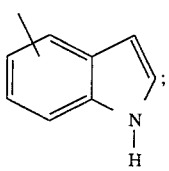

$R_2$ is H, —OH, —OCOCH$_3$, halo, $C_1$–$C_4$ alkyl, or $C_1$–$C_4$ alkoxy;

$R_{20}$ is

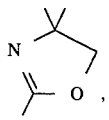

a protected carboxy, cyano, nitro or methoxy, located ortho or para to X";

X" is —CH$_2$—;

m is independently 0 or 1;

which comprises a. reacting a compound of the formula

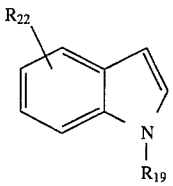

wherein $R_{22}$ is bromo, iodo, —CH$_2$-bromo, or —CH$_2$-iodo; and $R_{19}$ is an indole protecting group; with a reagent selected from an alkyl lithium, MgBr$_2$ or Mg, ZnCl$_2$ or Zn, or diisobutylaluminum to prepare a compound of formula IV

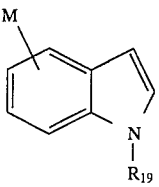     IV wherein

M is —Li, —CH$_2$Li, —MgBr, —MgI, —CH$_2$MgBr, —CH$_2$MgI, —ZnBr, —ZnI, —CH$_2$ZnBr, —CH$_2$ZnI; or Al (isoButyl)$_2$;

b. reacting the compound of Formula IV in the presence of a Ni (0) or Pd (0) complex catalyst in an aprotic solvent with a compound of the Formula V

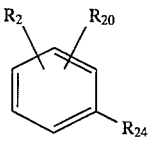     V wherein $R_2$ is H, —OH, —OCOCH$_3$, halo, $C_1$–$C_4$ alkyl, or $C_1$–$C_4$ alkoxy;

$R_{20}$ is

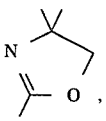

a protected carboxy, cyano, nitro, or methoxy, located in a position ortho or para to $R_{24}$: and $R_{24}$ is bromo or iodo; to produce an indole of Formula VI

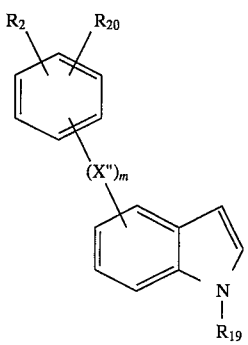

VI wherein X" is —CH$_2$—; and m is 0 or 1;

c. isolating the compound of Formula VI; and d. deprotecting the indole of the compound of Formula VI.

2. A process for preparing compounds of the formula:

wherein:

R$_1'$ is

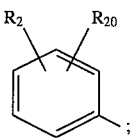

R$_2'$ is

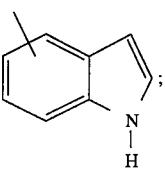

R$_2$ is H, —OH, —OCOCH$_3$, halo, C$_1$–C$_4$ alkyl, or C$_1$–C$_4$ alkoxy;

R$_{20}$ is

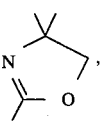

a protected carboxy, cyano, nitro or methoxy, located ortho or para to R$_2'$ which comprises a. reacting a compound of the formula

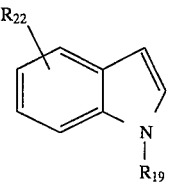

wherein R$_{22}$ is bromo or iodo; and R$_{19}$ is an indole protecting group; with a reagent selected from an alkyl lithium, MgBr$_2$ or Mg, ZnCl$_2$ or Zn, or diisobutylaluminum to prepare a compound of formula IV

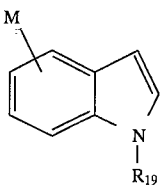

IV wherein M is LiR$_{22}$, MgR$_{22}$, ZnR$_{22}$, or Al (iso-Butyl )$_2$ respectively;

b. reacting the compound of Formula IV in the presence of a Ni(0) or Pd(0) complex catalyst in an aprotic solvent with a compound of the Formula V

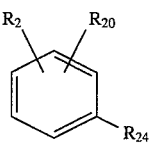

V wherein

R$_2$ is H, —OH, —OCOCH$_3$, halo, C$_1$–C$_4$ alkyl, or C$_1$–C$_4$ alkoxy;

R$_{20}$ is

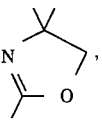

a protected carboxy, cyano, nitro, or methoxy, located in a position ortho or para to R$_{24}$; and R$_{24}$ is bromo or iodo; to produce an indole of Formula VI

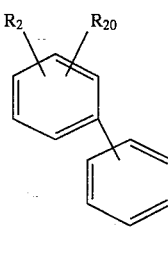

VI c. isolating the compound of Formula VI; and d. deprotecting the indole of the compound of Formula VI.

* * * * *